(12) United States Patent
Faucher et al.

(10) Patent No.: US 10,864,304 B2
(45) Date of Patent: Dec. 15, 2020

(54) ANTI-INFECTIVE ANTIMICROBIAL-CONTAINING BIOMATERIALS

(71) Applicant: ATRIUM MEDICAL CORPORATION, Merrimack, NH (US)

(72) Inventors: Keith M. Faucher, Milford, NH (US); Hilda N. Rono, Chelmsford, MA (US); Anthony Richard Horton, Manchester, NH (US); Jocelyn Choroszy, Waltham, MA (US); Paul Martakos, Pelham, NH (US)

(73) Assignee: ATRIUM MEDICAL CORPORATION, Merrimack, NH (US)

( * ) Notice: Subject to any disclaimer, the term of this patent is extended or adjusted under 35 U.S.C. 154(b) by 0 days.

(21) Appl. No.: 14/281,682

(22) Filed: May 19, 2014

(65) Prior Publication Data
US 2015/0024018 A1 Jan. 22, 2015

Related U.S. Application Data

(63) Continuation of application No. 12/539,282, filed on Aug. 11, 2009, now abandoned.

(51) Int. Cl.
| | |
|---|---|
| *A61L 31/08* | (2006.01) |
| *A61L 31/16* | (2006.01) |
| *A61L 31/14* | (2006.01) |
| *A61K 31/202* | (2006.01) |
| *A61L 15/46* | (2006.01) |
| *A61K 31/765* | (2006.01) |
| *A61L 27/50* | (2006.01) |
| *A61L 29/14* | (2006.01) |
| *A01N 37/36* | (2006.01) |
| *A61K 33/38* | (2006.01) |
| *A61K 31/232* | (2006.01) |
| *A61K 31/35* | (2006.01) |
| *A61L 15/34* | (2006.01) |
| *A61L 27/54* | (2006.01) |
| *A01N 61/00* | (2006.01) |
| *A61L 29/16* | (2006.01) |
| *A61K 31/155* | (2006.01) |
| *A61K 45/06* | (2006.01) |
| *A61K 31/09* | (2006.01) |
| *A61L 31/00* | (2006.01) |

(52) U.S. Cl.
CPC .............. *A61L 31/08* (2013.01); *A01N 37/36* (2013.01); *A01N 61/00* (2013.01); *A61K 31/09* (2013.01); *A61K 31/155* (2013.01); *A61K 31/202* (2013.01); *A61K 31/232* (2013.01); *A61K 31/35* (2013.01); *A61K 31/765* (2013.01); *A61K 33/38* (2013.01); *A61K 45/06* (2013.01); *A61L 15/34* (2013.01); *A61L 15/46* (2013.01); *A61L 27/50* (2013.01); *A61L 27/54* (2013.01); *A61L 29/14* (2013.01); *A61L 29/16* (2013.01); *A61L 31/005* (2013.01); *A61L 31/14* (2013.01); *A61L 31/16* (2013.01); *A61L 2300/104* (2013.01); *A61L 2300/22* (2013.01); *A61L 2300/404* (2013.01); *A61L 2300/406* (2013.01); *A61L 2300/45* (2013.01); *A61L 2300/602* (2013.01); *A61L 2300/624* (2013.01); *A61L 2420/06* (2013.01)

(58) Field of Classification Search
CPC ................................ A61L 31/08; A61K 33/38
See application file for complete search history.

(56) References Cited

U.S. PATENT DOCUMENTS

| | | | |
|---|---|---|---|
| 1,948,959 | A | 2/1934 | Croce |
| 2,368,306 | A | 1/1945 | Kiefer |
| 2,403,458 | A | 7/1946 | Ransom et al. |
| 2,555,976 | A | 6/1951 | Keenan |
| 2,735,814 | A | 2/1956 | Hodson et al. |
| 2,986,540 | A | 5/1961 | Posnansky |
| 3,328,259 | A | 6/1967 | Anderson |
| 3,464,413 | A | 9/1969 | Alvin |
| 3,556,294 | A | 1/1971 | George |
| 3,567,820 | A | 3/1971 | George |
| 3,803,109 | A | 4/1974 | Nemoto et al. |
| 3,967,728 | A | 7/1976 | Gordon et al. |
| 4,185,637 | A | 1/1980 | Mattei |
| 4,308,120 | A | 12/1981 | Pennewiss et al. |
| 4,323,547 | A | 4/1982 | Knust et al. |
| 4,345,414 | A | 8/1982 | Bornat et al. |

(Continued)

FOREIGN PATENT DOCUMENTS

| | | |
|---|---|---|
| CN | 1360951 A | 7/2002 |
| CN | 1429559 | 7/2003 |

(Continued)

OTHER PUBLICATIONS

Berchert et al., "A New Method for Screening Anti-Infective Biomaterials", Nature Medicine. 6(8):1053-1056(2000).

(Continued)

*Primary Examiner* — Dennis J Parad

(74) *Attorney, Agent, or Firm* — Wesley Scott Ashton

(57) ABSTRACT

A material including a plurality of fatty acid chains cross-linked together and a silver fatty acid salt formed with the fatty acid chains within the material. Methods for forming a material are also included. The silver-containing materials can be utilized alone or in combination with a medical device for the release and local delivery of one or more anti-infective agents.

22 Claims, 32 Drawing Sheets

(56) References Cited

U.S. PATENT DOCUMENTS

| | | |
|---|---|---|
| 4,447,418 A | 5/1984 | Maddoux |
| 4,557,925 A | 12/1985 | Lindahl et al. |
| 4,655,221 A | 4/1987 | Devereux |
| 4,664,114 A | 5/1987 | Ghodsian |
| 4,702,252 A | 10/1987 | Brooks et al. |
| 4,711,902 A | 12/1987 | Serno |
| 4,733,665 A | 3/1988 | Palmaz |
| 4,769,038 A | 9/1988 | Bendavid et al. |
| 4,813,210 A | 3/1989 | Masuda et al. |
| 4,814,329 A | 3/1989 | Harsanyi et al. |
| 4,824,436 A | 4/1989 | Wolinsky |
| 4,846,844 A | 4/1989 | De Leon et al. |
| 4,847,301 A | 7/1989 | Murray |
| 4,880,455 A | 11/1989 | Blank |
| 4,883,667 A | 11/1989 | Eckenhoff |
| 4,886,787 A | 12/1989 | de Belder et al. |
| 4,894,231 A | 1/1990 | Moreau et al. |
| 4,895,724 A | 1/1990 | Cardinal et al. |
| 4,911,707 A | 3/1990 | Heiber et al. |
| 4,937,254 A | 6/1990 | Sheffield et al. |
| 4,938,763 A | 7/1990 | Dunn et al. |
| 4,941,308 A | 7/1990 | Grabenkort et al. |
| 4,941,877 A | 7/1990 | Montano, Jr. |
| 4,947,840 A | 8/1990 | Yannas et al. |
| 4,952,419 A | 8/1990 | De Leon et al. |
| 4,968,302 A | 11/1990 | Schluter et al. |
| 4,994,033 A | 2/1991 | Shockey et al. |
| 5,017,229 A | 5/1991 | Burns et al. |
| 5,019,096 A | 5/1991 | Fox, Jr. et al. |
| 5,041,125 A | 8/1991 | Montano, Jr. |
| 5,049,132 A | 9/1991 | Shaffer et al. |
| 5,061,281 A | 10/1991 | Mares et al. |
| 5,071,609 A | 12/1991 | Tu et al. |
| 5,087,244 A | 2/1992 | Vvolinsky et al. |
| 5,087,246 A | 2/1992 | Smith |
| 5,102,402 A | 4/1992 | Dror et al. |
| 5,118,493 A | 6/1992 | Kelley et al. |
| 5,132,115 A | 7/1992 | Wolter et al. |
| 5,147,374 A | 9/1992 | Fernandez |
| 5,151,272 A | 9/1992 | Engstrom et al. |
| 5,171,148 A | 12/1992 | Wasserman et al. |
| 5,176,956 A | 1/1993 | Jevne et al. |
| 5,179,174 A | 1/1993 | Elton |
| 5,199,951 A | 4/1993 | Spears |
| 5,202,310 A | 4/1993 | Levy et al. |
| 5,206,077 A | 4/1993 | Cowley et al. |
| 5,254,105 A | 10/1993 | Haaga |
| 5,267,985 A | 12/1993 | Shimada et al. |
| 5,279,565 A | 1/1994 | Klein et al. |
| 5,282,785 A | 2/1994 | Shapland et al. |
| 5,283,257 A | 2/1994 | Gregory et al. |
| 5,286,254 A | 2/1994 | Shapland et al. |
| 5,295,962 A | 3/1994 | Crocker et al. |
| 5,304,121 A | 4/1994 | Sahatjian |
| 5,336,178 A | 8/1994 | Kaplan et al. |
| 5,356,432 A | 10/1994 | Rutkow et al. |
| 5,368,602 A | 11/1994 | de la Torre |
| 5,371,109 A | 12/1994 | Engstrom et al. |
| 5,380,328 A | 1/1995 | Morgan |
| 5,387,658 A | 2/1995 | Schroder et al. |
| 5,403,283 A | 4/1995 | Luther |
| 5,411,951 A | 5/1995 | Mitchell |
| 5,411,988 A | 5/1995 | Bockow et al. |
| 5,447,940 A | 9/1995 | Harvey et al. |
| 5,456,666 A | 10/1995 | Campbell et al. |
| 5,456,720 A | 10/1995 | Schultz et al. |
| 5,458,568 A | 10/1995 | Racchini et al. |
| 5,458,572 A | 10/1995 | Racchini et al. |
| 5,464,650 A | 11/1995 | Berg et al. |
| 5,468,242 A | 11/1995 | Reisberg |
| 5,480,653 A | 1/1996 | Aguadisch et al. |
| 5,490,839 A | 2/1996 | Wang et al. |
| 5,498,238 A | 3/1996 | Shapland et al. |
| 5,499,971 A | 3/1996 | Shapland et al. |
| 5,502,077 A | 3/1996 | Breivik et al. |
| 5,509,899 A | 4/1996 | Fan et al. |
| 5,514,092 A | 5/1996 | Forman et al. |
| 5,547,677 A | 8/1996 | Wright |
| 5,549,901 A | 8/1996 | Wright |
| 5,558,071 A | 9/1996 | Ward et al. |
| 5,569,198 A | 10/1996 | Racchini |
| 5,579,149 A | 11/1996 | Moret et al. |
| 5,573,781 A | 12/1996 | Brown et al. |
| 5,580,923 A | 12/1996 | Yeung et al. |
| 5,589,508 A | 12/1996 | Schlotzer et al. |
| 5,591,230 A | 1/1997 | Horn et al. |
| 5,593,441 A | 1/1997 | Lichtenstein et al. |
| 5,603,721 A | 2/1997 | Lau et al. |
| 5,605,696 A | 2/1997 | Eury et al. |
| 5,612,074 A | 3/1997 | Leach |
| 5,614,284 A | 3/1997 | Kranzler et al. |
| 5,627,077 A | 5/1997 | Dyllick-Brenzinger et al. |
| 5,628,730 A | 5/1997 | Shapland et al. |
| 5,629,021 A | 5/1997 | Wright |
| 5,634,899 A | 6/1997 | Shapland et al. |
| 5,637,113 A | 6/1997 | Tartaglia et al. |
| 5,637,317 A | 6/1997 | Hans |
| 5,641,767 A | 6/1997 | Wess et al. |
| 5,665,115 A | 9/1997 | Cragg |
| 5,693,014 A | 12/1997 | Abele et al. |
| 5,695,525 A | 12/1997 | Mulhauser et al. |
| 5,700,286 A | 12/1997 | Tartaglia et al. |
| 5,700,848 A | 12/1997 | Soon-Shiong |
| 5,705,485 A | 1/1998 | Cini et al. |
| 5,731,346 A | 3/1998 | Egberg et al. |
| 5,736,152 A | 4/1998 | Dunn |
| 5,738,869 A | 4/1998 | Fischer et al. |
| 5,747,533 A | 5/1998 | Egberg et al. |
| 5,749,845 A | 5/1998 | Hildebrand et al. |
| 5,753,259 A | 5/1998 | Engstrom et al. |
| 5,760,081 A | 6/1998 | Leaf et al. |
| 5,766,246 A | 6/1998 | Mulhauser et al. |
| 5,766,710 A | 6/1998 | Turnlund et al. |
| 5,789,465 A | 8/1998 | Harvey et al. |
| 5,800,392 A | 9/1998 | Racchini |
| 5,807,306 A | 9/1998 | Shapland et al. |
| 5,817,343 A | 10/1998 | Burke |
| 5,824,082 A | 10/1998 | Brown |
| 5,827,325 A | 10/1998 | Landgrebe et al. |
| 5,828,785 A | 10/1998 | Kitsuki |
| 5,837,313 A | 11/1998 | Ding et al. |
| 5,843,172 A | 12/1998 | Yan |
| 5,843,919 A | 12/1998 | Burger |
| 5,865,787 A | 2/1999 | Shapland et al. |
| 5,874,470 A | 2/1999 | Nehne et al. |
| 5,879,359 A | 3/1999 | Dorigatti et al. |
| 5,897,911 A | 4/1999 | Loeffler |
| 5,898,040 A | 4/1999 | Shalaby et al. |
| 5,902,266 A | 5/1999 | Leone et al. |
| 5,906,831 A | 5/1999 | Larsson et al. |
| 5,931,165 A | 8/1999 | Reich et al. |
| 5,947,977 A | 9/1999 | Slepian et al. |
| 5,954,767 A | 9/1999 | Pajotin et al. |
| 5,955,502 A | 9/1999 | Hansen et al. |
| 5,986,043 A | 11/1999 | Hubbell et al. |
| 6,004,549 A | 12/1999 | Reichert et al. |
| 6,005,004 A | 12/1999 | Katz et al. |
| 6,010,480 A | 1/2000 | Abele et al. |
| 6,010,766 A | 1/2000 | Braun et al. |
| 6,010,776 A | 1/2000 | Exsted et al. |
| 6,013,055 A | 1/2000 | Bampos et al. |
| 6,015,844 A | 1/2000 | Harvey et al. |
| 6,028,164 A | 2/2000 | Loomis |
| 6,033,380 A | 3/2000 | Butaric et al. |
| 6,033,436 A | 3/2000 | Steinke et al. |
| 6,040,330 A | 3/2000 | Hausheer et al. |
| 6,048,332 A | 4/2000 | Duffy et al. |
| 6,048,725 A | 4/2000 | Shimada et al. |
| 6,056,970 A | 5/2000 | Greenawalt et al. |
| 6,066,777 A | 5/2000 | Benchetrit |
| 6,075,180 A | 6/2000 | Sharber et al. |
| 6,077,698 A | 6/2000 | Swan et al. |
| 6,080,442 A | 6/2000 | Yoshikawa et al. |
| 6,083,950 A | 7/2000 | Anand et al. |

(56) References Cited

U.S. PATENT DOCUMENTS

| | | | |
|---|---|---|---|
| 6,090,809 A | 7/2000 | Anand et al. | |
| 6,093,792 A | 7/2000 | Gross et al. | |
| 6,117,911 A | 9/2000 | Grainger et al. | |
| 6,120,477 A | 9/2000 | Campbell et al. | |
| 6,120,539 A | 9/2000 | Eldridge et al. | |
| 6,120,789 A | 9/2000 | Dunn | |
| 6,132,765 A | 10/2000 | DiCosmo et al. | |
| 6,146,358 A | 11/2000 | Rowe | |
| 6,152,944 A | 11/2000 | Holman et al. | |
| 6,176,863 B1 | 1/2001 | Kugel et al. | |
| 6,193,746 B1 | 2/2001 | Strecker | |
| 6,197,357 B1 | 3/2001 | Lawton et al. | |
| 6,200,985 B1 | 3/2001 | Cottens et al. | |
| 6,203,551 B1 | 3/2001 | Wu | |
| 6,206,916 B1 | 3/2001 | Furst | |
| 6,211,315 B1 | 4/2001 | Larock et al. | |
| 6,224,579 B1 * | 5/2001 | Modak | A01N 59/16 424/422 |
| 6,224,909 B1 | 5/2001 | Opitz et al. | |
| 6,228,383 B1 | 5/2001 | Hansen et al. | |
| 6,229,032 B1 | 5/2001 | Jacobs et al. | |
| 6,231,600 B1 | 5/2001 | Zhong | |
| 6,245,366 B1 | 6/2001 | Popplewell et al. | |
| 6,245,811 B1 | 6/2001 | Horrobin et al. | |
| 6,258,124 B1 | 6/2001 | Darois et al. | |
| 6,254,634 B1 | 7/2001 | Anderson et al. | |
| 6,262,109 B1 | 7/2001 | Clark et al. | |
| 6,273,913 B1 | 8/2001 | Wright et al. | |
| 6,284,268 B1 | 9/2001 | Mishra et al. | |
| 6,287,285 B1 | 9/2001 | Michal et al. | |
| 6,287,316 B1 | 9/2001 | Agarwal | |
| 6,299,604 B1 | 10/2001 | Ragheb | |
| 6,306,438 B1 | 10/2001 | Oshlack et al. | |
| 6,326,072 B1 | 12/2001 | Ojeda et al. | |
| 6,326,360 B1 | 12/2001 | Kanazawa et al. | |
| 6,331,568 B1 | 12/2001 | Horrobin | |
| 6,342,254 B1 | 1/2002 | Soudant et al. | |
| 6,346,110 B2 | 2/2002 | Wu | |
| 6,355,063 B1 | 3/2002 | Calcote | |
| 6,358,556 B1 | 3/2002 | Ding et al. | |
| 6,364,856 B1 | 4/2002 | Ding et al. | |
| 6,364,893 B1 | 4/2002 | Sahatjian et al. | |
| 6,364,903 B2 | 4/2002 | Tseng et al. | |
| 6,368,541 B1 | 4/2002 | Pajotin et al. | |
| 6,368,658 B1 | 4/2002 | Schwarz et al. | |
| 6,369,039 B1 | 4/2002 | Palasis et al. | |
| 6,387,301 B1 | 5/2002 | Nakajima et al. | |
| 6,387,379 B1 | 5/2002 | Goldberg et al. | |
| 6,410,587 B1 | 6/2002 | Grainger et al. | |
| 6,444,318 B1 | 9/2002 | Guire et al. | |
| 6,451,373 B1 | 9/2002 | Hossainy et al. | |
| 6,463,323 B1 | 10/2002 | Conrad-Vlasak et al. | |
| 6,465,525 B1 | 10/2002 | Guire et al. | |
| 6,471,980 B2 | 10/2002 | Sirhan et al. | |
| 6,479,683 B1 | 11/2002 | Abney et al. | |
| 6,485,752 B1 | 11/2002 | Rein | |
| 6,491,938 B2 | 12/2002 | Kunz et al. | |
| 6,500,174 B1 | 12/2002 | Maguire | |
| 6,500,453 B2 | 12/2002 | Brey et al. | |
| 6,503,556 B2 | 1/2003 | Harish et al. | |
| 6,506,410 B1 | 1/2003 | Park et al. | |
| 6,525,145 B2 | 2/2003 | Gevaert et al. | |
| 6,527,801 B1 | 3/2003 | Dutta | |
| 6,534,693 B2 | 3/2003 | Fischell et al. | |
| 6,541,116 B2 | 4/2003 | Michal et al. | |
| 6,544,223 B1 | 4/2003 | Kokish | |
| 6,544,224 B1 | 4/2003 | Steese-Bradley | |
| 6,548,081 B2 | 4/2003 | Sadozai et al. | |
| 6,565,659 B1 | 5/2003 | Pacetti et al. | |
| 6,569,441 B2 | 5/2003 | Kunz et al. | |
| 6,579,851 B2 | 6/2003 | Goeke et al. | |
| 6,596,002 B2 | 7/2003 | Therin et al. | |
| 6,599,323 B2 | 7/2003 | Melican et al. | |
| 6,610,006 B1 | 8/2003 | Amid et al. | |
| 6,610,035 B2 | 8/2003 | Yang et al. | |
| 6,610,068 B1 | 8/2003 | Yang | |
| 6,616,650 B1 | 9/2003 | Rowe | |
| 6,630,151 B1 | 10/2003 | Tarletsky et al. | |
| 6,630,167 B2 | 10/2003 | Zhang | |
| 6,632,822 B1 | 10/2003 | Rickards et al. | |
| 6,641,611 B2 | 11/2003 | Jayaraman | |
| 6,645,547 B1 | 11/2003 | Shekalim et al. | |
| 6,663,880 B1 | 12/2003 | Roorda et al. | |
| 6,669,735 B1 | 12/2003 | Pelissier | |
| 6,670,355 B2 | 12/2003 | Azrolan et al. | |
| 6,677,342 B2 | 1/2004 | Wolff et al. | |
| 6,677,386 B1 | 1/2004 | Giezen et al. | |
| 6,685,956 B2 | 2/2004 | Chu et al. | |
| 6,689,388 B2 | 2/2004 | Kuhrts | |
| 6,696,583 B2 | 2/2004 | Koncar et al. | |
| 6,723,133 B1 | 4/2004 | Pajotin | |
| 6,730,016 B1 | 5/2004 | Cox et al. | |
| 6,730,064 B2 | 5/2004 | Ragheb et al. | |
| 6,740,122 B1 | 5/2004 | Pajotin | |
| 6,753,071 B1 | 6/2004 | Pacetti | |
| 6,758,847 B2 | 7/2004 | Maguire | |
| 6,761,903 B2 | 7/2004 | Chen et al. | |
| 6,764,509 B2 | 7/2004 | Chinn et al. | |
| 6,776,796 B2 | 8/2004 | Falotico et al. | |
| 6,794,485 B2 | 9/2004 | Shalaby et al. | |
| 6,808,536 B2 | 10/2004 | Wright et al. | |
| 6,833,004 B2 | 12/2004 | Ishii et al. | |
| 6,852,330 B2 | 2/2005 | Bowman et al. | |
| 6,875,230 B1 | 4/2005 | Morita et al. | |
| 6,884,428 B2 | 4/2005 | Binette et al. | |
| 6,887,270 B2 | 5/2005 | Miller et al. | |
| 6,899,729 B1 | 5/2005 | Cox et al. | |
| 6,902,522 B1 | 6/2005 | Walsh et al. | |
| 6,918,927 B2 | 7/2005 | Bates et al. | |
| 6,996,952 B2 | 2/2006 | Gupta et al. | |
| 7,070,858 B2 | 7/2006 | Shalaby et al. | |
| 7,090,655 B2 | 8/2006 | Barry | |
| 7,101,381 B2 | 9/2006 | Ford et al. | |
| 7,112,209 B2 | 9/2006 | Ramshaw et al. | |
| 7,135,164 B2 | 11/2006 | Rojanapanthu et al. | |
| 7,152,611 B2 | 12/2006 | Brown et al. | |
| 7,311,980 B1 | 12/2007 | Hossainy et al. | |
| 7,323,178 B1 | 1/2008 | Zhang et al. | |
| 7,323,189 B2 | 1/2008 | Pathak | |
| 7,415,811 B2 | 8/2008 | Gottlieb et al. | |
| 7,691,946 B2 | 4/2010 | Liu et al. | |
| 7,854,958 B2 | 12/2010 | Kramer | |
| 7,947,015 B2 | 5/2011 | Herweck et al. | |
| 8,001,922 B2 | 8/2011 | Labrecque et al. | |
| 8,021,331 B2 | 9/2011 | Herweck et al. | |
| 8,124,127 B2 * | 2/2012 | Faucher | A61L 29/08 424/425 |
| 8,298,290 B2 | 10/2012 | Pelissier et al. | |
| 8,308,684 B2 | 11/2012 | Herweck et al. | |
| 8,312,836 B2 | 11/2012 | Corbeil et al. | |
| 8,461,129 B2 | 6/2013 | Bolduc et al. | |
| 8,501,229 B2 | 8/2013 | Faucher et al. | |
| 8,722,077 B2 | 5/2014 | Labrecque et al. | |
| 8,888,887 B2 | 11/2014 | Hargrove et al. | |
| 9,000,040 B2 | 4/2015 | Faucher et al. | |
| 9,012,506 B2 | 4/2015 | Faucher et al. | |
| 9,220,820 B2 | 12/2015 | Faucher et al. | |
| 9,278,161 B2 | 3/2016 | Swanick et al. | |
| 9,427,423 B2 | 8/2016 | Swanick et al. | |
| 9,493,636 B2 | 11/2016 | Ah et al. | |
| 2001/0022988 A1 | 9/2001 | Schwarz et al. | |
| 2001/0025034 A1 | 9/2001 | Arbiser | |
| 2001/0025196 A1 | 9/2001 | Chinn et al. | |
| 2001/0026803 A1 | 10/2001 | Tebbe et al. | |
| 2001/0027299 A1 | 10/2001 | Yang et al. | |
| 2001/0051595 A1 | 12/2001 | Lyons et al. | |
| 2002/0002154 A1 | 1/2002 | Guivarch et al. | |
| 2002/0007209 A1 | 1/2002 | Scheerder et al. | |
| 2002/0012741 A1 | 1/2002 | Heinz et al. | |
| 2002/0013590 A1 | 1/2002 | Therin et al. | |
| 2002/0015970 A1 | 2/2002 | Murray et al. | |
| 2002/0022052 A1 | 2/2002 | Dransfield | |
| 2002/0026899 A1 | 3/2002 | McLaughlin et al. | |
| 2002/0026900 A1 | 3/2002 | Huang et al. | |

(56) References Cited

U.S. PATENT DOCUMENTS

| | | |
|---|---|---|
| 2002/0032414 A1 | 3/2002 | Ragheb et al. |
| 2002/0055701 A1 | 5/2002 | Fischell et al. |
| 2002/0077652 A1 | 6/2002 | Kieturakis et al. |
| 2002/0082679 A1 | 6/2002 | Sirhan et al. |
| 2002/0098278 A1 | 7/2002 | Bates et al. |
| 2002/0103494 A1 | 8/2002 | Pacey |
| 2002/0116045 A1 | 8/2002 | Eidenschink |
| 2002/0120333 A1 | 8/2002 | Keogh et al. |
| 2002/0122877 A1 | 9/2002 | Harish et al. |
| 2002/0127327 A1 | 9/2002 | Schwarz et al. |
| 2002/0142089 A1 | 10/2002 | Koike et al. |
| 2002/0183716 A1 | 12/2002 | Herweck et al. |
| 2002/0192352 A1 | 12/2002 | Jamshed |
| 2002/0193829 A1 | 12/2002 | Kennedy et al. |
| 2003/0003125 A1 | 1/2003 | Nathan et al. |
| 2003/0003221 A1 | 1/2003 | Zhong et al. |
| 2003/0004564 A1 | 1/2003 | Elkins et al. |
| 2003/0009213 A1 | 1/2003 | Yang |
| 2003/0033004 A1 | 2/2003 | Ishii |
| 2003/0036803 A1 | 2/2003 | McGhan et al. |
| 2003/0055403 A1 | 3/2003 | Nestenborg et al. |
| 2003/0065292 A1 | 4/2003 | Darouiche et al. |
| 2003/0065345 A1 | 4/2003 | Weadock |
| 2003/0069632 A1 | 4/2003 | De Scheerder et al. |
| 2003/0072784 A1 | 4/2003 | Williams |
| 2003/0077272 A1 | 4/2003 | Pathak |
| 2003/0077310 A1 | 4/2003 | Pathak et al. |
| 2003/0077452 A1 | 4/2003 | Guire et al. |
| 2003/0083740 A1 | 5/2003 | Pathak |
| 2003/0086958 A1 | 5/2003 | Arnold et al. |
| 2003/0094728 A1 | 5/2003 | Tayebi |
| 2003/0100955 A1 | 5/2003 | Greenawalt et al. |
| 2003/0108588 A1 | 6/2003 | Chen et al. |
| 2003/0124087 A1 | 7/2003 | Kim et al. |
| 2003/0130206 A1 | 7/2003 | Koziak et al. |
| 2003/0152609 A1 | 8/2003 | Fischell et al. |
| 2003/0175408 A1 | 9/2003 | Timm et al. |
| 2003/0176915 A1 | 9/2003 | Wright et al. |
| 2003/0181975 A1 | 9/2003 | Ishii et al. |
| 2003/0181988 A1 | 9/2003 | Rousseau |
| 2003/0187516 A1 | 10/2003 | Amid et al. |
| 2003/0191179 A1 | 10/2003 | Joshi-Hangal et al. |
| 2003/0204168 A1 | 10/2003 | Bosma et al. |
| 2003/0204618 A1 | 10/2003 | Foster et al. |
| 2003/0207019 A1 | 11/2003 | Shekalim et al. |
| 2003/0211230 A1 | 11/2003 | Pacetti et al. |
| 2003/0212462 A1 | 11/2003 | Gryska et al. |
| 2003/0220297 A1 | 11/2003 | Berstein et al. |
| 2004/0006296 A1 | 1/2004 | Fischell et al. |
| 2004/0013704 A1 | 1/2004 | Kabra et al. |
| 2004/0014810 A1 | 1/2004 | Horrobin |
| 2004/0018228 A1 | 1/2004 | Fischell et al. |
| 2004/0039441 A1 | 2/2004 | Rowland et al. |
| 2004/0058008 A1 | 3/2004 | Tarcha et al. |
| 2004/0060260 A1 | 4/2004 | Gottlieb et al. |
| 2004/0071756 A1 | 4/2004 | Fischell et al. |
| 2004/0072849 A1 | 4/2004 | Schreiber et al. |
| 2004/0073284 A1 | 4/2004 | Bates et al. |
| 2004/0092969 A1 | 5/2004 | Kumar |
| 2004/0102758 A1 | 5/2004 | Davila et al. |
| 2004/0117007 A1 | 6/2004 | Whitbourne et al. |
| 2004/0123877 A1 | 7/2004 | Brown et al. |
| 2004/0131755 A1 | 7/2004 | Zhong et al. |
| 2004/0133275 A1 | 7/2004 | Mansmann |
| 2004/0137066 A1 | 7/2004 | Jayaraman |
| 2004/0142094 A1 | 7/2004 | Narayanan |
| 2004/0146546 A1 | 7/2004 | Gravett et al. |
| 2004/0153125 A1 | 8/2004 | Roby |
| 2004/0156879 A1 | 8/2004 | Muratoglu et al. |
| 2004/0161464 A1 | 8/2004 | Domb |
| 2004/0167572 A1 | 8/2004 | Roth et al. |
| 2004/0170685 A1 | 9/2004 | Carpenter et al. |
| 2004/0192643 A1 | 9/2004 | Pressato et al. |
| 2004/0137179 A1 | 10/2004 | Shojiro et al. |
| 2004/0215219 A1 | 10/2004 | Eldridge et al. |
| 2004/0224003 A1 | 11/2004 | Schultz |
| 2004/0230176 A1 | 11/2004 | Shanahan et al. |
| 2004/0234574 A9 | 11/2004 | Sawhney et al. |
| 2004/0236278 A1 | 11/2004 | Herweck et al. |
| 2004/0241211 A9 | 12/2004 | Fischel) Robert E et al. |
| 2004/0256264 A1 | 12/2004 | Israelsson et al. |
| 2005/0010078 A1 | 1/2005 | Jamiolkowski et al. |
| 2005/0025804 A1 | 2/2005 | Heller |
| 2005/0042251 A1 | 2/2005 | Zhang |
| 2005/0084514 A1 | 4/2005 | Shebuski et al. |
| 2005/0095267 A1 | 5/2005 | Campbell et al. |
| 2005/0100655 A1 | 5/2005 | Zhong et al. |
| 2005/0101522 A1 | 5/2005 | Speck et al. |
| 2005/0106206 A1 | 5/2005 | Herweck et al. |
| 2005/0106209 A1 | 5/2005 | Amen et al. |
| 2005/0112170 A1 | 5/2005 | Hossainy et al. |
| 2005/0113687 A1 | 5/2005 | Herweck et al. |
| 2005/0113849 A1 | 5/2005 | Popadiuk et al. |
| 2005/0124062 A1 | 6/2005 | Subirade et al. |
| 2005/0129787 A1 | 6/2005 | Murad |
| 2005/0154416 A1 | 7/2005 | Herweck et al. |
| 2005/0158361 A1 | 7/2005 | Dhondt et al. |
| 2005/0159809 A1 | 7/2005 | Hezi-Yamit et al. |
| 2005/0165476 A1 | 7/2005 | Furst et al. |
| 2005/0165477 A1 | 7/2005 | Anduiza et al. |
| 2005/0181061 A1 | 8/2005 | Roderick et al. |
| 2005/0182485 A1 | 8/2005 | Falotico et al. |
| 2005/0186244 A1 | 8/2005 | Hunter et al. |
| 2005/0187376 A1 | 8/2005 | Pacetti |
| 2005/0203635 A1 | 9/2005 | Hunter et al. |
| 2005/0203636 A1 | 9/2005 | McFetridge |
| 2005/0223679 A1 | 10/2005 | Gottlieb et al. |
| 2005/0232971 A1 | 10/2005 | Hossainy et al. |
| 2005/0249775 A1 | 11/2005 | Falotico et al. |
| 2005/0283229 A1 | 12/2005 | Dugan |
| 2006/0008501 A1 | 1/2006 | Dhont et al. |
| 2006/0020031 A1 | 1/2006 | Berlin |
| 2006/0030669 A1 | 2/2006 | Taton et al. |
| 2006/0036311 A1 | 2/2006 | Nakayama et al. |
| 2006/0112536 A1 | 2/2006 | Herweck et al. |
| 2006/0051544 A1 | 3/2006 | Goldmann |
| 2006/0058737 A1 | 3/2006 | Herweck et al. |
| 2006/0058881 A1 | 3/2006 | Trieu |
| 2006/0064175 A1 | 3/2006 | Pelissier et al. |
| 2006/0067974 A1 | 3/2006 | Labrecque et al. |
| 2006/0067975 A1 | 3/2006 | Labrecque et al. |
| 2006/0067976 A1 | 3/2006 | Ferraro et al. |
| 2006/0067977 A1 | 3/2006 | Labrecque et al. |
| 2006/0067983 A1 | 3/2006 | Swanick et al. |
| 2006/0068674 A1 | 3/2006 | Dixit et al. |
| 2006/0078586 A1 | 4/2006 | Ferraro et al. |
| 2006/0083768 A1 | 4/2006 | Labrecque et al. |
| 2006/0088596 A1 | 4/2006 | Labrecque et al. |
| 2006/0093643 A1 | 5/2006 | Stenzel |
| 2006/0110457 A1 | 5/2006 | Labrecque et al. |
| 2006/0121081 A1 | 6/2006 | Labrecque et al. |
| 2006/0124056 A1 | 6/2006 | Behnisch et al. |
| 2006/0134209 A1 | 6/2006 | Labhasetwar et al. |
| 2006/0158361 A1 | 7/2006 | Chou |
| 2006/0188607 A1 | 8/2006 | Schramm et al. |
| 2006/0204738 A1 | 9/2006 | Dubrow et al. |
| 2006/0210701 A1 | 9/2006 | Chappa et al. |
| 2006/0240069 A1 | 10/2006 | Utas et al. |
| 2006/0246105 A1 | 11/2006 | Molz et al. |
| 2006/0263330 A1 | 11/2006 | Emeta et al. |
| 2006/0269485 A1 | 11/2006 | Friedman et al. |
| 2007/0003603 A1 | 1/2007 | Karandikar et al. |
| 2007/0015893 A1 | 1/2007 | Hakuta et al. |
| 2007/0071798 A1 | 3/2007 | Herweck et al. |
| 2007/0084144 A1 | 4/2007 | Labrecque et al. |
| 2007/0093894 A1 | 4/2007 | Darouiche |
| 2007/0141112 A1 | 6/2007 | Falotico et al. |
| 2007/0198040 A1 | 8/2007 | Buevich et al. |
| 2007/0202149 A1 | 8/2007 | Faucher et al. |
| 2007/0212411 A1 | 9/2007 | Fawzy et al. |
| 2007/0218182 A1 | 9/2007 | Schneider et al. |
| 2007/0238697 A1 | 10/2007 | Jackson et al. |
| 2007/0264460 A1 | 11/2007 | Del Tredici |
| 2007/0275074 A1 | 11/2007 | Holm et al. |

(56) References Cited

U.S. PATENT DOCUMENTS

| | | |
|---|---|---|
| 2007/0276487 A1 | 11/2007 | Carteron |
| 2007/0280986 A1 | 12/2007 | Gil et al. |
| 2007/0286891 A1 | 12/2007 | Kettlewell et al. |
| 2007/0299538 A1 | 12/2007 | Roeber |
| 2008/0016037 A1 | 1/2008 | Enomoto et al. |
| 2008/0038307 A1 | 2/2008 | Hoffmann |
| 2008/0044481 A1 | 2/2008 | Harel |
| 2008/0045557 A1 | 2/2008 | Grainger et al. |
| 2008/0071385 A1 | 3/2008 | Binette et al. |
| 2008/0086216 A1 | 4/2008 | Wilson et al. |
| 2008/0109017 A1 | 5/2008 | Herweck et al. |
| 2008/0113001 A1 | 5/2008 | Herweck et al. |
| 2008/0118550 A1 | 5/2008 | Martakos et al. |
| 2008/0160307 A1 | 7/2008 | Bauchet et al. |
| 2008/0206305 A1 | 8/2008 | Herweck et al. |
| 2008/0207756 A1 | 8/2008 | Herweck et al. |
| 2008/0279929 A1 | 11/2008 | Devane et al. |
| 2008/0286440 A1 | 11/2008 | Scheer |
| 2008/0289300 A1 | 11/2008 | Gottlieb et al. |
| 2009/0011116 A1 | 1/2009 | Herweck et al. |
| 2009/0036996 A1 | 2/2009 | Roeber |
| 2009/0047414 A1 | 2/2009 | Corbeil et al. |
| 2009/0082864 A1 | 3/2009 | Chen |
| 2009/0092665 A1 | 4/2009 | Mitra et al. |
| 2009/0099651 A1 | 4/2009 | Hakimi-Mehr et al. |
| 2009/0181074 A1 | 7/2009 | Makower et al. |
| 2009/0181937 A1 | 7/2009 | Faucher et al. |
| 2009/0186081 A1 | 7/2009 | Holm et al. |
| 2009/0208552 A1 | 8/2009 | Faucher et al. |
| 2009/0226601 A1 | 9/2009 | Zhong |
| 2009/0240288 A1 | 9/2009 | Guetty |
| 2009/0259235 A1 | 10/2009 | Doucet et al. |
| 2009/0270999 A1 | 10/2009 | Brown |
| 2010/0183697 A1 | 7/2010 | Swanick et al. |
| 2010/0209473 A1 | 8/2010 | Dhont et al. |
| 2010/0233232 A1 | 9/2010 | Swanick et al. |
| 2010/0318108 A1 | 12/2010 | Datta et al. |
| 2011/0028412 A1 | 2/2011 | Cappello et al. |
| 2011/0045050 A1 | 2/2011 | Elbayoumi et al. |
| 2011/0144667 A1 | 6/2011 | Horton et al. |
| 2011/0213302 A1 | 9/2011 | Herweck et al. |
| 2011/0274823 A1 | 11/2011 | Labrecque et al. |
| 2012/0016038 A1 | 1/2012 | Faucher et al. |
| 2012/0213839 A1 | 8/2012 | Faucher et al. |
| 2012/0259348 A1 | 10/2012 | Paul |
| 2012/0315219 A1 | 12/2012 | Labrecque et al. |
| 2013/0041004 A1 | 2/2013 | Drager et al. |
| 2013/0084243 A1 | 4/2013 | Goetsch et al. |
| 2013/0096073 A1 | 4/2013 | Sidelman |

FOREIGN PATENT DOCUMENTS

| | | |
|---|---|---|
| CN | 101448474 | 6/2009 |
| CN | 102256565 | 11/2011 |
| DE | 19916086 | 10/1999 |
| DE | 10115740 | 10/2002 |
| EP | 0471566 | 2/1992 |
| EP | 610731 A1 | 8/1994 |
| EP | 0623354 | 11/1994 |
| EP | 0730864 | 9/1996 |
| EP | 0790822 | 8/1997 |
| EP | 0655222 | 6/1998 |
| EP | 0873133 | 10/1998 |
| EP | 0917561 | 5/1999 |
| EP | 0950386 | 10/1999 |
| EP | 1132058 | 9/2001 |
| EP | 1140243 | 10/2001 |
| EP | 1181943 | 2/2002 |
| EP | 1219265 | 1/2003 |
| EP | 1270024 | 1/2003 |
| EP | 1273314 | 1/2003 |
| EP | 1364628 | 11/2003 |
| EP | 1402906 A1 | 3/2004 |
| EP | 1520795 | 4/2005 |
| EP | 1557183 | 7/2005 |
| EP | 1576970 | 9/2005 |
| EP | 1718347 | 11/2006 |
| EP | 1952807 A1 | 8/2008 |
| EP | 2083875 | 8/2009 |
| EP | 2201965 | 6/2010 |
| EP | 2083875 | 3/2013 |
| GB | 2363572 | 1/2002 |
| JP | 49-50124 | 5/1974 |
| JP | 61-291520 | 12/1986 |
| JP | 1-175864 | 7/1989 |
| JP | 1-503296 | 9/1989 |
| JP | 3-224297 | 9/1996 |
| JP | 2001-10958 | 1/2001 |
| JP | 2006512140 | 4/2006 |
| JP | 2008155014 | 7/2008 |
| JP | 2012505025 | 3/2012 |
| JP | 2012505030 | 3/2012 |
| JP | 2013508033 | 3/2013 |
| KR | 20080025986 | 3/2008 |
| RU | 2125887 | 2/1999 |
| SU | 1297865 | 3/1987 |
| WO | 36000912 A1 | 2/1986 |
| WO | 87/06463 | 11/1987 |
| WO | 1990/001969 | 3/1990 |
| WO | 1990008544 | 8/1990 |
| WO | 93/21912 | 11/1993 |
| WO | 95/17901 | 7/1995 |
| WO | 1995/026715 | 10/1995 |
| WO | 96/18417 | 6/1996 |
| WO | 1996/041588 | 12/1996 |
| WO | 1997/002042 | 1/1997 |
| WO | 1997/009367 | 3/1997 |
| WO | 1997/013528 | 4/1997 |
| WO | 98/23228 | 6/1998 |
| WO | 1998/030206 | 7/1998 |
| WO | 3846287 A2 | 10/1998 |
| WO | 1998/054275 | 12/1998 |
| WO | 9908544 | 2/1999 |
| WO | 1999/025336 | 5/1999 |
| WO | 99/27989 | 6/1999 |
| WO | 99/40874 | 8/1999 |
| WO | 1999/56664 | 11/1999 |
| WO | 00/12147 | 3/2000 |
| WO | 00/40236 | 7/2000 |
| WO | 200040278 | 7/2000 |
| WO | 00/53212 | 9/2000 |
| WO | 200062830 | 10/2000 |
| WO | 01/15764 | 3/2001 |
| WO | 2001/024866 | 4/2001 |
| WO | 2001/026585 | 4/2001 |
| WO | 2001/037808 | 5/2001 |
| WO | 01/45763 | 6/2001 |
| WO | 2001/060586 | 8/2001 |
| WO | 2001/066036 | 9/2001 |
| WO | 2001/076649 | 10/2001 |
| WO | 2001/085060 | 11/2001 |
| WO | 02/22199 | 3/2002 |
| WO | 2002/22047 | 3/2002 |
| WO | 2002/049535 | 6/2002 |
| WO | 02/076509 | 10/2002 |
| WO | 2002100455 | 12/2002 |
| WO | 2003000308 | 1/2003 |
| WO | 2003/015748 | 2/2003 |
| WO | 2003/028622 | 4/2003 |
| WO | 2003/037397 | 5/2003 |
| WO | 2003/037398 | 5/2003 |
| WO | 2003/039612 | 5/2003 |
| WO | 2003/041756 | 5/2003 |
| WO | 03039612 A1 | 5/2003 |
| WO | 2003/070125 | 8/2003 |
| WO | 2003/073960 | 9/2003 |
| WO | 2003/092741 | 11/2003 |
| WO | 2003/092779 | 11/2003 |
| WO | 2003/094787 | 11/2003 |
| WO | 2003/105727 | 12/2003 |
| WO | 2004/004598 | 1/2004 |
| WO | 2004/006976 | 1/2004 |
| WO | 2004/006978 | 1/2004 |
| WO | 04/028610 | 4/2004 |

(56) References Cited

FOREIGN PATENT DOCUMENTS

| | | |
|---|---|---|
| WO | 2004/028582 | 4/2004 |
| WO | 2004/028583 | 4/2004 |
| WO | 04091684 | 10/2004 |
| WO | 2004101010 A1 | 11/2004 |
| WO | 2005/000165 | 1/2005 |
| WO | 2005/016400 | 2/2005 |
| WO | 2005/053767 | 6/2005 |
| WO | 2005/073091 | 8/2005 |
| WO | 2005082434 A2 | 9/2005 |
| WO | 2005116118 | 12/2005 |
| WO | 2006/024488 | 3/2006 |
| WO | 2006/036967 | 4/2006 |
| WO | 2006/032812 | 6/2006 |
| WO | 2006/102374 | 9/2006 |
| WO | 2007047028 | 4/2007 |
| WO | 2007047781 | 4/2007 |
| WO | 2008010788 | 1/2008 |
| WO | 2008016664 | 2/2008 |
| WO | 2008039308 | 4/2008 |
| WO | 08057328 | 5/2008 |
| WO | 2009/091900 A1 | 7/2009 |
| WO | 2009091900 A1 | 7/2009 |
| WO | 2010/042241 A1 | 4/2010 |
| WO | 2010042134 | 4/2010 |
| WO | 2010042241 | 4/2010 |
| WO | 2012009707 | 1/2012 |

OTHER PUBLICATIONS

Carbonell et al., "The susceptibility of prosthetic biomaterials to infection", Surgical Endoscopy. 19:430-435(2005).
Arciola et al., "Strong biofilm production, antibiotic multi-resistance and high gelE expression in epidemic clones of Enterococcus faecalis from orthopaedic implant infections", Biomaterials. 29:580-586(2008).
Extended European Search Report issued for EP Patent Application No. 10808706.5, dated Oct. 25, 2013, 4 pages.
Ralph L. Shriner et al., "The Systematic Identification of Organic Compounds—a laboratory manual", pp. 284 and 285, 6th ed. (John Wiley & Sons—1980).
Wei Wang et al., "Directing Oleate Stabilized Silver Colloids into Organic Phases", Langmuir, vol. 14, No. 3, (1998), pp. 602-610.
Genzyme Corporation, 510(k) Notification, Section 10: 510(k) Summary, Dec. 21, 1999, 11 pages.
Deeken, Corey R., et al., A review of the composition, characteristics, and effectiveness of barrier mesh prostheses utilized for laparoscopic ventral hernia repair, Surg Endosc, 2011, 10 pages.
"What are Omega-9 Fats?", Paleo Leap, LLC, printed from http://paleoleap.com/omega-9-fats on Sep. 14, 2016, 5 pages.
Kumar, Ashavani, et al., "Silver-nanoparticle-embedded antimicrobial paints based on vegetable oil", Nature Materials, vol. 7, Mar. 2008, pp. 236-241.
Shriner, Ralph L., et al., "The Systematic Identification of Organic Compounds—a laboratory manual", pp. 284 and 285, 6th ed. (John Wiley & Sons—1980).
Olive Oil Reference Book (PerkinElmer, Inc. 2012), pp. 1-48.
Standard for Olive Oils and Olive Pomace Oils, Codex Stan 33/1981 (World Health Organization 2013), pp. 1-9.
Wang, Wei, et al., "Directing Oleate Stabilized Nanosized Silver Colloids into Organic Phases", Langmuir, vol. 14, No. 3, (1998), pp. 602-610.
Cheong et al., "Peritoneal healing and adhesion formation/reformation", Human Reproduction Update. 7(6):556-566 (2001).
Carbonell et al., "The susceptibility of prosthetic biomaterials to infection", Surgical Endoscopy. 19:430-435(2005)(abstract).
Kuijer et al., "Assessing infection risk in implanted tissue-engineered devices", Biomaterials. 28:5148-5154 (2007).
Arciola et al., "Strong biofilm production, antibiotic multi-resistance and high gelE expression in epidemic clones of Enterococcus faecalis from orthopaedic implant infections", Biomaterials. 29:580-586(2008)(abstract).

Zheng et al., "Fatty acid synthesis is a target for antibacterial activity of unsaturated fatty acids", FEBS Letters, Elsevier, Amsterdam, NL, vol. 579, No. 23, Sep. 26, 2005, pp. 5157-5162.
Lee, Ji-Young et al., "Antimicrobial Synergistic Effect of Linolenic Acid and Monoglyceride against Bacillus cereus and Staphylococcus aureus", Journal of Agricultural and Food Chemistry, vol. 50, No. 7, Mar. 1, 2002, pp. 2193-2199.
Larsen, D. et al.., "Effect of cooking method on the fatty acid profile of New Zealand King Salmon (Oncorhynchus tshawytscha)" Food Chemistry 119 (2010) 785-790 (Year: 2010).
Steiner, M. et al. " Effect of Local Processing Methods (Cooking, Frying and Smoking) on Three Fish Species from Ghana: Part I. Proximate Composition, Fatty Acids, Minerals, Trace Elements and Vitamins" Food Chemistry 40 (1991) 309-321 (Year: 1991).
Gruger, Jr. E.H. Fatty Acid Composition. NMFS Scientific Publications by BOFC Fisheries. (http://spo.nmfs.noaa.gov/Circulars/CIRC276.pdf) 1967, pp. 1-30 (Year: 1967).
"Scientific Opinion on Fish Oil for Human consumption. Food Hygiene, including Rancidity", EFSA Journal—pp. 1-48, vol. 8, (2010).
"Gas Chromatography Theory"—updated Apr. 1, 2016—http://www.chem.ucia.edu/%7Ebacher/General/30BL/gc/theory.html.
Lehotay, Steven J., et al., "Application of Gas Chromatography in Food Analysis", Trends in Analytical Chemistry—pp. 686-697, vol. 21, (2002).
Edible Oils. (http://www.chempro.in/fallyacid.htm) accessed Apr. 14, 2014.
Malayoglu et al. "Dietary vitamin E ($\alpha$-tocopheryl acetate) and organic selenium supplementation: performance and antioxidant status of broilers fed n-3 PUFA-enriched feeds" South African Journal of Animal Science 2009, 39 (4), pp. 274-285 (Year: 2009).
Therapeutic definition (http://www.thefreedictionary.com/therapeutic) accessed Apr. 29, 2016.
Viscosity (http://www.vp-scientific.com/pdfs/www.liquidcontrol.com.eToolbox_viscosity.pdf) accessed Jan. 6, 2017, p. 1-4.
Hogg, Ronald J., et al., Clinical Trial to Evaluate Omega-3 Fatty Acids and Alternate Day Prednisone in Patients with IgA Nephropathy: Report from the Southwest Pediatric Nephrology Study Group, Clin J Am Soc Nephrol 1, Apr. 12, 2006, 467-474.
Bruno, Gene, Omega-3 Fatty Acids, Literature Education Series on Dietary Supplements, 2009, 1-4, Huntington college of Health Sciences, Knoxville, TN, US.
Mateo, R. D., et al., Effect of dietary supplementation of n-3 fatty acids and elevated concentrations of dietary protein on the performance of sows, J. Anim. Sci., 2009, 948-959, 87.
Non-Final Office Action issued in U.S. Appl. No. 16/165,628, dated Oct. 28, 2019.
Notice of Allowance issued in U.S. Appl. No. 15/841,993, dated Oct. 30, 2019.
Non-Final Office Action for U.S. Appl. No. 12/581,582 (listed on SB-08 as US 2010/0183697), dated Mar. 14, 2012.
Non-Final Office Action for U.S. Appl. No. 13/184,512 (listed on SB-08 as US 2012-0016038), dated Jan. 31, 2013.
Non-Final Office Action for U.S. Appl. No. 13/404,487 (listed on SB-08 as US 2012-0213839), dated Dec. 20, 2012.
Non-Final Office Action for U.S. Appl. No. 13/593,656 (listed on SB-08 as U.S. Publication No. US-2012-03115219) dated Jul. 15, 2013.
Non-Final Office Action for U.S. Appl. No. 13/682,991 (listed on SB-08 as US 2013-0074452), dated Mar. 18, 2013.
Non-final Office Action for U.S. Appl. No. 11/238,554 (listed on SB/08 as US 2006/0121081), dated Jul. 25, 2008.
Non-final Office Action for U.S. Appl. No. 11/582,135 (listed on SB/08 as US 2007/0202149), dated Jan. 6, 2010.
Non-final Office Action for U.S. Appl. No. 11/236,908 (listed on SB/08 as US 2006/0067974), dated Aug. 24, 2009.
Non-Final Office Action for U.S. Appl. No. 11/236,943 (listed on SB/08 as US 2006/0067975), dated Mar. 5, 2009.
Non-final Office Action for U.S. Appl. No. 11/236,977 (listed on SB/08 as US 2006/0088596), dated Aug. 3, 2009.
Non-final Office Action for U.S. Appl. No. 11/237,263 (listed on SB/08 as US 2006/0110457), dated Oct. 7, 2009.

(56) References Cited

OTHER PUBLICATIONS

Non-final Office Action for U.S. Application No. 11/237,264 (listed on Sb/08 as US 2006/0067983, atty. docket no. Amc-449-101), mailed Oct. 5, 2009.
Non-final Office Action for U.S. Application No. 11/238,532 (listed on Sb/08 as US 2006/0067976, atty. docket no. Ata-447), mailed Mar. 30, 2009.
Non-final Office Action for U.S. Application No. 11/238,554 (listed on Sb/08 as US 2006/0121081, atty. docket no. Amc-442-101), mailed Oct. 9, 2009.
Non-final Office Action for U.S. Application No. 11/238,564 (listed on Sb/08 as US 2006/0083768, atty. docket no. Ata-444), mailed Apr. 16, 2008.
Non-final Office Action for U.S. Application No. 11/239,555 (listed on Sb/08 as US 2006/0067977, atty. docket no. Ata-455), mailed Mar. 30, 2009.
Non-final Office Action for U.S. Application No. 11/525,328 (listed on Sb/08 as US 2007/0084144, atty. docket no. Ata-457), mailed Apr. 30, 2007.
Non-final Office Action for U.S. Application No. 11/525,390 (listed on Sb/08 as US 2007/0071798, atty. docket no. Amc-449-102), mailed Jul. 11, 201t.
Non-final Office Action for U.S. Application No. 11/525,390 (listed on Sb/08 as US 2007/0071798, atty. docket no. Amc-449-102), mailed Jul. 14, 2010.
Non-final Office Action for U.S. Application No. 11/582,135 (listed on Sb/08 as US 2007/0202149, atty. docket no. Amc-453-101), mailed Nov. 9, 2010.
Non-final Office Action for U.S. Application No. 11/582,135 (listed on Sb/08 as US 2007/0202149, atty. docket no. Amc-453-101), mailed May 12, 2009.
Non-Final Office Action for U.S. Application No. 11/701, 799 (listed on Sb/08 as US 2008/0109017, atty docket no. Amc-499-101), mailed Aug. 17, 201t.
Non-final Office Action for U.S. Appl. No. 11/701,799 (listed on SB/08 as US 2008/0109017), dated Apr. 12, 2010.
Non-final Office Action for U.S. Appl. No. 11/978,840 (listed on SB/08 as US 2008/0118550), dated Dec. 3, 2010.
Non-final Office Action for U.S. Appl. No. 11/980,155 (listed on SB/08 as US 2008/0113001), dated Mar. 24, 2011.
Non-final Office Action for U.S. Appl. No. 12/075,223 (listed on SB/08 as US 2008/0206305), dated Dec. 8, 2010.
Non-final Office Action for U.S. Appl. No. 12/325,546 (listed on SB/08 as US 2009/0181937), dated Feb. 25, 2010.
Non-final Office Action for U.S. Appl. No. 12/364,763 (listed on SB/08 as US 2009/0208552), dated Dec. 11, 2009.
Non-Final Office Action issued in U.S. Appl. No. 12/539,282, dated Aug. 31, 2011.
Non-Final Office Action issued in U.S. Appl. No. 12/539,282, dated May 29, 2013.
Non-Final Office Action issued in U.S. Appl. No. 11/701,799, dated Jul. 22, 2014.
Non-Final Office Action issued in U.S. Appl. No. 11/980,155, dated Nov. 12, 2013.
Non-Final Office Action issued in U.S. Appl. No. 11/980,155, dated Nov. 7, 2014.
Non-Final Office Action issued in U.S. Appl. No. 12/325,546, dated Apr. 22, 2014.
Non-Final Office Action issued in U.S. Appl. No. 12/364,763, dated Apr. 23, 2014.
Non-Final Office Action issued in U.S. Appl. No. 12/581,582, dated May 29, 2014.
Non-Final Office Action issued in U.S. Appl. No. 13/184,512, dated Oct. 10, 2014.
Non-Final Office Action issued in U.S. Appl. No. 13/943,489, dated Jul. 1, 2014.
Non-Final Office Action for U.S. Appl. No. 12/182,165 (listed on SB/08 as US 2009/0011116), dated Jan. 5, 2012.
Notice of Allowance for U.S. Appl. No. 11/582,135 (listed on SB/08 as US 2007/0202149), dated Jan. 9, 2012.
Notice of Allowance for U.S. Appl. No. 11/236,908 (listed on SB-08 as US 2006/0067974), dated May 11, 2012.
Notice of Allowance for U.S. Appl. No. 11/525,390 (listed on SB/08 as U.S. Publication No. US-2007/0071798), dated Nov. 20, 2012.
Notice of Allowance for U.S. Appl. No. 11/525390 (listed on SB/08 as US-2007/0071798), dated Oct. 4, 2012.
Notice of Allowance for U.S. Appl. No. 12/182,261 (listed on SB-08 as US 2009/0047414), dated Jul. 23, 2012.
Notice of Allowance for U.S. Appl. No. 13/404,487 (listed on SB-08 as US 2012-0123839), dated Apr. 2, 2013.
Notice of Allowance issued in U.S. Appl. No. 11/236,943, dated Oct. 6, 2014.
Notice of Allowance issued in U.S. Appl. No. 11/237,263, dated Mar. 27, 2014.
Notice of Allowance issued in U.S. Appl. No. 11/237,264, dated Mar. 27, 2014.
Notice of Allowance issued in U.S. Appl. No. 11/978,840, dated Aug. 6, 2013.
Notice of Allowance issued in U.S. Appl. No. 12/325,546, dated Dec. 8, 2014.
Notice of Allowance issued in U.S. Appl. No. 12/364,763, dated Dec. 5, 2014.
Notice of Allowance issued in U.S. Appl. No. 13/593,656, dated Jan. 24, 2014.
Notice of Allowance issued in U.S. Appl. No. 13/682,991, dated Aug. 1, 2013.
Notice of Allowance issued in U.S. Appl. No. 13/943,489, dated Jan. 29, 2015.
Novavax, retrieved online at http://www.novavax.com/go.cfm?do=Page.View&pid=3 (2006).
Novotny, L. et aL, Fish: a potential source of bacterial pathogens for human beings, Vet. Med.—Czech, 49, 2004, vol. 9, pp. 343-358.
Oberhoff, Martin et aL, "Local and Systemic Delivery of Low Molecular Weight Heparin Following PTCA: Acute Results and 6-Month Follow-Up of the Initial Clinical Experience With the Porous Balloon (Pilot-Study)," catheterization and Cardiovascular Diagnosis, 1998, vol. 44, pp. 267-274.
Office Action issued in EP Application No. 10808706.5 dated Aug. 30, 2016.
Office Action issued in EP Application No. 10808706.5 dated Jan. 29, 2016.
Office Action issued in EP Application No. 10808706.5 dated Sep. 1, 2017.
Ogunniyi, D.S., "Castor oil: A vital industrial raw material," Biosource Technology, vol. 97: 1086-1091 (2006).
Oliveira et al., Triglyceride Hydrolysis of Soy Oil vs Fish Oil Emulsions, Journal of Parenteral and Enteral Nutrition, 1997, 224-229, 21, 4.
Omega-3 DHA—The Problem May Be the Quality of Your Fish Oil, Not Your Allergy to Fish, Fatty Acids Hub, http://www.fattyacidshub.com/fatty-acids/omega-3-dha/ (downloaded Nov. 10, 2015).
Omegaven (http://medsafe.govt.nz/consumers/cmi/o/omegaven.pdf), downloaded Mar. 30, 2017.
Orthomolecular, Fish Oil, Jun. 29, 2004, http://orthomolecular.org/nutrients/fishoil.html, accessed Jul. 22, 2015, p. 1.
Orthovisc, "New Treatment Option is Potential Alternative to OTC Pain Medications for Osteoarthritis of the Knee" retrieved online at http://www.jnj.com/innovations/new_features/Orthovisc.htm:lessionid=33N2RBQDVODZKCQPCCEGU3AKB211WTT1 (2006).
Orthovisc, "Tools and Resources for Managing Your Osteoarthritis", retrieved online at http://www.orthovisc.com/ Khtmlbgdisplayptml?itemname=patient_resources (2007).
Orthovisc, "What is Orthovisc®?" retrieved online at http://www.orthovisc.com/xhtmlbgdisplayptml?temname=about_orthovisc (2005).
Orthovisc, "What to expect from your treatment," retrieved online at http://www.orthovisc.com/xhtmlbgdisplayptml?temname=what_to_expect (2007).
Orthovisc, "Your Knees and Osteoarthritis", retrieved online at http://www.orthovisc.com/xhtmlbgdisplayptml? temname=understanding_knee_oa (2003).
Oxford Reference, A Dictionary of Chemistry, 6th edition, John Daintith, 2008, 3 pages.

(56) References Cited

OTHER PUBLICATIONS

Petrovic, Z. S., Polymers from biological oils, Contemporary Materials, I-1, 2010, 39-50.
Pohibinska, A., et al., "Time to reconsider saline as the ideal rinsing solution during abdominal surgery", The American Journal of Surgery, vol. 192, pp. 281-222 (2007).
Polymer-Academic Press Dictionary of Science and TechnologyC. Morris (Ed.), Academic Press Dictionary of Science and Technology. Oxford, United Kingdom: Elsevier Science & Technology. Retrieved from http://search.credoreference.com/content/entry/apdst!polymer/O.
Polymer—The Chambers 21st Century Dictionary M. Robinson and G. Davidson (Eds.), London, United Kingdom: Chambers Harrap. Retrieved from http://search.credoreference.com/content/entry/chambdict!polymer/O.
Polymer, Encyclopedia Britannica. Encyclopedia Britannica Online, Encyclopedia Britannica Inc., 105, Web. Dec. 2, 2015, http://www.britannica.com/print/article/468696 (downloaded Dec. 2, 2015).
Polymers made from multiple monomers, A Natural Approach to Chemistry, Chapter 8, 241, http://lab-aids.com/assets/uploads/NAC/NAC_student_book/Texas%20Student%20Edition%20253.pdf (downloaded Dec. 3, 2015).
Redman, L.V. et al., "The drying rate of raw paint oils—a comparison," The Journal of Industrial and Engineering Chemistry, vol. 5: 630-636 (1913).
Refined soybean oil not an allergen, say food scientists, Food navigator-usa.com (2005), http://www.foodnavigator-usa.com/content/view/print/127438 (downloaded Nov. 10, 2015).
Rutkow, Ira M. et al., "'Tension-free' inguinal hemiorrhaphy: a preliminary report on the 'mesh plug' technique," Surgery, vol. 114:3-8 (1993).
S. Kamel et al., Pharmaceutical Significance of Cellulose: A Review, Express Polymer Letters vol. 2, No. 11, 2008, pp. 758-778.
Saghir et al., "Rapid in vivo hydrolysis of fatty acid ethyl esters, toxic nonoxidative ethanol metabolites", American Journal of Physiology, 1997, pp. G184-G190.
Sahni, Vasav, et al., A Review on Spider Silk Adhesion, The Journal of Adhesion, 2011, 595-614, 87.
Salu, Koen J. et al., "Addition of cytochalasin D to a biocompatible oil stent coating inhibits intimal hyperplasia in a porcine coronary model", Coronary Artery Disease, 2003, vol. 14, No. 8, pp. 545-555.
Sano, et al., "A controlled Trial of Selegiline, Alpha-Tocopherol, or Both as Treatment for Alzheimer's Disease", The New England Journal of Medicine, 336; 1216-1222 (1997).
Schardt, David, "Just the Flax: A "Miracle" Seed Comes Down to Earth", Nutrition Action Healthletter, Dec. 2005, pp. 7-9.
Scheller, Bruno et al., "Addition of Paclitaxel to Contrast Media Prevents Restenosis After Coronary Stent Implantation", Journal of the American College of Cardiology, 2003, vol. 42, No. 8, pp. 1415-1420.
SepraFilm Adhesion Barrier package insert (Genzyme Biosurgery 2008).
Shahidi, Fereidoon ed.; "Bailey's Industrial Oil and Fats Products" 2005: John Wiley and Sons; vol. 5, Edible Oil and Fat Products, Processing Technologies, pp. 1-15.
Sicherer, Scott H., Food Allergies: A Complete Guide for Eating When Your Life Depends on it, 2013, 15, Johns Hopkins University Press, Baltimore, MD, USA.
Singh, Alok, et al., "Facilitated Stent Delivery Using Applied Topical Lubrication", Catherization and Cardiovascular Interventions, vol. 69, pp. 218-222 (2007).
Soy Allergy, Asthma and Allergy Foundation of America (2005), http://www.aafa.org/display.cfm? id=9&sub=208,cont=522 (downloaded Nov. 10, 2015).
Soy allergy, at http://www.mayoclinic.org/diseases-conditions/soy-allergy/basics/definition/con-20031370?p=1 (downloaded Jul. 29, 2015).
Stenberg, Cecilia, "Influence of the fatty acid pattern on the drying of linseed oils", Akademisk Avhandling, 2004, 39 pages.
Supplementary ESR in AMC-427-EP1, dated Jul. 26, 2011.

Supplementary ESR in AMC-446-EP1 dated Aug. 18, 2011.
Supplementary ESR in AMC-448-EP1 dated Aug. 19, 2011.
Supplementary ESR in AMC-449-EP1 dated Jul. 27, 2011.
Supplementary European Search Report for Application No. EP 08877338.7, dated Aug. 16, 2012.
Supplementary European Search Report for Application No. EP 10825447, dated Mar. 31, 2014.
9.1 Terminology for Vegetable Oils and Animal Fats, at http://www.e-education.psu.edu/egee439/node/683 (downloaded Sep. 13, 2017), pp. 1-8.
Advisory Action of U.S. Appl. No. 11/238,554, dated Jul. 10, 2009.
Ali, Handbook of Industrial Chemistry: Organic Chemicals, Chapter 4, Edible Fats, Oils and Waxes, 1994, pp. 85-121.
American heritage desk dictionary, 198t p. 799, 2 pages.
Agualon: Sodium Carboxymethylcellulose: Physical and Chemical Properties, Hercules Incorporated, 1999, 30 pages.
Bard FDA 510K Approval (Jan. 2001).
Bard FDA 510K Approval (Jul. 2002).
Bellon et al., "Evaluation of a New Composite Prosthesis (PL-PU99) for the Repair of Abdominal Wall Defects in Terms of Behavior at the Peritoneal Interface," World Journal of Surgery, 26: 661-666 (2002).
Benchabane et al., Rheological properties of carboxymethyl cellulose (CMC) solutions, Colloid Polym Sci, 2008, 1173-1180, 286.
Bendavid et al., "A Femoral 'Umbrella' for Femoral Hernial Repair Surgery," Gynecology and Obstetrics, 165: 153-156 (1987).
Bendavid et al., "New Techniques in Hernia Repair," World Journal of Surgery, 13: 522-531 (1989).
Canter, Sheryl, "Chemistry of Cast Iron Seasoning: A Science-Based How-To," retrieved from sherylcanter.com on Apr. 5, 2013, pp. 1-5.
Clauss, Wolfram et al., "No Difference Among Modern Contract Media's Effect on Neointimal Proliferation and Restenosis After Coronary Stenting in Pigs," Investigative Reporting.
European Extended Search Report dated Jan. 18, 2016, issued for corresponding EP Patent Application No. 11807612.4, 7 pages.
CRC Handbook of Chemistry and Physics, 89th Edition, 2008-2009, Composition and Properties of Common Oils and Fats, pp. 7-9 to 7-13.
De Scheerder et al., "Experimental Study of Thrombogenicity and Foreign Body Reaction Induced by Heparin-Coated Coronary Stents," Circulation, 1997, vol. 95, pp. 1549-1553.
De Scheerder et al., "Local Angiopeptin Delivery Using Coated Stents Reduces Neointimal Proliferation in overstretched Porcine Coronary Arteries," J. Invasive Cardiol., 1995, vol. 8, pp. 215-222.
Drugs.com "Drug Index A to Z," retrieved on Apr. 1, 2013, pp. 1-4.
EP Office Action for EP Application No. 07838216.5, dated Feb. 11, 2010.
ESR for EP Application 05012112, dated Jul. 5, 2005.
ESR for EP Application 10157210, dated May 20, 2010.
European Communication for Application No. 07112611.4-2107, dated Nov. 30, 2007.
Extended European Search Report issued in EP Application No. 18000936.7 dated Jan. 7, 2020, 9 pages.
Fatty Acid Composition of Marine Oils by GLC, AOCS Official Method Ce 1b-89 (2009), pp. 1-7.
Fei, Bin, et al., "Hydrogel of Biodegradable Cellulose Derivatives. I. Radiation-Induced Crosslinking of Cmc", Journal of Applied Polymer Science, 2000, vol. 78, pp. 278-283.
Final OA for U.S. Appl. No. 11/140,811 dated Nov. 25, 2009.
Final Office Action for U.S. Appl. No. 11/250,768, dated Nov. 9, 2010.
Final Office Action issued in U.S. Appl. No. 16/165,628 dated Apr. 13, 2020, 9 pages.
Garner, Brian A., "A Dictionary of Modern Legal Usage," 2nd ed., 1987, pp. 389-390 and 713-717.
Gervajio "Fatty Acids and Derivatives from Coconut Oil." Baileys Industrial Oil and Fat Products, Sixth Edition. Ed. Sahandi. Hoboken: John Wiley & Sons, Inc. 2005 1-3.
Goodnight et al., "Polyunsaturated Fatty Acids, Hyperlipidemia, and Thrombosis," 1982, American Heart Association, Journal of the American Heart Association, vol. 2, No. 2, pp. 87-113.

(56) References Cited

OTHER PUBLICATIONS

Greenawalt et al., "Evaluation of Sepramesh Biosurgical Composite in a Rabbit Hernia Repair Model," Journal of Surgical Research, 94: 92-98 (2000).
Hawley's Condensed Chemical Dictionary—pp. 425 and 426 (2001), which corresponds to "Exhibit A1.".
Helfrich et al., "Abdominal Wall Hernia Repair: Use of the Gianturco-Helfrich-Eberhach Hernia Mesh," Journal of Laparoendoscopic Surgery, 5(2): 91-96 (1995).
Hercules Inc./Aqualon Div. CMC Quality Specifiction, Oct. 19, 2001 (Revised Sep. 2, 2008), 1 page.
Hoefler, Andrew C., "Sodium Carboxymethyl Cellulose: Chemistry, Functionality, and Applications", Hercules Incorporated, http://www.herc.com/foodgums/index.htm, 15 pages.
Hydrogenated Castor Oil, at http://www.acme-hardesty.com/product/hydrogenated-castor-oil/ (downloaded Jun. 2, 2017), which corresponds to "Exhibit B1.".
International Preliminary Report on Patentability for Application No. PCT/US08/71565, dated Apr. 5, 2010.
International Preliminary Report on Patentability for Application No. PCT/US08/85386, dated Apr. 12, 2011.
International Search Report for Application No. PCT/US10/048167, dated Oct. 20, 2010.
Interview summary for U.S. Appl. No. 11/237,420 (listed on SB08a as US 2006/0078586) dated May 5, 2009.
ISR for PCT/BE02/00166, dated Apr. 3, 2003.
John McMurray, Organic Chemistry, third edition, 1992, pp. 45-48.
Kaczynski, Jason, "Natural Omega3 Fish Oil Supplements—How to Avoid Synthetic Fish Oils," accessed online at http://ezinearticles.com/?Natural-Omega3-Fish-Oil-Supplements—How-to-Avoid-Synthetic-Fish-Oils&id=2460278, Jun. 10, 2009.
Kugel, et al., "Minimally invasive, Nonlaparoscopic, Preperitoneal, and Sutureless, Inguinal Herniorrhaphy," The American Journal of Surgery, 1999, vol. 178, pp. 298-302.
Lichtenstein, et al., "Repair of Recurrent Ventral Hernias by an Internal Binder," The American Journal of Surgery, 1976, vol. 132, pp. 121-125.
Luostarinen et al., "Vitamin E supplementation counteracts the fish oil induced increase of blood glucose in humans," Nutrition Research, vol. 15, No. 7, pp. 953-968, 1995.
Moreno et al., J. Agric. Food Chem., 2003, vol. 51, pp. 2216-2221.
Moreno-Egea, "Laparoscopic repair of Ventral and Incisional Hernias Using a new Composite Mesh (Parletex)," Surgical Laparoscopy, Endoscopy & Percutaneous Techniques, 2001, vol. 11, No. 2, pp. 103-106.
Supplementary European Search Report for Application No. EP09819594.4, dated Aug. 14, 2012.
Supplementary European Search Report for EP12004057, dated Apr. 10, 2011.
Supplementary European Search Report issued for EP Patent Application No. 10808706.5, dated Nov. 12, 2013.
Swanson, Danielle, et al., Omega-3 Fatty Acids EPA and DHA: Health Benefits Throughout Life, 3 Advances in Nutrition 1-7 (American Society for Nutrition 2012).
Szebeni et al., "Complement Activation by Cremophor EL as a Possible Contributor to Hypersensitivity to Paclitaxel: an in Vitro Study", Journal of the National Cancer Institute, 1998, vol. 90, No. 4, pp. 300-306.
Thomas Heinze, Carboxymethyl Ethers of Cellulose and Starch—A Review, Center of Excellence for Polysaccharide Research, Friedrich Schiller University of Jena (Germany), pp. 13-29, 2005.
Timar-Balzsy et al., Chemical Principles of Textile Conservation, Oxford: Elsevier Science Ltd., 1998, pp. 117-119.
Triglycerides, https://www.lipid.org/sites/default/files/triglycerides.pdf (downloaded Sep. 24, 2015).
Uchida, et al., "Swelling Process and Order-Disorder Transition of Hydrogel Containing Hydrophobic Ionizable Groups", Macromolecules, 28, 4583-4586 (1995).
Urakaze, Masaharu et al., "Infusion of fish oil emulsion: effects on platelet aggregation and fatty acid composition in phospholipids of plasma, platelets and red blood cell membranes in rabbits", Am. J. Clin. Nutr., vol. 46, pp. 936-940 (! 987).
Van Der Giessen, Willem J. et al., "Marked inflammatory Sequelae to Implantation of Biodegradable and Nonbiodegradable Polymers in Porcine Coronary Arteries", Circulation, 1996, vol. 94, pp. 1690-1697.
Wagner et al., Effects of tocopherols and their mixtures on the oxidative stability of olive oil and linseed oil under heating, European Journal of Lipid Science and Technology, 2000, 624-629, 102.
Websters Dictionary Online, Accessed on Feb. 13, 2009, entry for "polymer" p. 1 of 1.
Webster's II New College Dictionary (1995), 1075, Houghton Mifflin Company, New York, US.
Wexler et al. Chemical Reviews 1964 64(6):591-611.
Wicks et al. Organic Coatings:Science and Technology 1999 New York:Wiley Interscience p. 258-267.
Wikipedia, "Sirolimus", pp. 1-13, available online at http://en.wikipedia.org/wiki/sirolimus, accessed May 11, 2011.
Wikipedia, Sunflower oil, accessed Jul. 23, 2015, pp. 1-7.
Winter, et al., "Physical and Chemical Gelation" Encyclopedia of Materials—Science and Technology, vols. 1-11: 6691-6999 (2001).
Written Opinion issued in International Application No. PCT/US2010/045194, dated Sep. 24, 2010.
Yahyaee, R. et al., Waste fish oil biodiesel as a source of renewable fuel in Iran, Renewable and Sustainable Energy Reviews, 2013, pp. 312-319, 17, Elsevier Ltd.
"cure" in Academic Press Dictionary of Science and Technology, 1992.
"Evaluation of the Biocompatibility and Drug Delivery Capabilities of Biological Oil Based Stent Coatings", by Li, Shengqiao of the Katholieke Universiteit Leuven, 63 pages.
"Lead", Article by Centers for Disease Control and Prevention (CDC), Nov. 2009, 2 pages.
"polymerization", Merriam-Webster Online Dictionary, retrieved from www.merriam-webstercom on Dec. 13, 2009, p. 1.
A. M. Adel et al., Carboxymethylated Cellulose Hydrogel: Sorption Behavior and Characterization, Nature and Science, No. 8, vol. 8, 2010, pp. 244-256.
About.com, "Orthopedics, Synvisc injections," retrieved online at http://orthopedics.about.com/cs/treatment/a/synvisc_2.htm (2005).
Ackman, R.G., "Fish Oils", Bailey's Industrial Oil and Fat Products, 6th Edition, 279-317 (2005).
Advisory Action for U.S. Appl. No. 12/401,243 (listed on SB-08 as US 2010/0233232), dated Aug. 27, 2012.
Advisory Action for U.S. Appl. No. 12/581,582 (listed on SB-08 as U.S. Publication No. 2010-0183697), dated Nov. 14, 2012.
Ahuja et al., "Prevention of Postoperative Intraperitoneal Adhesions—An Experimental Study in Rats", Journal of Indian Pediatric Surgery 2002 7:15-20.
Alessandro Sannino et al., Biodegradeable Cellulose-based Hydrogels: Design and Applications, 2 Materials, pp. 353-373, 2009.
Allergies, Asthma and Allergy Foundation of America (2011), http://www.aafa.org/page/types-of-allergies,aspx (downloaded Oct. 5, 2015).
AMC-449-102, Herweck, et al. U.S. Pat. No. 8,367,099—US-2007-0071798, Mar. 29, 2007.
Andres, et al. "Antiproliferative Strategies for the Treatment of Vascular Proliferative Disease", Current Vascular Pharmacology, 1)1): 85-98 (2003).
Autosuture, "Parietex TM Composite Os Series Mesh", retrieved online at http://www.autosuture.com/AutoSuture/ pagebuilder.aspx?topicID=135734&breadcrumbs=135601:0 (2007).
Babev, Vladimir R., et al., Macrophage Lipoprotein Lipase Promotes Foam Cell Formation and Atherosclerosis in Vivo, 103 The Journal of Clinical Investigation, 1999, 1697-1705.
Bacteria in Water, The USGS Water Science School, http://water.usgs.gov/edu/bacteria.html (downloaded Nov. 9, 2015).
Bechert et al., "A New Method for Screening Anti-Infective Biomaterials", Nature Medicine. 6(8):1053-1056(2000).
Bimbo (Inform 1998 9(5):473-483.

(56) References Cited

OTHER PUBLICATIONS

Binder et al., "Chromatographic Analysis of Seed Oils. Fatty Acid Composition of Castor Oil", The Journal of American Oil Chemists' Society, 1962, vol. 39, pp. 513-517.
Biological evaluation of medical devices—Part 1: Evaluation and testing, International Standard ISO 109931-1, Aug. 1, 2003, Third Edition, Switzerland.
Birsan, et al., "The novel calcineurin inhibitor ISA247: a more potent immunosuppressant than cyclosporine in vitro", Transpl. Int., 2005, vol. 17, pp. 767-771.
Camurus, "In our endeavors to create the unique, we start with the best. Your product".
Cath Lab Digest, "Olive Oil Emulsion Helps With Problem Heart Arteries", retrieved online at http://www.cathlabdigest.com/displaynews.cfm?newsid=0103073 (2007).
Cecw-Ee, "Ch. 4: Coating Types and Characteristics", Engineering and Design—Painting: New Construction and Maintenance, 1995, pp. 4-1 to 4-24.
Champagne, Claude P., et al., "Microencapsulation for the improved delivery of bioactive compounds into foods", Current Opinion in Biotechnology, 2007, vol. 18, pp. 184-190.
EP Office Action dated Jul. 26, 2018 which issued during the prosecution of corresponding EP Patent Application No. 10808706.5, 4 pages.
Extended European Search Report dated Dec. 10, 2015 issued for EP Patent Application No. 13804477, 3 pages.
Extended European Search Report issued for EP Patent Application No. 10808706.5, dated Oct. 25, 2013, 1 pages.
Crivello et al., "Epoxidized triglycerides as renewable monomers in photoinitiated cationic polymerization", Chem. Mater. 1992, pp. 692-699.
de la Portilla, et al., "Prevention of Peritoneal Adhesions by Intraperitoneal Administration of Vitamin E: An Experimental Study in Rats", Diseases of the Colon and Rectum, 47; 2157-2161 (2005).
De Scheerder, Ivan K. et al., "Biocompatibility of polymer-coated oversized metallic stents implanted in normal porcine coronary arteries", Atherosclerosis, vol. 114, pp. 105-114.
Doctor's Guide to Medical and Other News, "AAOS Meeting: Synvisc Delays Total Knee Replacement in Osteoarthritis Patients", retrieved online at http://www.docguide.com/dg.nsf/PrintPrint/4585EC355198EEF08525670E006B10FF (1999).
Douglas, Kyle, et al., Zero-Order Controlled-Release Kinetics Through Polymer Matrices, available at http://www.drew.edu/wp-content/uploads/sites/99/Team5.pdf (dowloaded Dec. 21, 2016).
Drummond, Calum J. et al., "Surfactant self-assembly objects as novel drug delivery vehicles", Current Opinion in Colloid & Interface Science, 2000, vol. 4, pp. 449-456.
Drying Oil, http://en.wikipedia.org/wiki/drying_oil (downloaded Jun. 28, 2013).
Encyclopedia Britannica Online, "Surface Coating", available online at http://www.britannica.com/Ebchecked/topic/575029/surface-coating>, accessed Jun. 17, 2011.
Engstrom, Sven, "Drug Delivery from Cubic and Other Lipid-water Phases", Lipid Technology, 1990, vol. 2, No. 2, pp. 42-45.
Erhan, Sevim, et al., "Vegetable-oil-based printing ink formulation and degradation", Industrial Crops and Products 3, 1995, pp. 237-246.
Erhardt Paints Based on Drying Oil Media. Painted Wood: History & Conservation. Ed. Berland Singapore: The J. Paul Getty Trust 1998. p. 17-32.
Esoteric Oils, Peppermint essential oil information, accessed Jul. 23, 2015, pp. 1-7.
Evans, D.F., et al., Measurement of gastrointestinal pH profiles in normal ambulant human subjects, GUT, 1988,.1035-1041, 29.
F.D. Gunstone, Fatty Acid and Lipid Chemistry 72 (1999).
F.V.K Young, The Chemical & Physical Properties of Crude Fish Oils for Refiners and Hydrogenators, 18 Fish Oil Bulletin 1-18 (1986).
Falagas et al. European Society of Clinical Microbiology and Infection Diseases 2005 11:3-8.

Nagao et al., "Conjugated Fatty Acids in Food and Their Health Benefits," 2005, The Society for Biotechnology, Japan, Journal of Bioscience and Bioengineering, vol. 100, No. 2, pp. 152-157.
Nair et al. Journal of Dairy Science 2005 88:3488-3495.
Nakatsuji et al. Journal of Investigative Dermatology 2009 129(10): 2480-2488.
Non-Final OA for U.S. Appl. No. 11/140,811 dated Sep. 15, 2008.
Non-Final OA for U.S. Appl. No. 12/767,289 dated Aug. 19, 2011.
Non-Final OA for U.S. Appl. No. 12/767,289 dated Mar. 15, 2012.
Non-Final Office Action for U.S. Appl. No. 11/711,389, dated Dec. 17, 2010.
Non-Final Office Action for U.S. Appl. No. 12/401,228, dated Nov. 12, 2010.
Non-Final Office Action for U.S. Appl. 11/582,135 (listed on SB/08 as US-2007-0202149), dated Oct. 14, 2011.
Non-Final Office Action issued in U.S. Appl. No. 15/817,018, dated Feb. 6, 2020, 28 pages.
Non-Final Office Action issued in U.S. Appl. No. 16/213,823 dated Feb. 14, 2020, 14 pages.
Non-Final Office Action of U.S. Appl. No. 12/182,165, dated Jun. 24, 2013.
Non-Final Office Action of U.S. Appl. No. 13/185,135, dated Jan. 25, 2011.
Notice of Allowance for U.S. Appl. No. 11/525,390 (listed on SB/08 as US-2007/0071798), dated Nov. 30, 2012.
Notice of Allowance of U.S. Appl. No. 11/238,554, dated Apr. 28, 2011.
O'Neil, Maryadelle J. et al., The Merck Index—An Encyclopedia of Chemicals, Drugs, and Biologicals, 14th ed., 2006, entries for "Calcium Carbonate", "Cyclosporins", "Prussian Blue", and "Rapamycin", pp. 1-12.
Office Action issued in EP Application No. 10825447.5 dated Feb. 20, 2020, 4 pages.
Pandey et al. Tuberculosis 2005 85:227-234.
Pearlman, Daniel D. & Paul ft, "Guide to Rapid Revision," 3rd ed., 1982, Bobbs-Merrill Educational Publishing, pp. 25-27.
Pilz and Marz 2008, Free fatty acids as a cardiovascular risk factor. Clin Chem Lab Med, vol. 46, No. 4, pp. 429-434.
Preparation of Methyl Esters of Fatty Acids, AOCS Official Method Ce 2-66 (2009), pp. 1-2.
Rietjens et al., "The pro-oxidant chemistry of the natural antioxidants vitamin C, vitamin E, carotenoids, and lavonids," Environmental Toxicology and Pharmacology, 2002, vol. 11, pp. 321-333.
Salvolainen et al. International Journal of Pharmaceutics 2002 244:151-161.
Schwartz et al., "Restenosis and the Proportional Neointimal Response to Coronary Artery Injury: Results in a Porcine Model," J. Am. Coll. Cardiol., 1992, vol. 19, pp. 267-274.
Shakhashiri, Chemical of the week Fats and Oils, at www.scifun.org (last revised Jan. 30, 2008) 2 pages.
"Sharper Curve, Stronger Egg", Inside Science, printed Jan. 21, 2016, http://www.insidescience.org/content/sharper-curve-stronger-egg/779, 6 pages.
Sigma reference 2007.
Sigma-Aldrich, Polyhydroxy compounds webpage, captured May 28, 2009.
Sunflower Oil, at httpsllen.wikipedia.org/wiki/Sunflower_oil (downloaded Sep. 19, 2017, pp. 1-8.
Supplementary European Search Report for Application No. 05 80 2894, dated Jul. 27, 2011.
Supplementary European Search Report for Application No. 05 800 844, dated Aug. 19, 2011.
Supplementary European Search Report for EP Application No. 08782511, dated Apr. 23, 2013.
Sweetman, Sean C., "Martindale: The complete drug reference," 33rd ed., 2002, Pharmaceutical Press, pp. 1-90.
The Lipid Handbook, 2nd edision, 1994, Tocopherols, pp. 129-131.
Van Den Berg et al., Chemical changes in curing and ageing oil paints, ICOM Committee for Conservation, 1999, 248-253, vol. 1.
Wanasundara et al., "Effect of processing on constituents and oxidative stability of marine oils," Journal of Food Lipids, 1998, vol. 5, pp. 29-41.

(56) References Cited

OTHER PUBLICATIONS

Web article from http://www.buchi.com, "Slip Melting Point Determination of Palm Stearin", 1 page.
"What are hydrogenated fats?" at http://www.whfoods.comigenpage.php?tname=george&dbid=10 (downloaded Dec. 19, 2017), 3 pages.
International Search Report for International Application PCT/US05/034681, dated Jul. 26, 2006.
International Search Report for International Application PCT/US05/034682, dated Jul. 20, 2006.
International Search Report for International Application PCT/US05/034836, dated Jul. 6, 2006.
International Search Report for International Application PCT/US05/034941, dated May 4, 2006.
International Search Report for International Application PCT/US06/037184, dated Feb. 22, 2007.
International Search Report for International Application PCT/US06/040753, dated Sep. 24, 2007.
International Search Report for International Application PCT/US07/019978, dated May 7, 2009.
International Search Report for International Application PCT/US07/022860, dated Apr. 22, 2009.
International Search Report for International Application PCT/US07/022994, dated Apr. 3, 2009.
International Search Report for International Application PCT/US08/000565, dated May 4, 2009.
International Search Report for International Application PCT/US08/071547, dated Oct. 22, 2008.
International Search Report for International Application PCT/US08/071565, dated Nov. 10, 2008.
International Search Report for International Application PCT/US08/085386, dated Feb. 4, 2009.
International Search Report for International Application PCT/US09/037364, dated Aug. 27, 2009.
International Search Report for International Application PCT/US10/026521, dated Jun. 23, 2010.
International Search Report for International Application PCT/US10/052899, dated Jan. 10, 2011.
International Search Report for International Application PCT/US2013/044653, dated Sep. 4, 2013.
International Search Report for PCT/US2011/44292, dated Dec. 6, 2011.
Interview summary for U.S. Appl. No. 11/236,908 (listed on SB/08 as US 2006/0067974) dated Dec. 2, 2010.
Interview summary for U.S. Appl. No. 11/236,908 (listed on SB/08 as US 2006/0067974) dated May 5, 2009.
Interview summary for U.S. Appl. No. 11/582, 135 (listed on SB/08 as US 200710202149) dated Dec. 7, 2010.
Interview summary for U.S. Appl. No. 12/325,546 (listed on SB/08 as US 2009/0181937) dated Dec. 2, 2010.
Interview summary for U.S. Appl. No. 12/364,763 (listed on SB/08 as US 2009/0208552) dated Dec. 2, 2010.
Jonasson, Lena et al., "Cyclosporon a inhibits smooth muscle proliferation in the vascular response to injury," Proc. Natl. Acad. Sci. USA, vol. 85: 2303-2306 (1988).
Jorge, N., "Grasas y Aceites", 48(1): 17-24, (1997).
Kerns, Michelle, et al., "Adverse Reactions to Daily Fish Oil Tablets", SF Gate, http://healthyeating.sfgate.com/adverse-reactions-daily-fish-oil-tablets-8484.html, printed on Aug. 12, 2016, pp. 1-4.
Lewis, Richard J., Sr., Hawley's Condensed Chemical Dictionary, 2001, pp. 308, 309 and 896-898, 14th edision, John Niley & Sons, Inc., New York.
Lidar, M. et al., "Silicone and sclerodema revisited", Lupus, 2012, vol. 21, pp. 121-127.
Lipids, Chapter 19, pp. 1-12 (2002).
Luley et al., Fatty acid composition and degree of peroxidation in fish oil and cod liver oil preparations, Arzneimittelforschung. Dec. 1998, vol. 38, No. 12, pp. 1783-1786.
Mallegol, "Long-Term Behavior of Oil-Based Varnishes and Paints Photo-and Thermooxidation of Cured Linseed Oil", Journal of the American Oil Chemists' Society, 77:257-263 (2000).

Mallegol, Drier influence on the curing of linseed oil, Progress in Organic Coatings, Nov. 2000, vol. 39, No. 2, pp. 107-113.
Mayo Clinic (http://www.mayoclinic.org/drugs-supplements/omega-3-fatty-acids-fish-oil-alpha-linolenic-acids/safety/hrb-20059372?p=1 (downloaded Sep. 28, 2015).
Mayser et al., "n-3 Fatty Acids in psoriasis", British Journal of Nutrition, 2002, vol. 87, Suppl. 1, pp. S77-S82.
Methodist, "Evaluation of Biocompatibility and Antirestenotic Potential of Drug Eluting Stents Employing Polymer-free Highly-Hydrogenated Lipid-Based Stent Coatings in Porcine Coronary Arteries", Transcatheter Cardiovascular Therapeutics (TCT), sponsored by the Cardiovascular Research Foundation®, Oct. 22-27, 2006, Washington convention Center, Washington, D.C.
Milk allergy, at http://www.mayoclinic.org/diseases-conditions/milk-allergy/basics/definition/con-20032147?p=1 (downloaded Jul. 29, 2015).
Mills et al. Oils and Fats. "The Organic Chemistry of Museum Objects" London:Buttersworth and Co. 1987, pg. 26-40.
Morse, Molecular distillation of polymerized drying oils, Ind. Eng. Chem., 1941, No. 33, pp. 1039-1043.
Multanen, M., et al., Bacterial adherence to silver nitrate coated poly-L-lactic acid urological stents in vitro, Urol Res., Oct. 2000, 327-31, 5. (Abstract).
Neva L. Karrick, Nutritional Value of Fish Oils as Animal Feed, Circular 281 (Fish and Wildlife Service Bureau of Commercial Fisheries 1967), reprinted from M.E. Stansby (ed.), Fish Oils 362-382 (Avi Publishing Company 1967).
Non-Final Office Action for U.S. Appl. No. 12/182,261 (listed on SB/08 as US 2009/0047414), dated Dec. 21, 2011.
Non-Final Office Action for U.S. Appl. No. 11/236,908 (listed on SB/08 as US 2006/0067974), dated Dec. 2, 2011.
Non-final Office Action for U.S. Appl. No. 11/236,908 (listed on SB-08 as US 2006/0067974), dated Mar. 25, 2009.
Non-Final Office Action for U.S. Appl. No. 11/236,943 (listed on SB-08 as US 2006-0067975), dated Apr. 22, 2013.
Non-Final Office Action for U.S. Appl. No. 11/237,264 (listed on SB-08 as U.S. Publication No. US-2006-0067983) dated Jul. 3, 2013.
Non-Final Office Action for U.S. Appl. No. 11/582,135 (listed on SB/08 as US 2007/0202149), dated Oct. 14, 2011.
Non-Final Office Action for U.S. Appl. No. 11/978,840 (listed on SB-08 as US 2008-0118550), dated Feb. 19, 2013.
Non-Final Office Action for U.S. Appl. No. 12/401,243 (listed on SB/08) as US 2010/0233232), dated Jan. 5, 2012.
Fats & Oils (2008) at http://scifun.chem_wisc_edu/chemweek/pdf/fats&oils.pdf (downloaded Sep. 24, 2015).
Final Office Action for U.S. Appl. No. 11/236,908 (listed on SB-08 as US 2006/0067974), dated May 17, 2011.
Final Office Action for U.S. Appl. No. 11/701,799 (listed on SB-08 as US 2008-0109017), dated Feb. 13, 2012.
Final Office Action for U.S. Application 11/980,155 (listed on Sb/08 as US 2008/0113001, atty. docket no. Amc-490-101), mailed 10121/2011.
Final Office Action for U.S. Application 12/182,261 (listed on Sb-08 as US 2009/0047414, atty. docket no. Amc-484-102), mailed 04130/2012.
Final Office Action for U.S. Application 12/182,165 (listed on Sb-08 as US 2009-0011116, atty. Docket no. Amc-502-102), mailed Apr. 6, 2012.
Final Office Action for U.S. Application 12/401,243 (listed on Sb-08 as US 2010/0233232, atty. docket no. Amc-489-101), mailed Jun. 11, 2012.
Final Office Action for U.S. Application 12/581,582 (listed on Sb-08 as US 2010/0183697, atty. Docket no. Amc-519-102), mailed Aug. 29, 2012.
Final Office Action for U.S. Application No. 11/236,943 (listed on Sb/08 as US 200610067975, atty_ docket no. Amc-448-101), mailed Dec. 23, 2009.
Final Office Action for U.S. Application No. 11/237,263 (listed on Sb/08 as US 2006/0110457, atty_ docket no. Amc-446-101), mailed Juyl 7, 2010.

(56) References Cited

OTHER PUBLICATIONS

Final Office Action for U.S. Application No. 11/237,264 (listed on Sb/08 as US 2006l0067983, atty_ docket no. Amc-449-101), mailed Jun. 2, 2010.
Final Office Action for U.S. Application No. 11/238,532 (listed on Sb/08 as US 200610067976, atty_ docket no. Ata-447), mailed Sep. 9, 2009.
Final Office Action for U.S. Application No. 11/238,554 (listed on Sb/08 as US 2006/0121081, atty_ docket no. Amc-442-101), mailed May 1, 2009.
Final Office Action for U.S. Application No. 11/238,554 (listed on Sb/08 as US 2006/0121081, atty_ docket no. Amc-442-101), mailed May 12, 2010.
Final Office Action for U.S. Application No. 11/238,564 (listed on Sb/08 as US 2006/0083768, atty_ docket no. Ata-444), mailed Aug. 6, 2009.
Final Office Action for U.S. Application No. 11/525,390 (listed on Sb/08 as US 2007/0071798, atty_ docket no. Amc-449-102), mailed Apr. 21, 2011.
Final Office Action for U.S. Application No. 11/582,135 (listed on Sb/08 as US 2007/0202149, atty_ docket no. Amc-453-101), mailed May 12, 2011.
Final Office Action for U.S. Application No. 11/701, 799 (listed on Sb/08 as US 2008/0109017 atty_ docket no. Amc-499-101), mailed Nov. 23, 2010.
Final Office Action for U.S. Application No. 11/978,840 (listed on Sb/08 as US 2008/0118550. docket no. Amc-510-101), mailed Jun. 22, 2011.
Final Office Action for U.S. Application No. 12/075,223 (listed on Sb/08 as US 2008/0206305. docket no. Amc-496-102), mailed Aug. 11, 201t.
Final Office Action for U.S. Application No. 12/325,546 (listed on Sb/08 as US 2009/0181937. docket no. Amc-453-102), mailed Aug. 31, 2010.
Final Office Action for U.S. Application No. 12/364,763 (listed on Sb/08 as US 2009/0208552. docket no. Amc-453-103), mailed Sep. 21, 2010.
Final Office Action issued in U.S. Application No. 12/539,282, mailed Feb. 7, 2012 (Atri.84US01).
Final Office Action issued in U.S. Application No. 12/539,282, mailed Nov. 19, 2013 (Atri.84US01).
Final Office Action issued in US Application 11/236,943, dated Dec. 4, 2013 (Atri.64US01).
Final Office Action issued in U.S. Appl. No. 11/237,264, dated Dec. 17, 2013.
Final Office Action issued in U.S. Appl. No. 11/701,799, dated Mar. 12, 2015.
Final Office Action issued in U.S. Appl. No. 11/980,155, dated Jul. 21, 2014.
Final Office Action issued in U.S. Appl. No. 12/581,582, dated Jan. 8, 2015.
Fish Oil Triglycerides vs. Ethyl Esters: a Comparative Review of Absorption, Stability and Safety Concerns (Ascenta Health Ltd. 2010 at http://www.ascentaprofessional.comiscience/articlesifish-oil-triglycerides-vs-ethyl-esters :downloaded Sep. 24, 2015).
Garg et al., "Differential Effects of Dietary Linoleic and a-Linolenic Acid on Lipid Metabolism in Rat Tissues", Lipids, 1988, vol. 23, No. 9, pp. 847-852.
Guler et aL, "Some empirical equations for oxopolymerization of linseed oil", Progress in Organic Coatings, 2004, vol. 51, pp. 365-371.
Suffinger, et al., "Polyphenols in Olive Oils", Journal of the American Oil Chemists Society, 58(11): 966-968 (1981).
H. Fineberg et al., Industrial Use of Fish Oils, pp. 222-238, http://spo.nmfs.noaa.goviCirculars/CIRC278.pdf, lownloaded Aug. 3, 2015_.
H. Omidian, et aL, Swelling Agents and Devices in Oral Drug Delivery, J. Drug. Del. Sci. Tech., No. 18, vol. 2, 2008, pp. 83-93.
Hawley'S Condensed Chemical Dictionary 315, 316, 332, 333, 334, 825 and 826 (2001).
Henderson, R. James et al., "Hydrolysis of Fish Oils Containing Polymers of Triacylglycerols by Pancreatic Lipase in vitro", Lipids, vol. 28, No. 4, 1993, pp. 313-319.
Herbert O. Hultin et al., Chemical Composition and Stability of Fish Oil (International Association of Fish Vied Manufacturers Apr. 10, 1991).
Hortolam, Juliane G., et al., "Connective tissue diseases following silicone breast implantation: where do we stand?", Clinics, 2013, vol. 3, p. 281.
Hwang, Chao-Wei et al., "Physiological Transport Forces Govern Drug Distribution for Stent-Based Delivery", circulation, 2001, vol. 104, pp. 600-605.
International Preliminary Examination Report for International Application PCT/US08/071547, dated Aug. 26, 2010.
International Preliminary Report on Patentability for International Application PCT/US06/040753, dated Oct. 3, 2008.
International Preliminary Report on Patentability for International Application PCT/US08/071565, dated Aug. 27, 2009.
International Preliminary Report on Patentability issued in International Application No. PCT/US2010/045194, dated Feb. 23, 2012.
International Search Report for International Application No. PCT/US2010/045194, dated Sep. 24, 2010.
International Search Report for International Application PCT/US05/034601, dated Apr. 10, 2006.
International Search Report for International Application PCT/US05/034610, dated Mar. 16, 2006.
International Search Report for International Application PCT/US05/034614, dated Aug. 29, 2006.
International Search Report for International Application PCT/US05/034615, dated May 16, 2006.
International Search Report for International Application PCT/US05/034678, dated Aug. 28, 2006.
Office Action issued in Chinese Application No. 201610998395.8 dated Apr. 28, 2020, 14 pages.
Office Action issued in Chinese Application No. 201610997993.3 dated May 11, 2020, 7 pages.

* cited by examiner

ANTI-INFECTIVE ANTIMICROBIAL-CONTAINING BIOMATERIALS

CROSS-REFERENCE TO RELATED APPLICATIONS

This application claims priority to and is a continuation of co-pending U.S. patent application Ser. No. 12/539,282, filed Aug. 11, 2009, which patent application is incorporated herein by reference in its entirety.

BACKGROUND OF THE INVENTION

Implantable medical devices are indispensable in the ability to treat a variety of medical conditions in critically and chronically ill patients. Catheters can be used to deliver drugs or nutrients to a patient or to safely remove waste products. Stents can be used to open blocked coronary arteries and restore blood flow to the heart. Vascular grafts can also be used to restore blood flow in addition to providing easier access and improved treatment of a patient with kidney failure by dialysis. Hernia mesh devices allow for improved patient outcomes in the treatment of abdominal wounds by providing additional strength to the surgical repair.

One complication in the use of implantable medical devices is the risk of these devices becoming colonized with bacteria during surgical implantation (see, e.g., A. M. Carbonell et al. *Surg Endosc.* 2005; Vol. 19, pgs 430-435; T. Bechert et al. *Nature Medicine.* 2000; Vol. 6, No. 8, pgs 1053-1056; R. Kuijer et al. *Biomaterials.* 2007; Vol. 28, pgs 5148-5154; C. R. Arciola et al. *Biomaterials.* 2008; Vol. 29, pgs 580-586). Once a patient shows signs of device infection, the surgeon is often required to perform several additional surgical procedures to treat the device infection, such as drainage of the infection site and the local administration of antibiotics. In cases where the infection is not successfully resolved, the surgeon will be required to remove the device from the implanted surgical site until the infection is resolved with the treatment of oral and/or intravenous antibiotics to the patient. Thus, an infected medical device not only results in increasing medical costs, but also results in increased risk of morbidity and mortality to the patient (A. M. Carbonell et al., 2005; T. Bechert et al, 2000; R. Kuijer et al., 2007).

Another important aspect in the use of medical devices is the biological response to a medical device after surgical repair of an in-vivo injury (see, e.g., Y. C. Cheong et al. *Human Reproduction Update.* 2001; Vol. 7, No. 6, pgs 556-566). A typical biological response to the surgical site includes inflammation of native tissue followed by migration and proliferation of cells to mitigate the inflammatory response, including platelets and macrophages, and a subsequent healing phase that includes fibrin deposition and the formation of fibrin matrix followed by tissue remodeling. In the case of hernia repair, abnormal peritoneal healing can occur when there is the expression of inflammatory cytokines from macrophages (e.g., α-TNF) that can result in an inability of the fibrin matrix to be properly broken down and can result in the formation of adhesions (Y. C. Cheong et al., 2001). Abdominal adhesions formed after hernia repair can result in pain, bowel strangulation, infertility and in some cases death (Y. C. Cheong et al., 2001).

Accordingly, there remains a need for medical devices that have a reduced susceptibility to colonization by bacteria and other microorganisms, or other health complications, such as adhesions.

SUMMARY OF THE INVENTION

What is desired is a material (e.g., a device coating, gel or stand-alone film) that can be utilized to prevent or diminish chronic inflammation due to the hydrolysis products of the coating, as well as to reduce infection resulting from surgical implantation of medical devices. Furthermore, it is desirable that the material release and deliver therapeutic agents (e.g., an antimicrobial, e.g., an antibiotic agent) in a sustained and controlled fashion. When in the form of a stand alone film, such a device can be useful in wound healing applications.

Thus, provided herein is a composition comprising an antimicrobial agent, a fatty acid, and a glyceride, wherein the fatty acid and glyceride components are cross-linked. Such a composition can be referred to as an "antimicrobial agent-containing biomaterial." When the antimicrobial agent is a silver compound, the composition can be referred to as a "silver-containing biomaterial." This composition has both anti-inflammation and anti-infection properties, and can come in many forms, e.g., a coating for a medical device, a stand-alone film, a gel, a particle, or an emulsion. When the composition is a coating, it can be placed on the surface of a medical device in order to prevent bacterial colonization and infection. The antimicrobial-containing biomaterial can also be used to prevent tissue adhesion, as well as to facilitate general wound healing, when, e.g., in the form of a film.

In one aspect, provided herein is a composition comprising an antimicrobial compound, a fatty acid, and a glyceride, wherein the fatty acid and glyceride components are cross-linked. In one embodiment, the antimicrobial compound is a silver compound, and the silver compound is ionic silver or elemental silver. The silver can be elemental silver and is in the form of a silver nanoparticle. In another embodiment, the silver is ionic silver and is selected from the group consisting of silver nitrate, silver chloride, silver fluoride, silver bromide, silver oxide, silver sulfate, silver carbonate, silver cyanide, silver tetrafluoroborate, silver sulfide, silver acetate, silver lactate, silver benzoate, silver cyclohexanebutyrate, silver diethyldithiocarbamate, silver trifluoromethanesulfonate and mixtures thereof. In another embodiment, the silver is ionic silver and is selected from the group consisting of silver nitrate, silver acetate, silver oxide, and mixtures thereof.

In another embodiment, the antimicrobial compound is selected from the group consisting of diamidines, iodine and iodophors, peroxygens, phenols, bisphenols, halophenols, biguanides and silver compounds. In still another embodiment, the antimicrobial compound is selected from the group consisting of triclosan, chlorhexidine, triclocarban, hexachlorophene, dibromopropamidine, chloroxylenol, phenol and cresol.

In another embodiment, the antimicrobial compound is an antibiotic compound. The antibiotic compound can be selected from the group consisting of gentamicin sulfate, penicillin g, ephalothin, ampicillin, amoxicillin, augmentin, aztreonam, imipenem, streptomycin, gentamicin, vancomycin, clindamycin, erythromycin, azithromycin, polymyxin, bacitracin, amphotericin, nystatin, rifampicin, tetracycline, doxycycline, chloramphenicol, nalidixic acid, ciprofloxacin, sulfanilamide, gantrisin, trimethoprim, isoniazid, para-aminosalicylic acid, and minocycline.

In another embodiment of the biomaterial provided herein, the cross-linked fatty acid and glyceride are derived from oil containing at least one omega-3 fatty acid, such as fish oil.

In another embodiment, the antimicrobial-containing biomaterial contains an additional antimicrobial compound. The additional antimicrobial compound can be selected from the group consisting of diamidines, iodine and iodophors, peroxygens, phenols, bisphenols, halophenols, biguanides and silver compounds. In another embodiment, the additional antimicrobial compound is selected from the group consisting of elemental silver, silver nanoparticle, silver nitrate, silver chloride, silver fluoride, silver bromide, silver oxide, silver sulfate, silver carbonate, silver cyanide, silver tetrafluoroborate, silver sulfide, silver acetate, silver lactate, silver benzoate, silver cyclohexanebutyrate, silver diethyldithiocarbamate, silver trifluoromethanesulfonate, triclosan, chlorhexidine, triclocarban, hexachlorophene, dibromopamidine, chloroxylenol, phenol and cresol.

In still another embodiment, the antimicrobial-containing biomaterial contains an additional antibiotic compound. In one embodiment, the antibiotic compound is selected from the group consisting of gentamicin sulfate, penicillin g, ephalothin, ampicillin, amoxicillin, augmentin, aztreonam, imipenem, streptomycin, gentamicin, vancomycin, clindamycin, erythromycin, azithromycin, polymyxin, bacitracin, amphotericin, nystatin, rifampicin, tetracycline, doxycycline, chloramphenicol, nalidixic acid, ciprofloxacin, sulfanilamide, gantrisin, trimethoprim, isoniazid, para-aminosalicylic acid, and minocycline.

The antimicrobial-containing biomaterial composition provided herein can be further combined with an oil containing an omega-3 fatty acid. Examples of such oils include, but are not limited to, fish oil, olive oil, grape oil, palm oil, or flaxseed oil.

In another embodiment, when the biomaterial composition is associated with a tissue of a subject, the silver compound is released from the cross-linked fatty acid at a controlled release rate.

In another aspect, provided herein is a film comprising an antimicrobial compound, a fatty acid, and a glyceride, wherein the fatty acid and glyceride components are cross-linked.

The antimicrobial-containing biomaterial provided herein can be associated with a medical device, such as a bandage, a stent, a graft, a shunt, a catheter, a surgical mesh, or a balloon.

In another aspect, provided herein is a medical device at least partially coated with the antimicrobial-containing biomaterial provided herein. In one embodiment, the medical device is a bandage, a stent, a graft, a shunt, a catheter, or a balloon. In another embodiment, the mesh is a surgical mesh.

In another aspect, provided herein is a method of forming a composition comprising an antimicrobial compound and a cross-linked fatty acid, comprising:
curing a starting material comprising a fatty acid and a glyceride according to a first curing condition to form a second material; and associating the second material with an antimicrobial compound that is dissolved in a solution by immersing the second material in the antimicrobial compound solution or aerosolizing the antimicrobial compound solution onto the second material;
such that the composition is formed.

In one embodiment of this method, the fatty acid starting material is fish oil. In another embodiment, the antimicrobial is a silver compound, and the silver compound is selected from the group consisting of a silver nanoparticle, silver nitrate, silver chloride, silver fluoride, silver bromide, silver oxide, silver sulfate, silver carbonate, silver cyanide, silver tetrafluoroborate, silver sulfide, silver acetate, silver lactate, silver benzoate, silver cyclohexanebutyrate, silver diethyldithiocarbamate, silver trifluoromethanesulfonate and mixtures thereof. In another embodiment of the method, before curing the fatty acid starting material, the starting material is associated with a medical device, such as a bandage, a stent, a graft, a shunt, a catheter, or a balloon. In another embodiment, the composition is associated with a surgical mesh.

In another aspect, provided herein is a method of forming a composition comprising an antimicrobial compound and a cross-linked fatty acid, comprising:
curing a starting material comprising a fatty acid and a glyceride according to a first curing condition to form a second material;
associating the second material with a fatty acid-containing oil and an antimicrobial compound that is dissolved in a solution to form a third material; and
curing the third material according to a second curing condition;
such that the composition is formed.

In one embodiment of this method, a portion of the fatty acids of the second material are cross-linked. In still another embodiment, the fatty acid starting material and the fatty acid-containing oil are fish oil. In still another embodiment, the antimicrobial compound is a silver compound, and the silver compound is selected from the group consisting of a silver nanoparticle, silver nitrate, silver chloride, silver fluoride, silver bromide, silver oxide, silver sulfate, silver carbonate, silver cyanide, silver tetrafluoroborate, silver sulfide, silver acetate, silver lactate, silver benzoate, silver cyclohexanebutyrate, silver diethyldithiocarbamate, silver trifluoromethanesulfonate and mixtures thereof. In another embodiment of this method, before curing the third material, the third material is associated with a medical device, such as a bandage, a stent, a catheter, a surgical mesh, or a balloon.

In another aspect, provided herein is a method of forming a composition comprising an antimicrobial compound and a cross-linked fatty acid, comprising:
associating a fatty acid- and glyceride-containing oil with an antimicrobial compound to form a second material; and
curing the second material according to a first curing condition;
such that the antimicrobial-containing composition is formed.

In one embodiment of this method, the fatty acid-containing oil is a fish oil. In still another embodiment, the fatty acid- and glyceride-containing oil is a mixture of fish oil, and pre-cured fish oil. In another embodiment of this method, the antimicrobial compound is a silver compound, and the silver compound is ionic silver in aqueous solution. In still another embodiment, the antimicrobial compound is a silver compound, and the silver compound is in the form of a silver nanoparticle.

In yet another embodiment of this method, an additional antimicrobial compound is dissolved in solvent to form a third composition, and the third composition is coated onto the outer surface of the antimicrobial-containing composition. In one embodiment, the third composition is coated onto the outer surface of the antimicrobial-containing composition by spraying the third composition or submerging the antimicrobial-containing composition in the third composition. The additional compound can be an antimicrobial compound, and the antimicrobial compound is selected from the group consisting of diamidines, iodine and iodophors, peroxygens, phenols, bisphenols, halophenols, biguanides and silver compounds. In another embodiment, the additional antimicrobial compound, and the antimicrobial compound is selected from the group consisting of elemental silver, silver nanoparticle, silver nitrate, silver chloride, silver fluoride, silver bromide, silver oxide, silver sulfate, silver carbonate, silver cyanide, silver tetrafluoroborate, silver sulfide, silver acetate, silver lactate, silver benzoate, silver cyclohexanebutyrate, silver diethyldithiocarbamate, silver trifluoromethanesulfonate, triclosan, chlorhexidine, triclocarban, hexachlorophene, dibromopropamidine, chloroxylenol, phenol and cresol. In still another embodiment of this method, the additional compound is an antibiotic compound, and wherein the antibiotic compound is selected from the group consisting of gentamicin sulfate, penicillin g, ephalothin, ampicillin, amoxicillin, augmentin, aztreonam, imipenem, streptomycin, gentamicin, vancomycin, clindamycin, erythromycin, azithromycin, polymyxin, bacitracin, amphotericin, nystatin, rifampicin, tetracycline, doxycycline, chloramphenicol, nalidixic acid, ciprofloxacin, sulfanilamide, gantrisin, trimethoprim, isoniazid, para-aminosalicylic acid, and minocycline.

In another embodiment of this method, before curing the second material, the second material is associated with a medical device, such as a bandage, a stent, a catheter, a surgical mesh, or a balloon.

In another aspect, provided herein is a method of treating or preventing tissue adhesion in a subject in need thereof, comprising administering the subject the antimicrobial-containing biomaterial provided herein.

In another aspect, provided herein is a method of treating or preventing a bacterial infection in a subject in need thereof, comprising administering the subject the antimicrobial-containing biomaterial provided herein.

In another aspect, provided herein is an emulsion comprising an antimicrobial compound, a fatty acid, and a glyceride, wherein the fatty acid and glyceride components are cross-linked.

In another aspect, provided herein is a composition comprising a silver compound, a fatty acid, and a glyceride, wherein the fatty acid and glyceride components are cross-linked.

BRIEF DESCRIPTION OF THE DRAWINGS

The foregoing and other aspects, embodiments, objects, features and advantages of the invention can be more fully understood from the following description in conjunction with the accompanying drawings. In the drawings, like reference characters generally refer to like features and structural elements throughout the various figures. The drawings are not necessarily to scale, emphasis instead being placed upon illustrating the principles of the invention.

This includes various embodiments that are based on observed antimicrobial properties of medical articles augmented with fatty acid antimicrobial compositions containing various pharmaceutical and anti-infective agents. The examples set forth in this specification are not intended to be limiting and merely set forth some of the many possible embodiments of the claimed invention.

DETAILED DESCRIPTION

Figure 1:
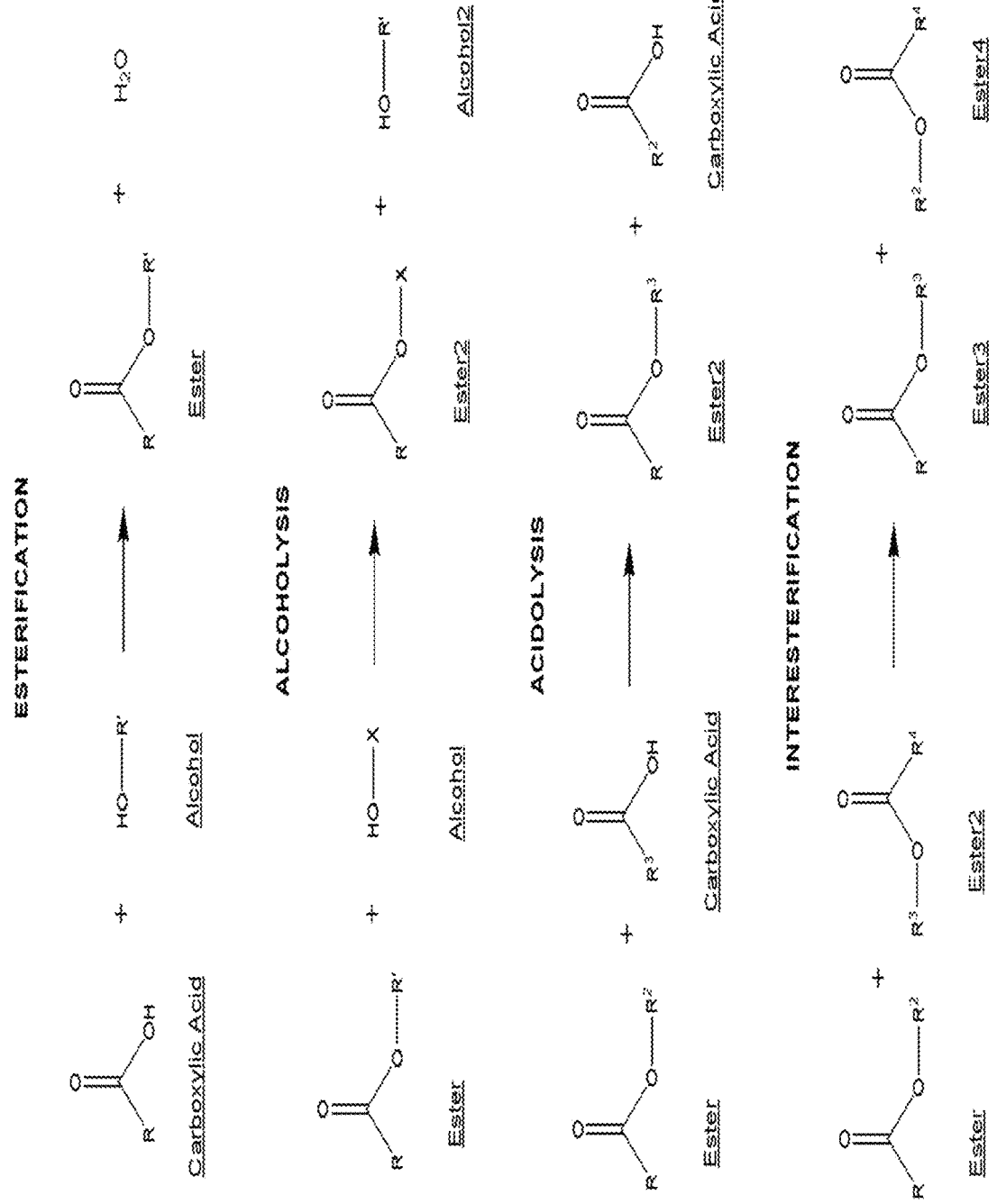
FIG. 1 is a schematic of reactions that result in the formation of ester bonds.

Implantable medical devices are designed to improve the quality of life of patients with varying medical conditions. These devices, however, are highly susceptible to infection and can affect patient mortality and morbidity leading to high medical costs. While such infection may occur during surgery, nosocomial infections are also associated with medical device infections which necessitate the use of antimicrobial compositions within or on the surface of these medical devices in order to prevent bacterial colonization and infection.

Provided herein is a biomaterial containing an antimicrobial compound (an "antimicrobial-containing biomaterial"). In one embodiment, the antimicrobial compound is a silver compound or triclosan. In another embodiment, the antimicrobial compound is an antibacterial compound, such as gentamicin. Embodiments of the present invention may provide a biomaterial containing a silver compound. The biomaterial can be made from a source of fatty acids and glycerides (e.g., an oil, e.g., a fish oil) that is cured to cross-link the fatty acids and glycerides. The biomaterial can be further combined with other antimicrobial agents such as, but not limited to, triclosan, chlorhexidine, gentamicin, gentamicin sulfate, and other antibiotics. One advantage of the present antimicrobial-containing biomaterial is the anti-inflammatory properties derived from the fatty acids, while providing a suitable vehicle for sustained controlled release of the antimicrobial (e.g., silver-based agents, triclosan, chlorhexidine, gentamicin, gentamicin sulfate, etc.). The antimicrobial-containing biomaterial furthermore provides a favorable surface for adding topical layers of additional antimicrobial agents that provide different sustained release and efficacy properties.

When associated with a medical device, the antimicrobial-containing biomaterial provided herein can reduce the incidence of inflammatory and foreign body responses after implantation of that medical device. The antimicrobial-containing biomaterial can also provide the release of one or more therapeutic agents (silver-based agents, triclosan, chlorhexidine, gentamicin, gentamicin sulfate, etc.) over a period of time in order to reduce the ability of bacteria to colonize during implantation and to prevent a device-related infection. The antimicrobial-containing biomaterial can also be used to prevent tissue adhesion, as well as to facilitate general wound healing. When in the form of a stand-alone film, or when associated with a bandage, the antimicrobial-containing biomaterial can be used in wound healing applications. The antimicrobial-containing biomaterial can also be metabolized via a bioabsorption mechanism.

The antimicrobial-containing biomaterial can be utilized alone or optionally in combination with a medical device for the release and local delivery of one or more antimicrobial agents to prevent colonization of bacteria onto the device during surgical implantation. Methods of forming and tailoring the properties of said biomaterials are also provided. Additionally, due to the unique properties of the underlying chemistry of the biomaterial, the biomaterial (e.g., coating or stand-alone film) contains specific chemical components that assist in reducing a foreign body response and inflammation at the site of tissue injury during implantation that improves its in-vivo performance.

Antimicrobial-Containing Fatty Acid-Derived Biomaterials

In various aspects, the antimicrobial-containing biomaterial can be, but is not limited to, a coating for a medical device, a stand-alone film, a gel, a particle, or an emulsion. The biomaterial can be a hydrophobic biomaterial comprising cross-linked fatty acids and glycerides. In various embodiments, the fatty acid/glyceride-derived biomaterial is non-polymeric. In certain instances, as described herein, the source of the fatty acid and glyceride is an oil, e.g., a fish oil. The oil can also be olive oil, grape oil, palm oil, or flaxseed oil. In such an instance, the antimicrobial-containing biomaterial can also be referred to as an "oil-derived antimicrobial-containing biomaterial" (e.g., an "oil-derived silver-containing biomaterial").

Various methods can be used to prepare the antimicrobial-containing biomaterial described herein. The fatty-acid and glyceride (e.g., oil, e.g., fish oil) can be cured (using heat, UV, etc.) to induce fatty-acid oxidation and crosslinking of a portion, majority, or all of the fatty acids and glycerides to form a gel. The antimicrobial component can be added to the fatty acid before, during, or after the curing process. In one embodiment, a pre-cure-derived biomaterial is combined with an antimicrobial compound to create the antimicrobial-containing biomaterial (e.g., coating or stand-alone film) described herein.

A "pre-cure" component refers to fatty acids (e.g., from fish oil) that are partially cured (using heat, UV, etc.) to induce an initial amount of fatty-acid oxidation and cross-linking to form a viscous fatty acid-derived gel. The pre-cured fatty acid component (when the source of the fatty acid is an oil, such as fish oil, the component can also be referred to as "pre-cured oil") can be combined with an antimicrobial compound, wherein the antimicrobial compound is optionally combined with an oil (e.g., fish oil). The resulting combination can be further cured, thereby further cross-linking the fatty acids and glycerides of the oil, to provide a fatty-acid based, pre-cure derived biomaterial that contains an antimicrobial agent. Thus, in this instance, a portion of the fatty acid-based biomaterial was pre-cured before formulation, and then exposed to further curing in the presence of an antimicrobial compound.

The process of creating a pre-cure (e.g., of a fish oil) has the advantage of creating an initial platform of oxidized fatty acid cross-links that will be hydrolyzed by human tissue. This process results in a partially cross-linked composition, with reduced oxidizable reactive sites (e.g., C=C bonds), that contains no antimicrobial compound. After the pre-cure is formed, the antimicrobial compound is then added.

Several methods are available to cure the oil starting material containing one or more therapeutic agents to produce a fatty acid-derived biomaterial for a drug release and delivery coating or stand-alone film in accordance with the present invention (for example, as described in US Patent Application Publications 2008/0118550, 2007/0202149, 2007/0071798, 2006/0110457, 2006/0078586, 2006/0067983, 2006/0067976, 2006/0067975, all of which are incorporated herein by reference). Preferred methods for curing the starting material to produce an antimicrobial agent-containing, fatty acid-derived biomaterial of the present invention include, but are not limited to, heating (e.g., employing an oven, a broadband infrared (IR) light source, a coherent IR light source (e.g., laser), and combinations thereof) and ultraviolet (UV) irradiation. The starting material may be cross-linked through auto-oxidation (i.e., oxidative cross-linking).

In accordance with various embodiments described herein, the drug release coatings and stand alone films of the present invention are formed of a fatty acid-derived biomaterial, which can be derived from saturated and unsaturated fatty acid compounds (e.g., free fatty acids, fatty acid ester, monoglycerides, diglycerides, triglycerides, metal salts, etc.). Preferably, the source of fatty acids described herein is saturated and unsaturated fatty acids such as those readily available in triglyceride form in various oils (e.g., fish oils). One method of the formation of a fatty acid-derived biomaterial is accomplished through autoxidation of the oil. As a liquid oil containing unsaturated fatty acid is heated, autoxidation occurs with the absorption of oxygen into the oil to create hydroperoxides in an amount dependent upon the amount of unsaturated (C=C) sites in the oil. However, the (C=C) bonds are not consumed in this initial reaction. Concurrent with the formation of hydroperoxides is the isomerization of (C=C) double bonds from cis to trans in addition to double bond conjugation. Continued heating of the oil results in the solidifying of the coating through the formation of cross-linking and by the further reaction of the hydroperoxides and the cleavage of C=C double bonds, which convert them into secondary oxidation byproducts including aldehydes, ketones, alcohols, fatty acids, esters, lactones, ethers, and hydrocarbons which can either remain within the coating and/or are volatilized during the process.

The type and amount of cross-links formed during oil oxidation can be tailored depending on the conditions selected (e.g., coating thickness, temperature, metal composition, etc.). For instance, heating of the oil allows for cross-linking between the fish oil unsaturated chains using a combination of peroxide (C—O—O—C), ether (C—O—C), and hydrocarbon (C—C) bridges (see, e.g., F. D. Gunstone, "Fatty Acid and Lipid Chemistry." 1999.). Heating at lower temperatures (below 150° C.) results in the formation of predominantly peroxide cross-links, where heating at higher temperatures (i.e. above 150° C.) results in the thermal degradation of peroxides and C=C and ether cross-links dominate (F. D. Gunstone, 1999).

In addition to thermal curing processes, oxidation of oils can also be induced by light (e.g., photo-oxygenation). Photo-oxygenation is limited to C=C carbon atoms and results in a conversion from cis to trans C=C isomers during curing (as occurs with heat initiated curing). However, photo-oxygenation using UV is a relatively quicker reaction than autoxidation from heat curing, in the realm of about 1000-1500 times faster. The quicker reaction especially holds true for methylene interrupted polyunsaturated fatty acids, such as EPA and DHA, which are found in the fish oil based embodiments of the present invention.

An important aspect of UV curing when compared to heat curing is that although the byproducts obtained by both curing methods are similar, they are not necessarily identical in amount or chemical structure. One reason for this is due to the ability of photo-oxygenation to create hydroperoxides at more possible C=C sites.

Photo-oxygenation, such as that which results from UV curing, due to its enhanced ability to create inner hydroperoxides, also results in the ability to form relatively greater amounts of cyclic byproducts, which also relates to peroxide cross-linking between fish oil hydrocarbon chains. For example, photo-oxygenation of linolenate results in 6 different types of hydroperoxides to be formed, whereas autoxidation results in only 4. The greater amount of hydroperoxides created using photo-oxygenation results in a similar, but slightly different, structure and amount of secondary byproducts to be formed relative to autoxidation from heat curing. Specifically, these byproducts are aldehydes, ketones, alcohols, fatty acids, esters, lactones, ethers, and hydrocarbons.

Depending on the oil curing conditions and the fatty acid composition of the starting oil, a fatty acid-derived biomaterial can be produced by curing the oil so as to oxidize the double bonds of the unsaturated fatty acid chains while predominantly preserving triglyceride ester functional groups. The oxidation of the unsaturated fatty acid chains results in the formation of hydroperoxides, which, with continued curing, are converted into and aldehydes, ketones, alcohols, fatty acids, esters, lactones, ethers, and hydrocarbons. With continued heating of the oxidized oil, the byproducts are volatilized, resulting in an increase in the coating viscosity in addition to the formation of ester cross-links. The formation of ester and lactone cross-links can occur via different types of mechanisms (i.e., esterification, alcoholysis, acidolysis, interesterification as described in F. D. Gunstone, 1999, Chapter 8, incorporated herein by reference)

between the hydroxyl and carboxyl functional components in the coating formed from the oxidation process (i.e., glyceride and fatty acid). The cross-linking reaction can form different types of ester linkages such as ester, anhydride, aliphatic peroxide, and lactones. One possible mechanism for the formation of the fish-oil derived biomaterial used herein can be provided as follows: fish oil (triglycerides) absorbs oxygen; oxidation of the C=C bonds in the oil occurs; fatty acid and glycerides (a mixture of mono, di- and tri) are formed; continued curing results in dehydration of neighboring carboxyl and hydroxyl functional groups; lactone/ester cross-links are formed between fatty acids and glycerides; and the oil solidifies into a bioabsorbable gel containing cross-linked fatty acids and glycerides. The reaction chemistry of this formation is as follows: isomerization and oxidation of C=C bonds; volatilization of water, hydrocarbons and aldehydes, resulting in an increase in coating viscosity; and ester and lactone cross-links formed results in solidifying the coating into a gel.

FIG. 1 provides a schematic of different methods to form esters from oils for illustrative purposes, but is not meant to be limiting in its scope to the invention.

In various aspects, provided herein is a means to load different antimicrobial compounds (e.g., silver compounds) into fatty acid-derived biomaterials. In one embodiment, these antimicrobial-containing biomaterials can be combined with a medical device in order to enhance the device's short term antimicrobial activity. For example, the release of silver ions from the oil silver-containing biomaterials (e.g., coating or stand-alone film) can be altered depending on the silver compound selected (e.g., whether it is an insoluble or soluble form of silver) in addition to the method of loading silver into the coating and/or formulation (e.g., silver compound encapsulated and cured into coating, sprayed onto cured coating, or soaked into cured coating). Depending on the method of incorporation of the antimicrobial compounds into the biomaterial, the antimicrobial release in water and chemical form of the antimicrobial can be altered, which can alter the efficacy of the antimicrobial-containing biomaterial.

In one embodiment, the antimicrobial behavior of the compounds incorporated into the antimicrobial-containing biomaterials (e.g., coatings or stand-alone films) can be altered by not only the form of antimicrobial agent, but also by the interaction between the antimicrobial compound and the biomaterial itself. The antimicrobial-containing biomaterials described herein are created by thermal oxidation of the unsaturated double bonds in an oil, initially resulting in the formation of hydroperoxides, which are then subsequently further oxidized into other byproducts including fatty acids. Carboxyl and hydroxyl groups formed during the oxidation of the oil (i.e., fatty acids and glycerides) can react together upon further heating by esterification, which results in the formation of lactone and ester cross-links to gel the coating. Thus, depending on the type of antimicrobial compound and the stage of incorporation of the compound into the coating, different antimicrobial coatings (e.g., silver-containing coatings) can be produced by not only the type of antimicrobial compound selected, but also due to the final resultant chemistry produced by the interaction of the antimicrobial compound with the different molecular species present in the oil-derived coating. Additionally, unlike traditional hydrophobic medical device materials such as PTFE, the antimicrobial-containing biomaterial becomes readily hydrated in an aqueous environment, which results in the release of antimicrobial compounds (e.g., silver compounds) to be observed.

In another embodiment, the method of incorporating an antimicrobial compound into the biomaterial is to utilize an antimicrobial compound (e.g., a silver compound) to create a suspension into the oil starting material by either cryo-grinding and/or sonication with vortexing. In one embodiment, of this method, the antimicrobial compound is a silver compound, and in another embodiment, the silver compound is in a nanoparticle size. Thus, a silver-containing biomaterial (e.g., coating or stand-alone film) can be produced by the incorporation of silver nanoparticles into the oil starting material (e.g., fish oil) after sonicating and vortexing to uniformly suspend the nanoparticles into the oil. The oil-nanoparticle suspension is then thermally cured either as a stand-alone product or as a coating onto a medical device. This process results in encapsulating the silver nanoparticles in the coating existing predominantly in their native silver metal form or as silver oxide. The silver nanoparticles used in this invention can be of different sizes and either be pure silver metal nanoparticles or nanoparticles coated with a surface coating to prevent agglomeration. This process can also be applied to other antimicrobial agents (e.g., triclosan, chlorhexidine, gentamicin, gentamicin sulfate).

As discussed above, the fatty-acid and glyceride (e.g., oil, e.g., fish oil) can be cured to induce fatty-acid oxidation and crosslinking of a portion, majority, or all of the fatty acids and glycerides to form a gel. The antimicrobial agent can be added to the fatty acid before, during, or after the curing process. In one embodiment, the method to incorporate a silver antimicrobial compound into a fatty-acid derived biomaterial is to combine a water soluble form of silver with a formulation containing a mixture of native oil with partially oxidized oil (i.e., a pre-cured oil). This method for incorporating a silver compound involves combining a formulation of an aqueous form of silver ($Ag^+$) in a formulation of fish oil and pre-cured fish oil. In one embodiment, the formulation of fish oil and pre-cured fish oil is approximately a 50:50 ratio of fish oil:pre-cured fish oil. The silver ions in the silver nitrate solution then react with the lipid hydroperoxides formed during the oxidation of the oil-derived cross-linked gel and are reduced to silver metal.

In another embodiment, a method to load antimicrobial compounds into a silver-containing biomaterial is to first create the coating using a thermal cure process and then soaking the coating in a water soluble form of silver (e.g., silver nitrate or silver acetate). This process creates silver fatty acid salts within the silver-containing biomaterial. Additionally, the amount of silver fatty acid salts formed within the biomaterial can be altered as a function of pH, silver compound selected and soak time. Using this process, the amount of silver ions produced within the biomaterial are released more rapidly, typically in less than a week as measured using in-vitro dissolution testing methodology. Accordingly, this process can be used with any other water soluble antimicrobial agent.

It will be appreciated that the present invention can be implemented as a coating, as well as a stand-alone material, or other forms as described herein (e.g., a gel, a particle, or an emulsion). As would be understood by those of ordinary skill in the art these biomaterials will have an outer surface that interacts with its environment upon implantation or application.

Antimicrobial-containing biomaterial coatings and stand-alone films of the present invention are formed from an oil component. The term "oil component" is also referred to herein as the "oil acid-containing starting material" or "fatty acid-containing starting material." The "fatty acid-containing starting material" can be natural or derived from synthetic sources. Preferably, the "oil containing starting material" comprises unsaturated fatty acids. The oil component can be either an oil, or an oil composition. The oil component can be a naturally occurring oil, such as fish oil, flax seed oil, grape seed oil, or palm oil, or other oils having desired characteristics. The oil can also be a synthetic oil. One embodiment of the present invention makes use of a fish oil in part because of the high content of omega-3 fatty acids, which can provide healing support for damaged tissue, as discussed herein. The fish oil can also serve as an anti-adhesion agent. In addition, the fish oil maintains anti-inflammatory or non-inflammatory properties as well. The present invention is not limited to formation of the fatty acid-derived biomaterial with fish oil as the oil. However, the present application makes reference to the use of fish oil as one example embodiment. Other naturally occurring oils or synthetic oils can be utilized in accordance with the present invention as described herein.

It should be noted that as utilized herein, the term "fish oil" includes but is not limited to omega-3 fatty acid, unsaturated fatty acid, polyunsaturated fatty acid, fish oil fatty acid, free fatty acid, monoglycerides, di-glycerides, or triglycerides, esters of fatty acids, or a combination thereof. The fish oil may include one or more of arachidic acid, gadoleic acid, arachidonic acid, eicosapentaenoic acid, docosahexaenoic acid or derivatives, analogs and pharmaceutically acceptable salts thereof.

Furthermore, as utilized herein, the term free fatty acid includes, but is not limited to, one or more of butyric acid, caproic acid, caprylic acid, capric acid, lauric acid, myristic acid, palmitic acid, palmitoleic acid, stearic acid, oleic acid, vaccenic acid, linoleic acid, alpha-linolenic acid, gamma-linolenic acid, behenic acid, erucic acid, lignoceric acid, analogs and pharmaceutically acceptable salts thereof. The naturally occurring oils, including fish oil, are cured as described herein to form a hydrophobic cross-linked fatty acid-derived biomaterial, creating the coating.

With regard to the aforementioned oils, it is generally known that the greater the degree of unsaturation in the fatty acids the lower the melting point of a fat, and the longer the hydrocarbon chain the higher the melting point of the fat. An unsaturated fat, thus, has a lower melting point, and a saturated fat has a higher melting point. Those fats having a lower melting point are more often oils at room temperature. Those fats having a higher melting point are more often waxes or solids at room temperature. Therefore, a fat having the physical state of a liquid at room temperature is an oil. In general, unsaturated fats are liquid oils at room temperature, and saturated fats are waxes or solids at room temperature.

Polyunsaturated fats are one of four basic types of fat derived by the body from food. The other fats include saturated fat, as well as monounsaturated fat and cholesterol. Polyunsaturated fats can be further composed of omega-3 fatty acids and omega-6 fatty acids. Under the convention of naming, the unsaturated fatty acid according to the position of its first double bond of carbons, those fatty acids having their first double bond at the third carbon atom from the methyl end of the molecule are referred to as omega-3 fatty acids. Likewise, a first double bond at the sixth carbon atom is called an omega-6 fatty acid. There can be both mono-unsaturated and polyunsaturated omega fatty acids.

Omega-3 and omega-6 fatty acids are also known as essential fatty acids because they are important for maintaining good health, despite the fact that the human body cannot make them on its own. As such, omega-3 and omega-6 fatty acids must be obtained from external sources, such as food. Omega-3 fatty acids can be further characterized as containing eicosapentaenoic acid (EPA), docosahexanoic acid (DHA), and alpha-linolenic acid (ALA). Both EPA and DHA are known to have anti-inflammatory effects and wound healing effects within the human body.

The antimicrobial-containing biomaterial described herein may also be in the form of an emulsion. The term "emulsion," as used herein, includes classic oil-in-water or water in oil dispersions or droplets, as well as other lipid structures that can form as a result of hydrophobic forces that drive polar residues (i.e., long hydrocarbon chains, such as those found in fatty acids) away from water and drive polar head groups toward water, when a water immiscible oily phase is mixed with an aqueous phase. These other lipid structures include, but are not limited to, unilamellar, paucilamellar, and multilamellar lipid vesicles, micelles, and lamellar phases. Such systems possess a finite stability, generally defined by the application or relevant reference system, which may be enhanced by the addition of amphiphilic molecules or viscosity enhancers. Accordingly, the fatty acid-based particles provided herein (with or without a therapeutic agent) also can be loaded into fatty acid based liquids (e.g., fish oil) or gels (e.g., partially cured fish oil) to create an emulsion.

Antimcrobial Agents

As discussed above, provided herein are compositions comprising an antimicrobial agent, a fatty acid, and a glyceride, wherein the fatty acid and glyceride components are cross-linked. As used herein the term "antimicrobial," "antimicrobial agent" or "antimicrobial composition" refers to a composition that has the effect of inhibiting the growth of bacteria, fungi, yeast, algae, etc., or killing these microorganisms. Specific non-limiting examples of antimicrobials include elemental silver, silver nanoparticle, silver nitrate, silver chloride, silver fluoride, silver bromide, silver oxide, silver sulfate, silver carbonate, silver cyanide, silver tetrafluoroborate, silver sulfide, silver acetate, silver lactate, silver benzoate, silver cyclohexanebutyrate, silver diethyldithiocarbamate, silver trifluoromethanesulfonate, triclosan, chlorhexidine, triclocarban, hexachlorophene, dibromopropamidine, chloroxylenol, phenol and cresol. Examples of antimicrobial compounds include, but are not limited to, diamidines, iodine and iodophors, peroxygens, phenols, bisphenols, halophenols, biguanides and silver compounds.

An antibiotic is another example of an antimicrobial agent. The term "antibiotic" as used herein refers to any compound known to one of ordinary skill in the art that will inhibit the growth of, or kill, bacteria. Non-limiting examples of antimicrobial agents that can be used with the biomaterials provided herein include gentamicin sulfate, penicillin g, ephalothin, ampicillin, amoxicillin, augmentin, aztreonam, imipenem, streptomycin, gentamicin, vancomycin, clindamycin, erythromycin, azithromycin, polymyxin, bacitracin, amphotericin, nystatin, rifampicin, tetracycline, doxycycline, chloramphenicol, nalidixic acid, ciprofloxacin, sulfanilamide, gantrisin, trimethoprim, isoniazid, para-aminosalicylic acid, and minocycline.

These anti-infective agents can be used either alone or in combination with one another to create an infection-resistant fatty acid based biomaterial.

When the antimicrobial agent is a silver compound, the composition can be referred to as a "silver-containing biomaterial." Silver exists in two forms, ionic ($Ag^+$) and elemental ($Ag^0$), but only the ionic form of silver has antimicrobial properties (S. Pal et al. 2007, "Applied and Environmental Microbiology" Vol. 73 (6), 1712-1720; A. B.

G. Lansdown. 2006, "Curr. Probl. Dermatol." Vol 33, 17-34; R. O. Darouiche, 1999, "Clinical Infectious Diseases" Vol. 29, 1371-1377; V. Sambhy et al., 2006, "J. American Chem. Society. Vol. 128, 9798-9808; Matsumura, K et al., 2003, "Applied & Environmental Microbiology" Vol. 69, No. 7, 4278-4281). The antimicrobial activity of silver depends on the interaction of silver ions ($Ag^+$) with the bacteria's cellular membrane, which results in preventing DNA replication and subsequent proliferation of bacteria. All forms of silver produce silver ions, but the rate of silver ionization and/or release in a hydrated environment is dependent on the silver compound selected (A. B. G. Lansdown. 2006, "Curr. Probl. Dermatol." Vol 33, 17-34; R. O. Darouiche, 1999, "Clinical Infectious Diseases" Vol. 29, 1371-1377; V. Sambhy et al., 2006, "J. American Chem. Society. Vol. 128, 9798-9808; Matsumura, K et al., 2003, "Applied & Environmental Microbiology" Vol. 69, No. 7, 4278-4281). For instance, silver nitrate rapidly forms silver ions in an aqueous environment whereas silver metal slowly forms silver ions. The amount of silver needed to produce an antimicrobial effect has been previously reported to be in the range of only 50 ppb (K. C. Chaw et al. 2005). Thus, only small amounts of silver need to be loaded on the device to be effective. The incorporation of the silver antimicrobial into the coating is designed to protect the device from bacterial colonization.

Antimicrobial silver compounds that can be used with the biomaterials of the invention include, but are not limited to, silver nitrate, silver chloride, silver fluoride, silver bromide, silver oxide, silver sulfate, silver carbonate, silver cyanide, silver tetrafluoroborate, silver sulfide, silver acetate, silver lactate, silver benzoate, silver cyclohexanebutyrate, silver diethyldithiocarbamate, silver trifluoromethanesulfonate and mixtures thereof. In a particular embodiment, the silver is ionic silver and is selected from the group consisting of silver nitrate, silver acetate, silver oxide, and mixtures thereof.

The release of silver ions from the silver-containing biomaterial can be altered depending on the silver compound selected (e.g., whether it is an insoluble or soluble form of silver) in addition to the method of loading silver into the coating and/or formulation (e.g., silver compound encapsulated and cured into coating, sprayed onto cured coating, or soaked into cured coating). Depending on the chemical form of the silver compound and the method of incorporation of the silver compounds into the biomaterial, the silver ion's release in water and can be altered, which can alter the biomaterial's efficacy.

As discussed above, the antimicrobial behavior of the silver compounds incorporated into the silver-containing biomaterials can be altered by not only the form of silver compounds that are incorporated into a biomaterial, but also by the chemical interaction between the silver compound and the biomaterial itself. Depending on the type of silver compound and the stage of incorporation of the silver compound into the coating, different silver-containing biomaterials can be produced by not only the type of silver compound selected, but also due to the final resultant chemistry produced by the interaction of the silver compound with the different molecular species present in the oil-derived coating.

In another embodiment, the method of incorporating a silver antimicrobial compound into the biomaterial is to create a suspension of a silver compound in the oil starting material (e.g., fish oil). In one embodiment, the suspension is created by either cryo-grinding and/or sonication with vortexing. The silver compound utilized in this invention may or may not be in a nanoparticle size. Specifically, an antimicrobial silver enhanced oil-derived gel coating can be produced by the incorporation of commercially available silver nanoparticles into the oil starting material after sonicating and vortexing to uniformly suspend the nanoparticles into the oil. The oil-nanoparticle suspension is then thermally cured either as a stand-alone product or as a coating onto a medical device. This process results in encapsulating the silver nanoparticles in the coating existing predominantly in their native silver metal form or as silver oxide. The silver nanoparticles used in this invention can be of different sizes and either be pure silver metal nanoparticles or nanoparticles coated with a surface coating to prevent agglomeration. A coating containing silver metal nanoparticles <150 nm was shown to release silver ions from the coating out to a minimum of 65 days in a water dissolution testing using an ICP silver assay and was effective at preventing biofilm formation by a clinical isolate of MRSA in in-vitro studies for a minimum of 3 days using this technique.

In various aspects, another method to incorporate a silver antimicrobial compound into an oil-derived cross-linked gel is to use a water soluble form of silver and combine that with a formulation containing a mixture of native oil with partially oxidized oil (a pre-cured oil). In one embodiment, the method for incorporating a silver compound can involve combining a formulation of aqueous silver nitrate (or silver acetate) in a mixture of fish oil and pre-cured oil (e.g., a formulation of approximately 50:50 fish oil:pre-cured fish oil). The pre-cured fish oil can be prepared by bubbling oxygen through fish oil while heating, e.g., approximately 18 hrs at 93° C. The silver ions in the silver nitrate solution then react with the lipid hydroperoxides formed during the oxidation of the oil-derived cross-linked gel and are reduced to silver metal (A. Kumar et al., "Nature Materials". 2008 Vol 7, pgs 236-241). Depending on the conditions employed, the size of the reduced silver metal may or may not be in a nanoparticle size. In addition to reducing the silver into metal form, the presence of the silver nitrate solution with fatty acids in the coating can also result in producing silver fatty acid salts, which are antimicrobial (C. L. Fox et al., 1991; F. M. Mattei, 1980; M. Roby, 2004). Oil-derived materials (e.g., coating or stand-alone film) formed by this process were shown to release silver ions from the coating out to a minimum of 60 days in water dissolution testing using an ICP silver assay and were effective at preventing biofilm formation by clinical isolates of MRSA and *Staphylococcus aureus* in in-vitro studies for a minimum of 3 days using this technique.

Another method to load silver antimicrobial compounds into silver-containing biomaterial is to first create a coating or stand alone film using a thermal cure process and then soak or spray a water soluble form of silver (e.g., silver nitrate or silver acetate) onto the coating. This is performed by soaking the oil-derived gel into a solution of either silver nitrate or silver acetate for a fixed period of time to load silver into the coating. This process predominantly creates silver fatty acid salts within the coating, which was confirmed using FTIR spectroscopy. Additionally, the amount of silver fatty acid salts formed within the coating or stand alone film can be altered as a function of pH, silver compound selected (silver acetate or silver nitrate) and soak time. Using this process, silver ions are released from the coating more rapidly, typically in less than a week in a water dissolution test using an ICP silver assay.

Another antimicrobial used with the biomaterials provided herein can be triclosan. Triclosan (2,4,4'-trichloro-2'- hydroxydiphenyl ether) is a broad spectrum antimicrobial agent that is classified as a chlorinated bisphenol that has long been used as a biocide in various products including soap products, oral care products and cosmetics. Triclosan activity covers a broad range of gram positive bacteria such as *Bacillus subtilis, Mycobacterium smegmatis, Staphylococcal aureus*, gram negative bacteria including *E. coli, Salmonella typhimurium, Shigella flexneri*, yeasts and some fungi (M. J. Stewart et. al, "J. Mol. Biol., 1999, Vol 290, pgs 859-865). At low concentrations, triclosan is bacteriostatic and bactericidal at higher concentrations and has been found to have a low toxicity profile making it ideal for use in personal hygiene products and various medical devices (A. D. Russell, Journal of Antimicrobial Chemotherapy, 2004 Vol 53, pgs 693-695). Triclosan's mechanism of action targets a specific enzyme, enoyl-acyl carrier protein reductase (ENR), involved in the lipid biosynthesis pathway by acting as competitive inhibitor. ENR catalyzes the terminal reaction in the fatty acid elongation cycle during fatty acid biosynthesis. Enzyme inhibition studies using *E. coli* have demonstrated that the enzyme-inhibitor complex formed between triclosan and ENR are strong, slow to dissociate and relatively irreversible (M. Kapoor, "Biochem. J." 2004, Vol 381, 719-724; J. Stewart et. al, "J. Mol. Biol., 1999, Vol 290, 859-865). The lipophilic nature of triclosan makes it an ideal antimicrobial agent to incorporate into the fatty acid biomaterial coating as described in the present invention.

The antimicrobial used with the biomaterials provided herein can be chlorhexidine. Chlorhexidine is a biocide belonging to the biguanides group. It is widely used as a preservative and as an antiseptic agent in hand washing products, oral products and coated in combination with silver-sulfadiazine on some medical devices such as urinary catheters to prevent biofilm formation. Uptake of chlorhexidine is pH dependent and its antibacterial action occurs by diffusing into and attacking the bacterial cytoplasm after damaging bacterial outer cell membranes (G. McDonnell et. al., "Clinical Biological Reviews." 1997, Vol 12(1), 147-179; S. Bassetti, 2001, Vol 45(4), 1535-1538).

The antimicrobial used with the biomaterials provided herein can be gentamicin. Gentamicin is a water soluble aminoglycoside antibiotic that is active against a range of gram positive and gram negative bacteria. The mechanism of transport of gentamicin across cell membranes is not well known but it is hypothesized that gentamicin interacts with some components of the cell membrane by the interaction of gentamicin amino groups and free fatty aldehydes via a Schiff-base reaction (D. E. Auslander et. al., "J Pharm Sci." 1975, 64(3), 516-519).

In one embodiment, the antimicrobial-containing biomaterial contains more than one antimicrobial compound. For example, the antimicrobial agent can be combined with the fatty acid/glyceride starting material to form a composition, such that the composition is cross-linked so the antimicrobial-containing biomaterial is formed, and then an additional antimicrobial agent is added to the surface of the biomaterial (by spraying, submersing, etc.). The additional agent can be the same as the antimicrobial agent incorporated in the cross-linked matrix, or different. In another embodiment, two or more different antimicrobial agents are combined with the fatty acid/glyceride starting material to form a composition, such that the composition is cross-linked so an antimicrobial-containing biomaterial is formed that that contains two or more antimicrobial agents.

In another embodiment, provided herein is a silver-containing biomaterial comprising fish oil, wherein the fatty acids and glycerides of the fish oil are cross-linked, and wherein the silver-containing biomaterial further comprises an additional therapeutic agent, such as an antimicrobial agent. In a particular embodiment, the silver-containing biomaterial further comprises triclosan, chlorhexidine or gentamicin.

In another embodiment, the additional therapeutic agent that is loaded into the antimicrobial-containing biomaterial (e.g., silver-containing biomaterial) is an anti-adhesive agent. As used herein, the term "anti-adhesion agent" refers to any compound that prevents adhesions or accretions of body tissues formed in response to injury of various kinds, e.g., surgery, infection, chemotherapy, radiation. Anti-adhesion agents include, but are not limited to, hyaluronic acid, human plasma derived surgical sealants, and agents comprised of hyaluronate and carboxymethylcellulose that are combined with dimethylaminopropyl, ethylcarbodimide, hydrochloride, PLA, and/or PLGA.

In various aspects, the additional antimicrobial agent is sprayed onto the outside surface of the antimicrobial-containing biomaterial (e.g., coating or stand-alone film). In one embodiment, the antimicrobial agent is triclosan. Alternatively, the triclosan can be sprayed in combination with a soluble silver compound onto the outside surface of the silver-containing biomaterial (e.g., coating or stand-alone film).

In another embodiment, the fatty acid-derived biomaterial can be cured with a silver nanoparticle or silver compound in the base coating, and then an antimicrobial and/or antibiotic agent can be sprayed onto the outer surface of the cured coating. In one embodiment, the antimicrobial/antibiotic agent selected is triclosan.

In another embodiment, the antimicrobial agent can be loaded by incorporating the agent into the biomaterial during the thermal cure process onto a finished device. The fatty acid-derived biomaterial can contain either triclosan by itself and/or in combination with a silver nanoparticle and/or silver compound.

Coating Hydrolysis and Bioabsorption Chemistry of Fatty Acid-Derived Biomaterials Biodegradable and bioabsorbable implantable materials with ester, lactone, and anhydride functional groups are typically broken down by either chemical and/or enzymatic hydrolysis mechanisms (K. Park et al., "Biodegradable Hydrogels for Drug Delivery." 1993; J. M. Andersen, "Perspectives on the In-Vivo Responses of Biodegradable Polymers." in *Biomedical Applications of Synthetic Biodegradable Polymers*, edited by Jeffrey O. Hollinger. 1995, pgs 223-233). Chemical hydrolysis of an antimicrobial-containing biomaterial occurs when the functional group present in the material is cleaved by water. Enzymatic hydrolysis is the cleavage of functional groups in an antimicrobial-containing biomaterial caused by the reaction with a specific enzyme (e.g., triglycerides are broken down by lipases (enzymes) that result in free fatty acids that can then be transported across cell membranes). The length of time a biodegradable antimicrobial-containing biomaterial takes to be hydrolyzed is dependent on several factors such as the cross-linking density of the material, the thickness, the hydration ability of the coating, the crystallinity of the fatty acid-derived biomaterial, and the ability for the hydrolysis products to be metabolized by the body (K. Park et al., 1993 and J. M. Andersen, 1995).

It should be noted that a bioabsorbable substance is different from a biodegradable substance. Biodegradable is generally defined as capable of being decomposed by biological agents, or capable of being broken down by microorganisms or biological processes. Biodegradable substances can cause an inflammatory response due to either the parent substance or those formed during hydrolysis, and they may or may not be absorbed by tissues. Some biodegradable substances are limited to a bulk erosion mechanism for hydrolysis. For example, a commonly used biodegradable polymer, PLGA (poly(lactic-co-glycolic acid)) undergoes chemical hydrolysis in-vivo to form two alpha-hydroxy acids, specifically glycolic and lactic acids. Thus, in one embodiment, the antimicrobial-containing biomaterial provided herein is non-polymeric. Although glycolic and lactic acids are byproducts of various metabolic pathways in the body, it has been demonstrated in previous medical implant and local drug delivery applications that a local concentration of these products results in an acidic environment to be produced, which can lead to inflammation and damage to local tissue (S. Dumitriu, "Polymeric Biomaterials." 2002). Clinically, this can lead to impaired clinical outcomes such as restenosis (D. E. Drachman and D. I. Simon. *Current Atherosclerosis Reports.* 2005, Vol 7, pgs 44-49; S. E. Goldblum et al. *Infection and Immunity.* 1989, Vol. 57, No. 4, pgs 1218-1226) and impaired healing in a coronary stent application which can lead to late-stent thrombosis or adhesion formation in an abdominal hernia repair (Y. C. Cheong et al. *Human Reproduction Update.* 2001; Vol. 7, No. 6: pgs 556-566). Thus, an ideal antimicrobial-containing biomaterial should not only demonstrate excellent biocompatibility upon implantation, but should also maintain that biocompatibility during the life of its implantation with its hydrolysis byproducts being absorbable by local tissue.

The bio-absorbable nature of the antimicrobial-containing biomaterial (derived, e.g., from fish oil containing triglycerides and fatty acids) used as a stand-alone film, a coating for a medical device, or in drug delivery applications results in the biomaterial being absorbed over time by the cells of the body tissue. In various embodiments, there are substantially no substances in the biomaterial, or in vivo conversion by-products of the biomaterial, which induce an inflammatory response, e.g., the antimicrobial-containing biomaterial converts in vivo into non-inflammatory components. For example, in various embodiments, the antimicrobial-containing biomaterial of the present invention upon absorption and hydrolysis do not produce lactic acid and glycolic acid break-down products in measurable amounts. The chemistry of the antimicrobial-containing biomaterial described herein consists of predominantly fatty acid and glyceride components that can either be hydrolyzed in-vivo by chemical and/or enzymatic means which results in the release of fatty acid and glyceride components that can be transported across cell membranes. Subsequently, the fatty acid and glyceride components eluted from the antimicrobial-containing biomaterials are directly metabolized by cells (i.e., they are bio-absorbable). The bio-absorbable nature of the coating and stand-alone film of the present invention results in the biomaterial being absorbed over time, leaving only an underlying delivery or other medical device structure that is biocompatible. There is substantially no foreign body inflammatory response to the biomaterial or its hydrolysis products in the preferred embodiments of the present invention.

Because the materials of the invention (derived, e.g., from fish oil containing triglycerides and fatty acids) are biocompatible, and they hydrolyze into non-inflammatory components, and are subsequently bio-absorbed by surrounding tissue, they are referred to as "biomaterials."

Fatty Acid-Derived Biomaterial Biocompatibility and In-Vivo Performance

The process of making the antimicrobial-containing biomaterials (e.g., coating or stand-alone film) as described herein led to some unexpected chemical processes and characteristics in view of traditional scientific reports in the literature about the oxidation of oils. Oil oxidation has traditionally been of concern for oil curing procedures due to the formation of reactive byproducts such as hydroperoxides and alpha-beta unsaturated aldehydes that are not considered to be biocompatible (H. C. Yeo et al. *Methods in Enzymology.* 1999, Vol. 300, pgs 70-78; S—S. Kim et al. *Lipids.* 1999, Vol. 34, No. 5, pgs 489-496.). However, the oxidation of fatty acids from oils and fats are normal and important in the control of biochemical processes in-vivo. For example, the regulation of certain biochemical pathways, such as to promote or reduce inflammation, is controlled by different lipid oxidation products (V. N. Bochkov and N. Leitinger. *J. Mol. Med.* 2003; Vol. 81, pgs 613-626). Additionally, omega-3 fatty acids are known to be important for human health and specifically EPA and DHA are known to have anti-inflammatory properties in-vivo. However, EPA and DHA are not anti-inflammatory themselves, but it is the oxidative byproducts they are biochemically converted into that produce anti-inflammatory effects in-vivo (V. N. Bochkov and N. Leitinger, 2003; L. J. Roberts II et al. *The Journal of Biological Chemistry.* 1998; Vol. 273, No. 22, pgs 13605-13612.). Therefore, by selecting the appropriate process conditions, an antimicrobial-containing biomaterial (derived from, e.g., fish oil) can be created and controlled using oil oxidation chemistry with a final chemical profile that will have a favorable biological performance in-vivo.

The process of making an antimicrobial-containing biomaterial as described herein leads to a final chemical profile that is biocompatible, minimizes adhesion formation, acts as a tissue separating barrier, and is non-inflammatory with respect to the material chemistry and the products produced upon hydrolysis and absorption by the body in-vivo. The reason for these properties is due to several unique characteristics of the antimicrobial-containing biomaterials (e.g., coatings or stand-alone films).

In some embodiments, no toxic, short-chained cross-linking agents (such as glutaraldehyde) are used to form the antimicrobial-containing biomaterials (e.g., coatings or stand-alone films) of the invention. Short chain cross-linking agents can elute during hydrolysis of biodegradable polymers and cause local tissue inflammation. The process of creating antimicrobial-containing biomaterials does not involve adding external cross-linking agents because the oil is solely cured into a coating using oil autoxidation or photo-oxidation chemistry. The oxidation process results in the formation of carboxyl and hydroxyl functional groups that allow for the fatty acid-derived biomaterial to become hydrated and become slippery, which allows for frictional injury during and after implantation to be significantly reduced and/or eliminated. The methods of making the antimicrobial-containing biomaterials described herein allow the alkyl chains of the fatty acid, glyceride and other lipid byproducts present in the antimicrobial-containing biomaterial to be disordered, which creates a biomaterial that is flexible and aids in handling of the material while being implanted. Thus, in one embodiment, the antimicrobial-containing biomaterials (derived, e.g., from fish oil) do not contain any cross-linking agents.

There are several individual chemical components of the antimicrobial-containing biomaterial that aid in its biocompatibility and its low to non-inflammatory response observed in-vivo. The processes of creating a fatty acid-derived biomaterial described herein result in low to non-detectable amounts of oxidized lipid byproducts of biocompatibility concern, such as aldehydes. These products are either almost completely reacted or volatilized during the curing process as described in this invention. The process of creating an antimicrobial-containing biomaterial largely preserves the esters of the native oil triglycerides and forms ester and/or lactone cross-links, which are biocompatible.

Figure 2:
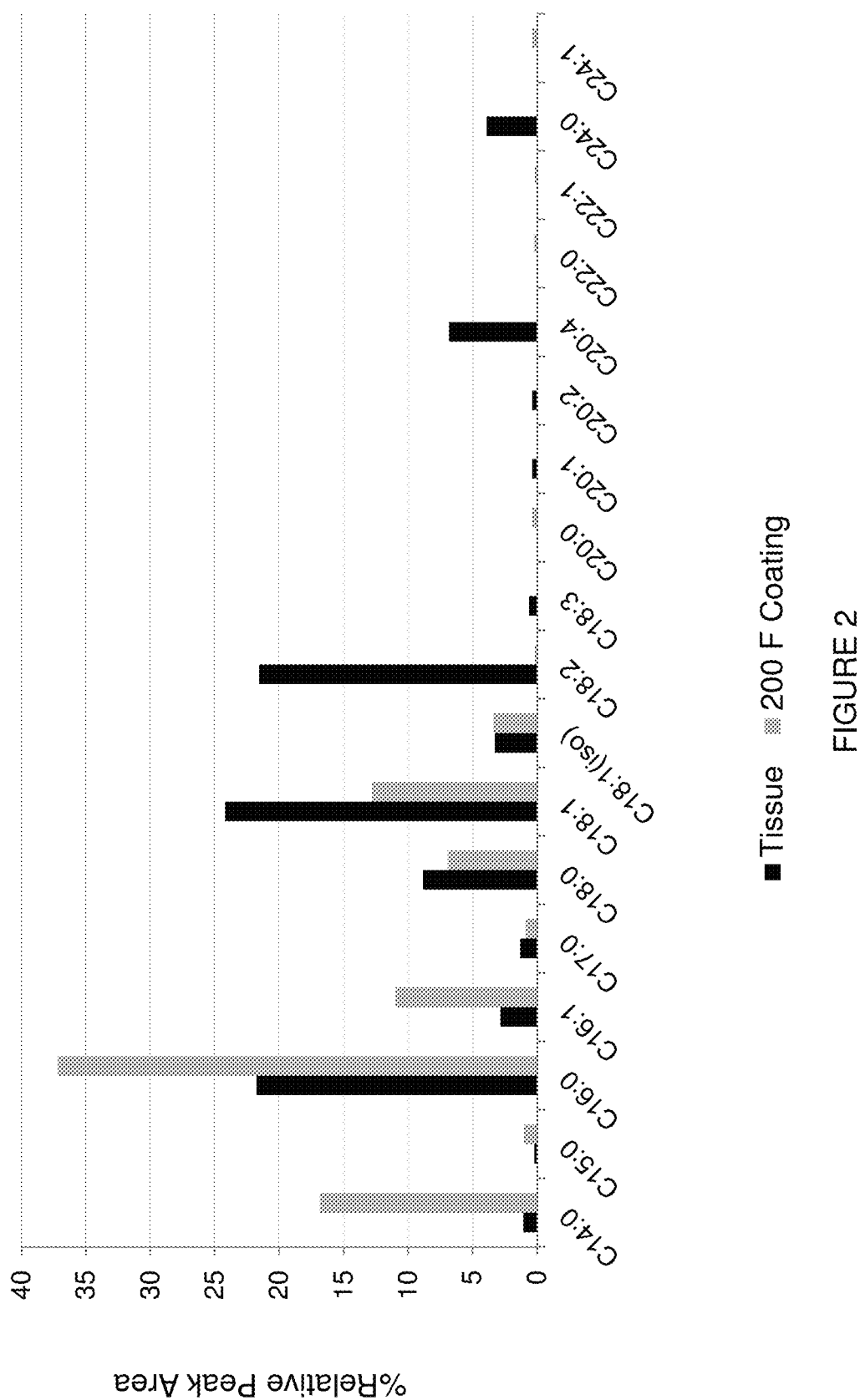
FIG. 2 shows bar graphs showing similarity of fatty acid composition between fatty acid-derived biomaterial coating and biological tissue.

In addition to general chemical properties of an antimicrobial-containing biomaterial that assists in its biocompatibility, there are also specific chemical components that have positive biological properties. Another aspect is that the fatty acid chemistry produced upon creation of a fatty acid-derived biomaterial is similar to the fatty acid chemistry of tissue, as presented in FIG. 2. Thus, as fatty acids are eluting from the biomaterial they are not viewed as being "foreign" by the body and cause an inflammatory response. In fact, C14 (myristic) and C16 (palmitic) fatty acids present in the coating have been shown in the literature to reduce production of α-TNF, an inflammatory cytokine. The expression of α-TNF has been identified as one of the key cytokines responsible for "turning on" inflammation in the peritoneal after hernia repair, which can then lead to abnormal healing and adhesion formation. α-TNF is also an important cytokine in vascular injury and inflammation, such as vascular injury caused during a stent deployment. In addition to the fatty acids just specified, there have also been additional oxidized fatty acids identified that have anti-inflammatory properties. Other components identified from the fatty acid-derived coatings as described in this invention are delta-lactones (i.e., 6-membered ring cyclic esters). Delta-lactones have been identified as having anti-tumor properties.

These components identified are not meant to be limiting in scope to this invention as changes in starting oil composition and/or process conditions can invariably alter the fatty acid and/or oxidative byproduct profiles and can be tailored as needed depending on the intended purpose and site of application of the fatty acid-derived biomaterial.

In summary, the biocompatibility and observed in in-vivo performance of antimicrobial-containing biomaterials described herein is not only beneficial as to prevent a foreign body response in-vivo due to the similarity of the fatty acid composition of the material to native tissue (i.e., a biological "stealth" coating), but the specific fatty acids and/or other lipid oxidation components eluting from the coating add in preventing foreign body reactions and reducing or eliminating inflammation, which leads to improved patient outcomes. Additionally, the fatty acid and glyceride components eluted from the antimicrobial-containing biomaterials are able to be absorbed by local tissue and metabolized by cells. Hence, the antimicrobial-containing biomaterial (e.g., coating or stand-alone film) described in this invention is also bioabsorbable.

Antimicrobial Properties of Antimicrobial-Containing Biomaterials

In the present invention, the antimicrobial-containing biomaterial is composed of various lipid components, free fatty acids and glycerides that are derived from, e.g., fish oil. The source of fatty acids in this invention may consist of but are not limited to other oils including flaxseed oil, grapeseed oil, olive oil, corn oil, peanut oil, safflower oil and soybean oil.

Generally, gram positive bacteria have been shown to be more sensitive to the bactericidal effects of fatty acids with gram negative bacteria being less sensitive. Longer chain unsaturated fatty acids have greater bactericidal activity than shorter chain saturated fatty acids, particularly against gram positive bacteria. This difference in bacterial sensitivity towards long chain unsaturated fatty acids and short chain saturated fatty acids are likely a result of the differences in bacterial surface structure and the mechanism of antimicrobial effects that occur between the fatty acid and bacteria. Longer chain fatty acids may be able to better insert the hydrocarbon chain into the bacterial phospholipid bilayer thereby conferring membrane destabilization and subsequent bactericidal effects. Monoglycerides have also been identified to act as nonionic surfactants that alter membrane permeability by penetrating the bacterial cell membrane causing plasma membrane disintegration. Likewise, short chain and medium chain fatty acids can enter bacterial cells by diffusion into bacterial cells in an undissociated form and cause intracellular acidification by dissociating within the bacterial protoplasm. The decreased intracellular pH can in turn result in enzymatic inactivation and interrupt amino acid transport which is important in protein synthesis. An advantage of the antibacterial properties exhibited by fatty acids and their respective monoglycerides is the decreased potential to develop bacterial resistance due to the mechanisms by which bacteria are killed.

Uses

The antimicrobial-containing biomaterials provided herein can be used, for example, for wound healing in a subject, e.g., a human or non-human animal. The process of wound healing involves tissue repair in response to injury and it encompasses many different biologic processes, including epithelial growth and differentiation, fibrous tissue production and function, angiogenesis, and inflammation. Accordingly, the antimicrobial-containing material provides an excellent material suitable for wound healing applications.

The antimicrobial-containing biomaterials provided herein can be used, for example, to prevent tissue adhesion. The tissue adhesion can be a result of blunt dissection. Blunt dissection can be generally described as dissection accomplished by separating tissues along natural cleavage lines without cutting. Blunt dissection is executed using a number of different blunt surgical tools, as is understood by those of ordinary skill in the art. Blunt dissection is often performed in cardiovascular, colorectal, urology, gynecology, upper GI, and plastic surgery applications, among others.

After the blunt dissection separates the desired tissues into separate areas, there is often a need to maintain the separation of those tissues. In fact, post surgical adhesions can occur following almost any type of surgery, resulting in serious postoperative complications. The formation of surgical adhesions involves complex inflammatory processes in which tissues that normally remain separated in the body come into physical contact with one another and attach to each other as a result of surgical trauma.

It is believed that abdominal adhesions are formed when bleeding and leakage of plasma proteins from damaged tissue deposit in the abdominal cavity and form what is called a fibrinous exudate. Fibrin, which restores injured tissues, is sticky, so the fibrinous exudate may attach to adjacent anatomical structures in the abdomen. Post-traumatic or continuous inflammation exaggerates this process, as fibrin deposition is a uniform host response to local inflammation. This attachment seems to be reversible during the first few days after injury because the fibrinous exudates go through enzymatic degradation caused by the release of fibrinolytic factors, most notably tissue-type plasminogen activator (t-PA). There is constant play between t-PA and plasminogen-activator inhibitors. Surgical trauma usually decreases t-PA activity and increases plasminogen-activator inhibitors. When this happens, the fibrin in the fibrinous exudate is replaced by collagen. Blood vessels begin to form, which leads to the development of an adhesion. Once this has occurred, the adhesion is believed to be irreversible. Therefore, the balance between fibrin deposition and degradation during the first few days post-trauma is critical to the development of adhesions (Holmdahl L. *Lancet* 1999; 353: 1456-57). If normal fibrinolytic activity can be maintained or quickly restored, fibrous deposits are lysed and permanent adhesions can be avoided. Adhesions can appear as thin sheets of tissue or as thick fibrous bands.

Often, the inflammatory response is also triggered by a foreign substance in vivo, such as an implanted medical device. The body sees this implant as a foreign substance, and the inflammatory response is a cellular reaction to wall off the foreign material. This inflammation can lead to adhesion formation to the implanted device; therefore a material that causes little to no inflammatory response is desired.

Thus, the antimicrobial-containing biomaterial (e.g., coating or stand-alone film) can be used as a barrier to keep tissues separated to avoid the formation of adhesions, e.g., surgical adhesions. Application examples for adhesion prevention include abdominal surgeries, spinal repair, orthopedic surgeries, tendon and ligament repairs, gynecological and pelvic surgeries, and nerve repair applications. The antimicrobial-containing biomaterial may be applied over the trauma site or wrapped around the tissue or organ to limit adhesion formation. Other surgical applications of the antimicrobial-containing biomaterial-based film may include using the film as a dura patch, buttressing material, internal wound care (such as a graft anastomotic site), and internal drug delivery system. The antimicrobial-containing biomaterial (e.g., coating or stand-alone film) may also be used in applications in transdermal, wound healing, and non-surgical fields. The antimicrobial-containing biomaterial may be used in external wound care, such as a treatment for burns or skin ulcers. The antimicrobial-containing biomaterial may be used without any therapeutic agent as a clean, non-permeable, non-adhesive, non-inflammatory, anti-inflammatory dressing, or the antimicrobial-containing biomaterial may be used with one or more therapeutic agents for additional beneficial effects. In another embodiment, the antimicrobial-containing biomaterial is associated with bandage or dressing for a wound. When used in any of the aforementioned methods, the fatty acid-based material (in particle form or particles pressed into a film) may or may not be associated with a therapeutic agent.

In another embodiment, the antimicrobial-containing biomaterials provided herein can be used as a coating on a medical device to minimize the risk of these devices becoming colonized with bacteria during surgical implantation. The formulations described herein can also be spread onto a medical device surface and allowed to cure for a period of time, thereby providing a medical device coating comprising an antimicrobial-containing biomaterial. Examples of such devices include, but are not limited to, a graft, a catheter balloon, a stent or surgical mesh.

In still another embodiment, the antimicrobial-containing biomaterials provided herein (e.g., in the form of a stand-alone film) can be used for wound healing applications. The antimicrobial-containing biomaterials provided herein can also be used in combination with a bandage or dressing for wound healing applications. The term "wound" refers broadly to injuries to the skin and subcutaneous tissue initiated in any one of a variety of ways (e.g., pressure sores from extended bed rest, wounds induced by trauma, cuts, ulcers, burns and the like) and with varying characteristics.

Wounds are typically classified into one of four grades depending on the depth of the wound: (i) grade I: wounds limited to the epithelium; (ii) grade II: wounds extending into the dermis; (iii) grade III: wounds extending into the subcutaneous tissue; and (iv) grade IV (or full-thickness wounds): wounds wherein bones are exposed (e.g., a bony pressure point such as the greater trochanter or the sacrum). The antimicrobial-containing biomaterials described herein can be used for treatment of any of the aforementioned wounds.

The term "treat," "treated," "treating" or "treatment" includes the diminishment or alleviation of at least one symptom associated or caused by the state, disorder or disease being treated. For example, treatment can be diminishment of one or several symptoms of a disorder or complete eradication of a disorder (e.g., bacterial infection, tissue adhesion, and/or external wounds).

Various aspects and embodiments are further described by way of the following Examples. The Examples are offered by way of illustration and not by way of limitation.

EXAMPLES

The following examples are for demonstration purposes and are not meant to be limiting.

Example 1

Silver Fatty Acid Salts within the Fatty Acid-Derived Biomaterial

In accordance with the present invention, silver in its aqueous form was used to hydrate a fatty acid-derived biomaterial sample. One possible mechanism for the formation of the antimicrobial-containing biomaterial hydrated in aqueous silver is as follows: fish oil (triglycerides) absorbs oxygen into the oil; oxidation of the C=C bonds in the oil occurs; fatty acid and glycerides (a mixture of mono, di- and tri) are formed; continued curing results in dehydration of neighboring carboxyl and hydroxyl functional groups; lactone/ester cross-links are formed between fatty acids and glycerides; the oil solidifies into a bioabsorbable gel containing cross-linked fatty acids and glycerides; the cross-linked fatty acid biomaterial is immersed in an aqueous Ag solution; and the hydrated silver coated fatty acid biomaterial is dried to evaporate the solvent.

The silver hydrated fatty acid-derived biomaterial was prepared as follows.

Figure 3:
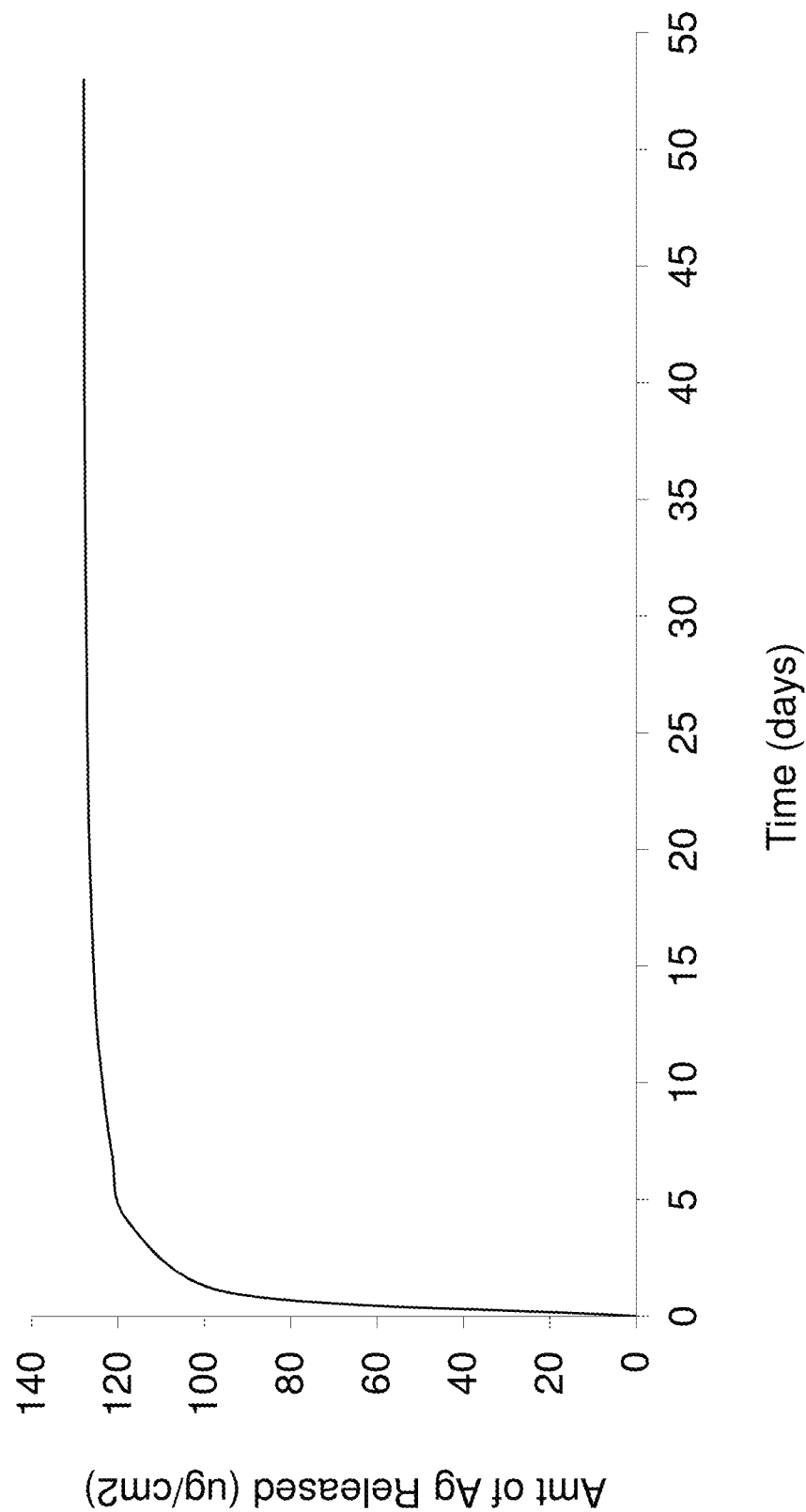
FIG. 3 illustrates the silver release profile of the fatty acid-derived biomaterial coating hydrated in silver acetate over 4 hours.
Figure 4:
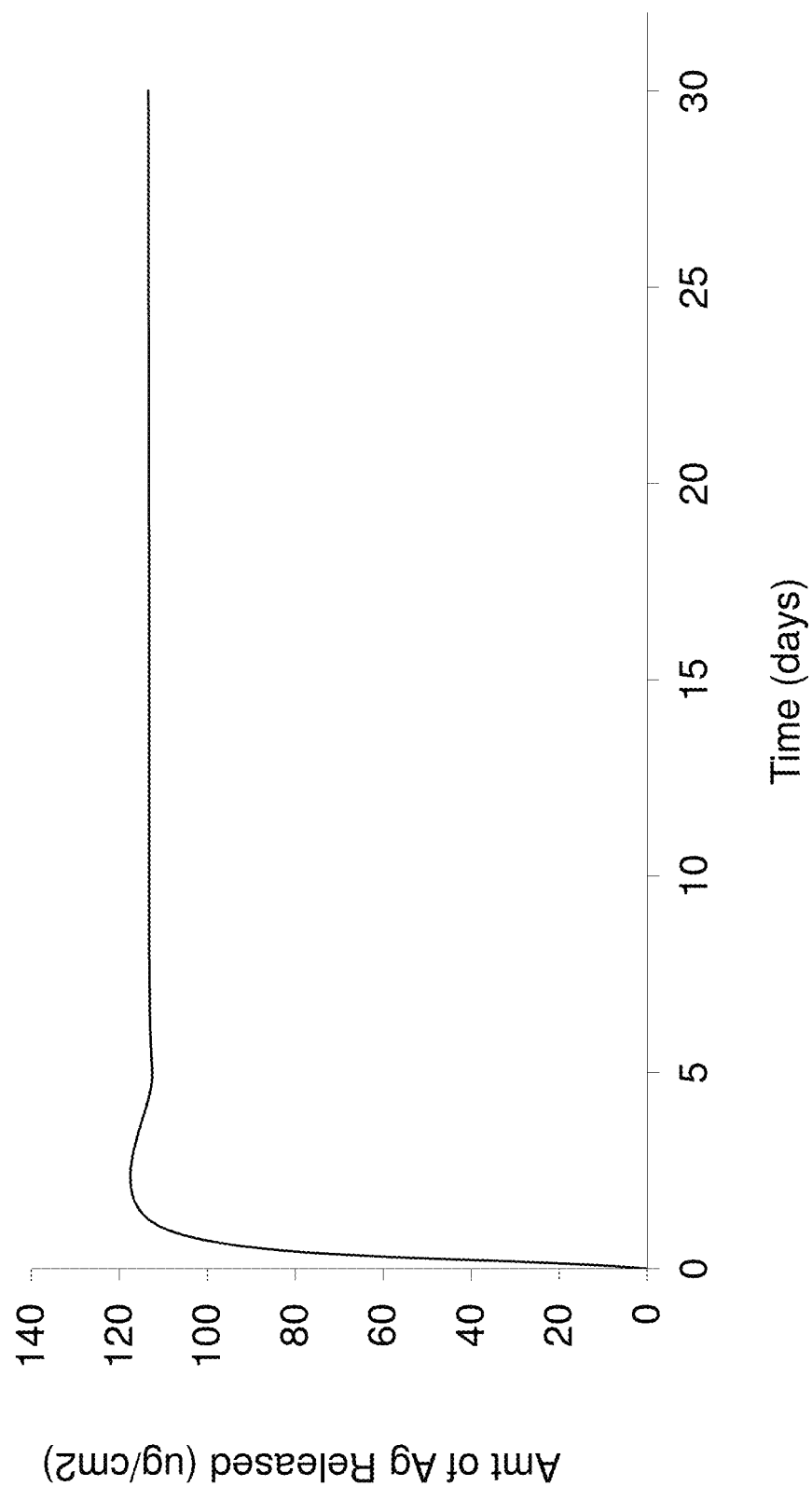
FIG. 4 illustrates the silver release profile of the fatty acid-derived biomaterial coating hydrated in silver nitrate over 4 hours.

Aqueous silver acetate was massed and dissolved to a final concentration of 0.06M. In addition, a fatty acid biomaterial was prepared by curing native fish oil, at a density of approximately 100 mg/inch$^2$, onto polypropylene mesh at a temperature of 200° F. for 24 hours to form a solid coating. To incorporate silver by hydration, a 1 inch$^2$ sample of the fatty acid biomaterial was then immersed in the 0.06M aqueous silver acetate solution for four hours. By immersing the sample in aqueous silver, the fatty acid biomaterial becomes hydrated in an aqueous environment over an extended period of time allowing for the formation of silver fatty acid salts. Determination of free silver content released in $\mu g/cm^2$ from the silver hydrated fatty acid biomaterial sample was carried out in water and analyzed by Inductively Coupled Plasma (ICP). The silver release profile obtained is shown in FIG. 3. The results indicate that an immediate burst of silver is released from the hydrated fatty acid-derived coating. Similarly, FIG. 4 shows the silver release profile of silver from a 1 inch$^2$ fatty acid-derived biomaterial sample hydrated in 0.07M silver nitrate. The free silver released from the silver nitrate hydrated sample also occurs as a burst indicating that high levels of silver would be released rapidly in an aqueous environment.

Figure 5:
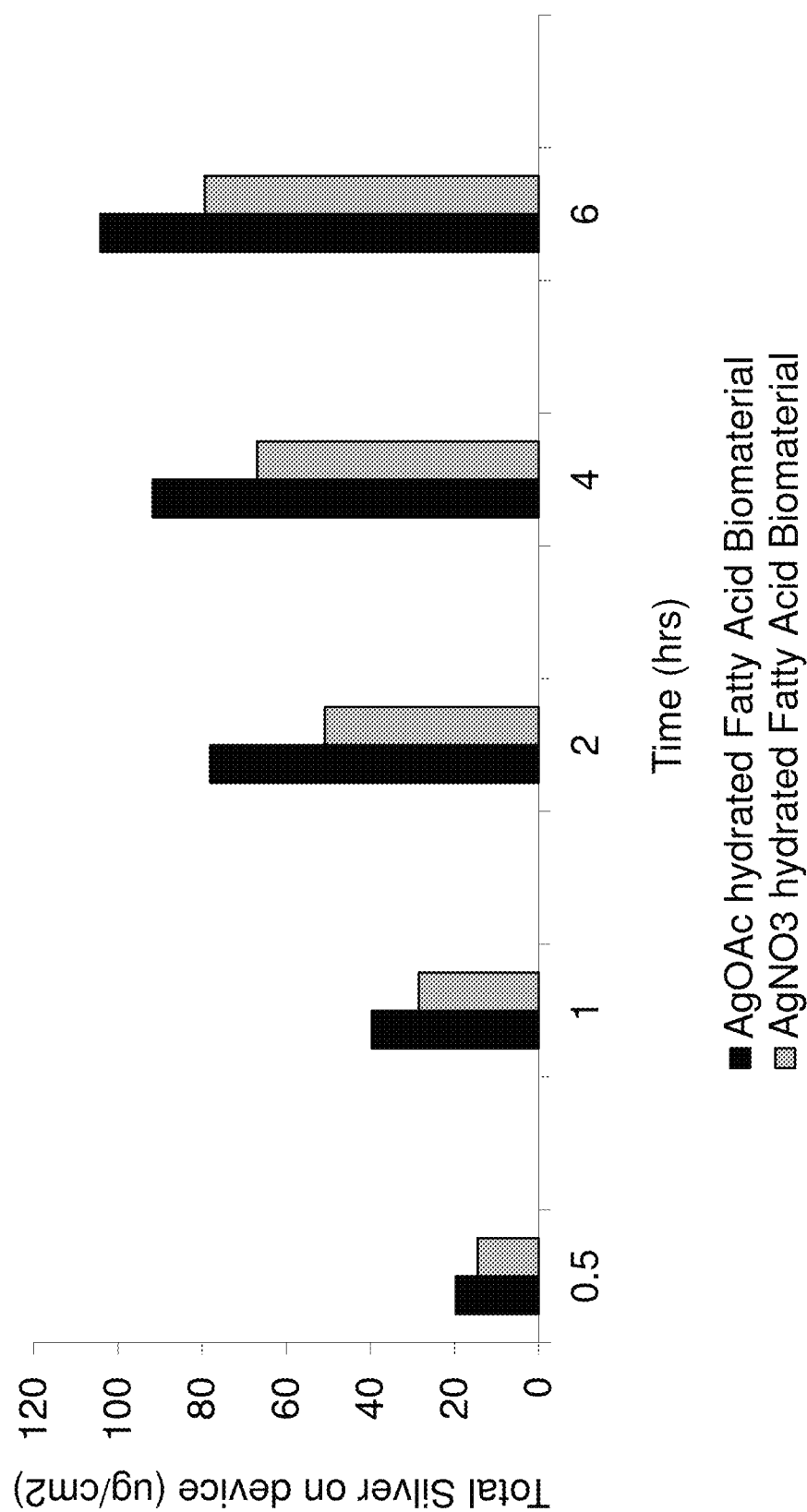
FIG. 5 depicts a bar graph of the total silver in $\mu g/cm^2$, assayed from Fatty Acid Biomaterial samples hydrated in aqueous silver nitrate and aqueous silver acetate over a period of 6 hours.
Figure 6A:
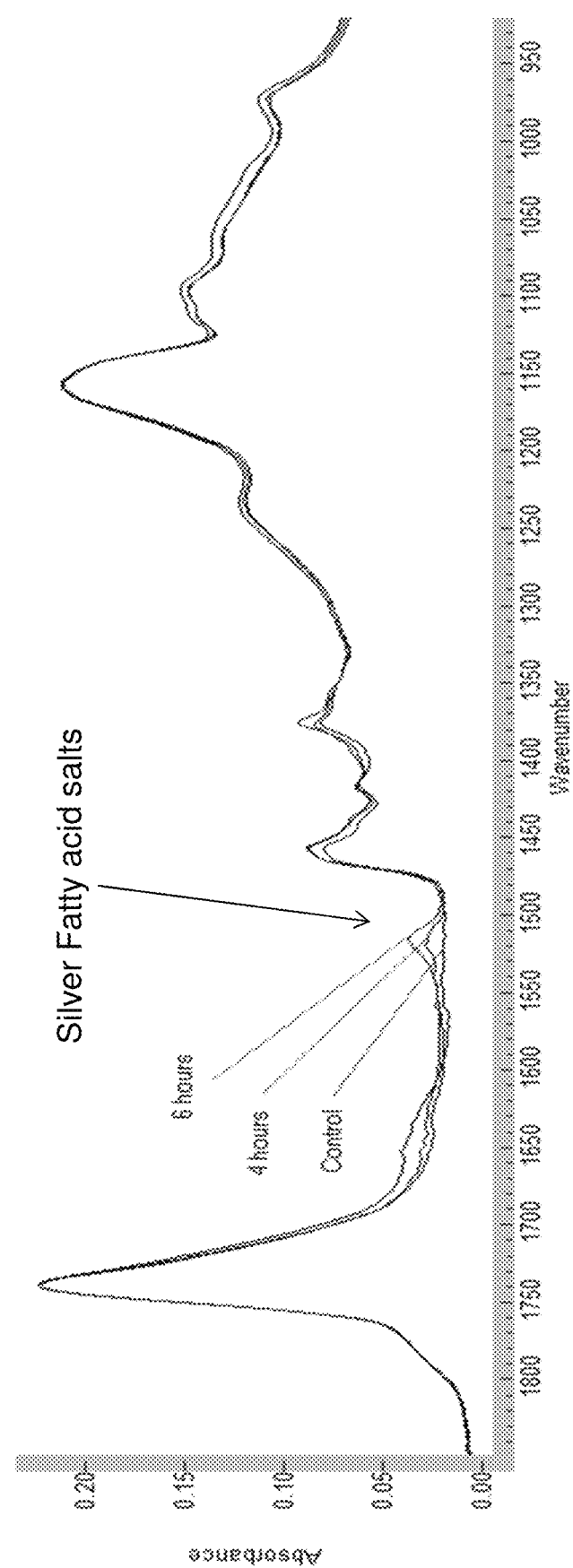
FIGS. 6A-6B represent FTIR analysis of fatty acid-derived biomaterial samples hydrated in silver nitrate and silver acetate between the regions of 900-1850 $cm^{-1}$ illustrating an increase in silver fatty acid salts with increased hydration time as indicated by the peaks at 1512 $cm^{-1}$.
Figure 6B:
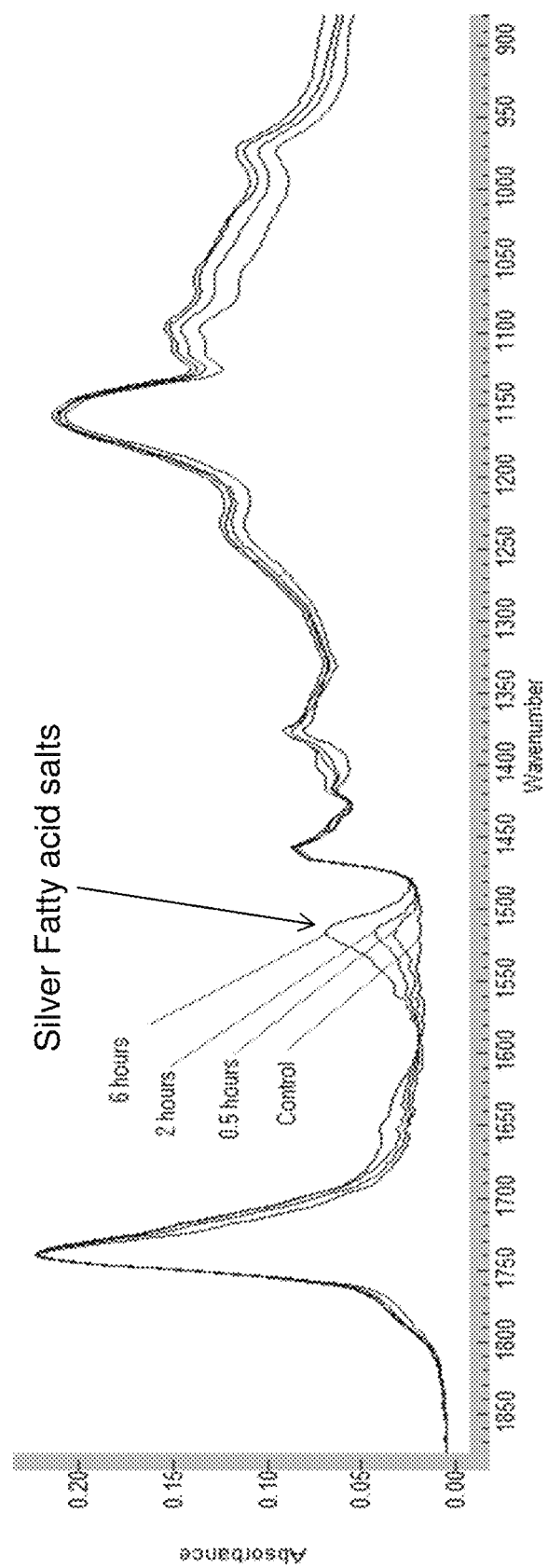

Silver assay of fatty acid-derived biomaterial samples hydrated in silver acetate and silver nitrate over a six hour period was performed by ICP. FIG. 5 illustrates that the silver content in a fatty acid-derived biomaterial sample increases as a function of hydration time using aqueous silver nitrate or aqueous silver acetate as the hydration media. A greater amount of silver was able to be loaded using silver acetate than silver nitrate within the same hydration time as result of the additional penetration of the silver acetate into the coating due to the higher pH and the similarity of the acetate group to the fatty acid components within the coating. Analysis of the silver hydrated fatty acid-biomaterial samples by FTIR, shows evidence of the formation of fatty acid represented by the peak at $1512 \text{ cm}^{-1}$, which increases with increasing hydration time as shown in FIGS. 6A-6B for silver nitrate and silver acetate loading solutions, respectively.

Figure 7:
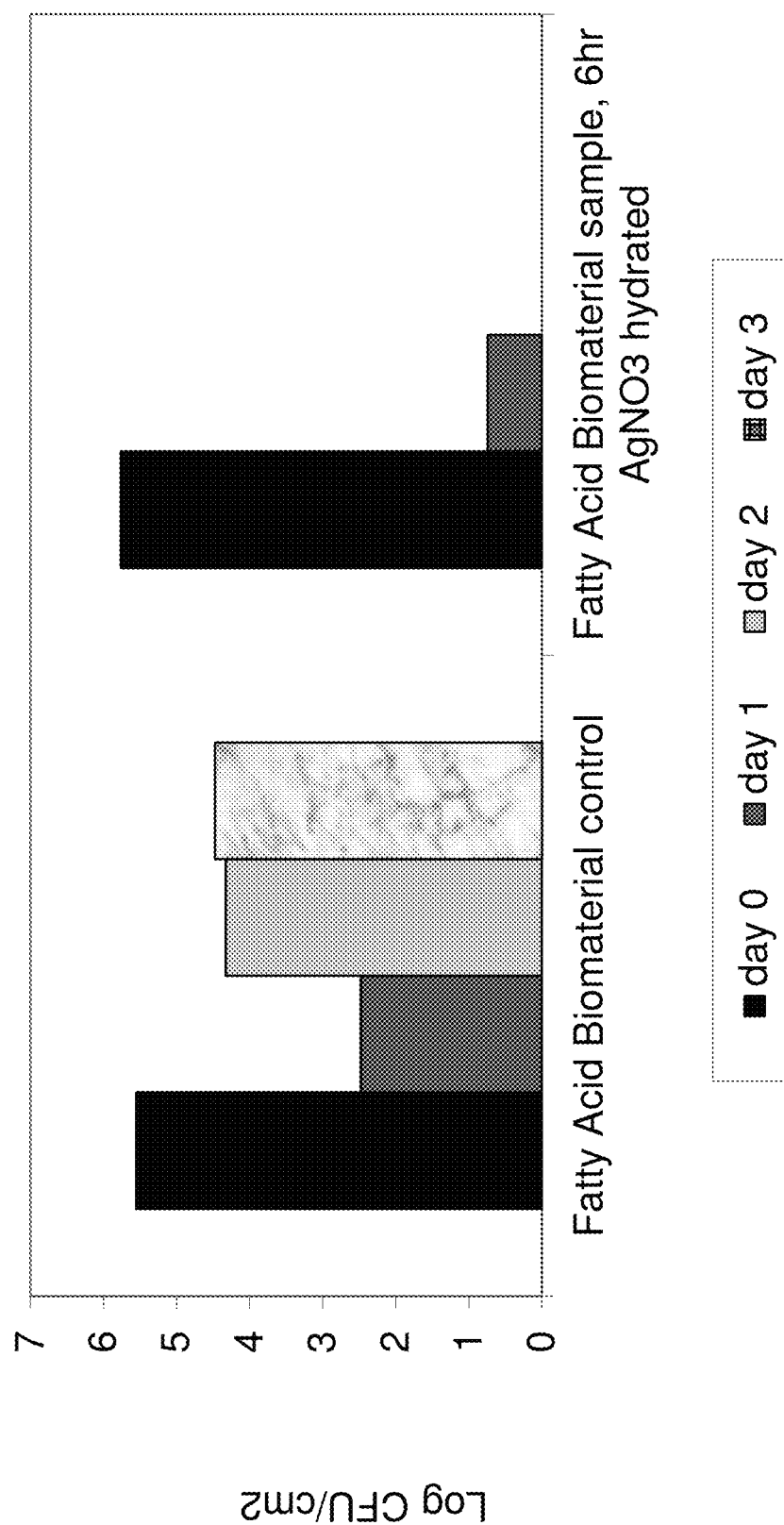
FIG. 7 is a bar graph of the recorded log reduction of colony forming units per $cm^2$ of silver nitrate hydrated fatty acid-derived biomaterial samples against a control fatty acid-derived biomaterial in a three day in-vitro S. aureus biofilm study.

The efficacy of the silver nitrate hydrated fatty acid-derived biomaterial was tested in a three day in-vitro *S. aureus* biofilm study. A fatty acid-derived biomaterial sample, without silver present, was used as a control and the results obtained are shown in FIG. 7. These results show the silver hydrated sample had an approximate 5 log reduction in colony forming units (CFU's) per $cm^2$ after one day and no CFU's were present on days 2 and 3. The fatty acid-derived biomaterial control sample had an approximate 3 log reduction in CFU's after day one as a result of the antibacterial properties of short-chain fatty acids (T. Kitahara, "Biol Pharm. Bull.: Second Edition." 2004, Vol 27(9), pgs 1321-1326) but the CFU's gradually increased on day 2 and 3. FIG. 7 demonstrates that adding silver to the fatty acid-derived biomaterial coating through hydration in aqueous silver media enhances the coating's ability to form a biofilm within an in-vitro *S. aureus* infected environment.

Example 2

Fatty Acid-Derived Biomaterial Surface Coated with Silver

In a different embodiment of the present invention, silver was coated onto the surface of a fatty acid-derived biomaterial. Sample preparation was done as follows.

Silver nitrate was massed and dissolved in methanol to a final concentration of 0.02M. In addition, a fatty acid biomaterial was prepared by encapsulating polypropylene mesh with approximately 100 mg of fish oil per $inch^2$ then thermally curing the fish oil cast onto the polypropylene mesh at a temperature of 200° F. for 24 hours to form a solid fatty acid-derived coating. To incorporate silver on the surface, a 1 $inch^2$ sample of the fatty acid biomaterial was then sprayed onto the surface with the 0.02M silver nitrate solution and allowed to dry to evaporate off the methanol solvent. One possible mechanism for the formation of the antimicrobial-containing biomaterial coated with aqueous silver is as follows: fish oil (triglycerides) absorbs oxygen into the oil; oxidation of the C=C bonds in the oil occurs; fatty acid and glycerides (a mixture of mono, di- and tri) are formed; continued curing results in dehydration of neighboring carboxyl and hydroxyl functional groups; lactone/ester cross-links are formed between fatty acids and glycerides; the biomaterial solidifies into a bioabsorbable gel containing cross-linked fatty acids and glycerides; the cross-linked fatty acid biomaterial is sprayed with an aqueous Ag solution; and the sprayed silver coated fatty acid biomaterial is dried to evaporate the solvent.

Figure 8:
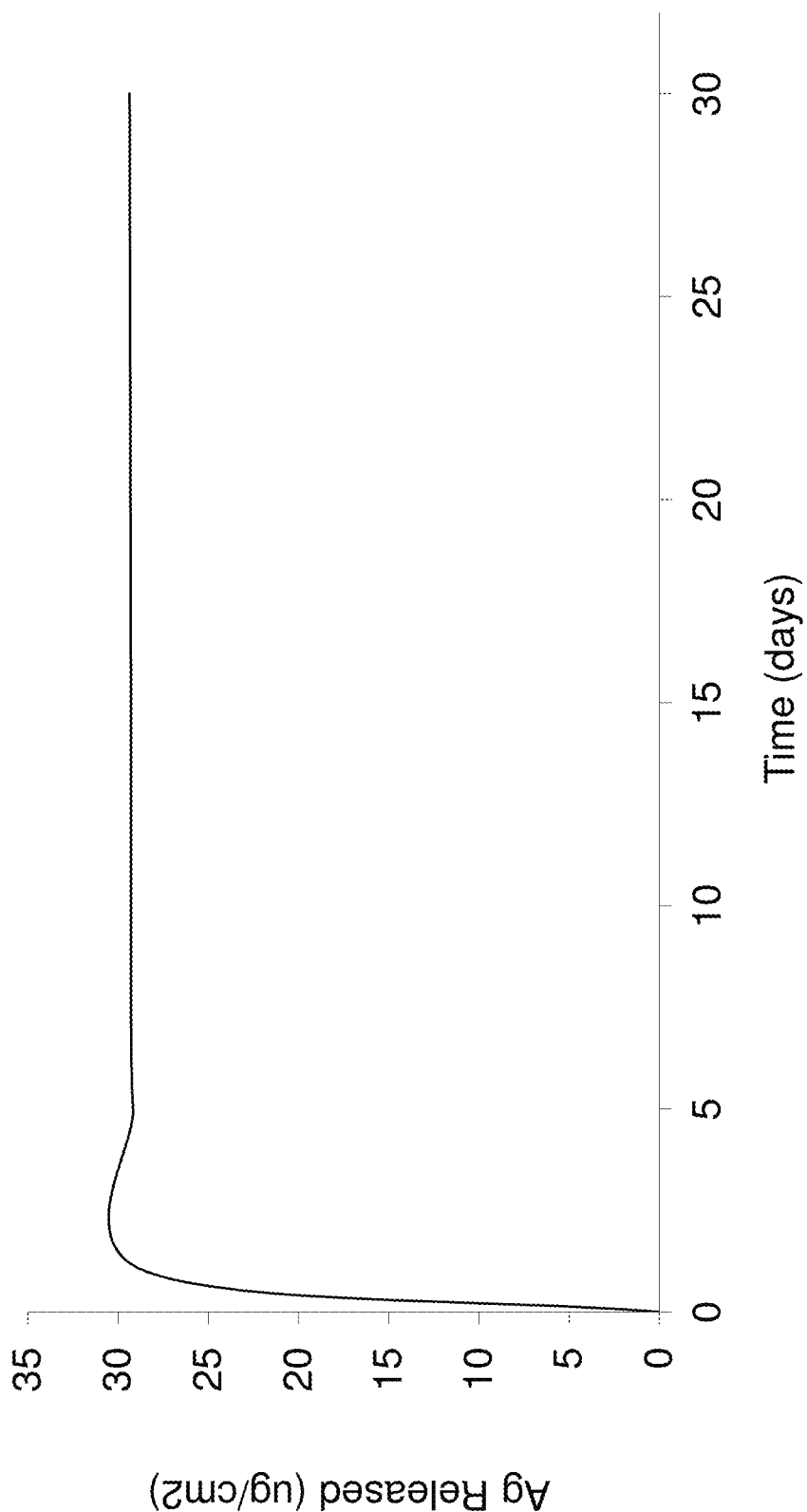
FIG. 8 illustrates the silver release profile of a fatty acid-derived biomaterial sample spray coated with layer of silver.

The silver release properties of a fatty acid-derived monofilament coated biomaterial sprayed with silver nitrate was evaluated in water. The silver content in the dissolution media was analyzed over 30 days by ICP. FIG. 8 shows the silver amounts released into aqueous media depicting a dose dump of silver in the dissolution media. The silver release profile of the sprayed fatty acid-derived biomaterial is similar to the silver hydrated fatty acid-derived biomaterial in FIGS. 3-4.

Figure 9:
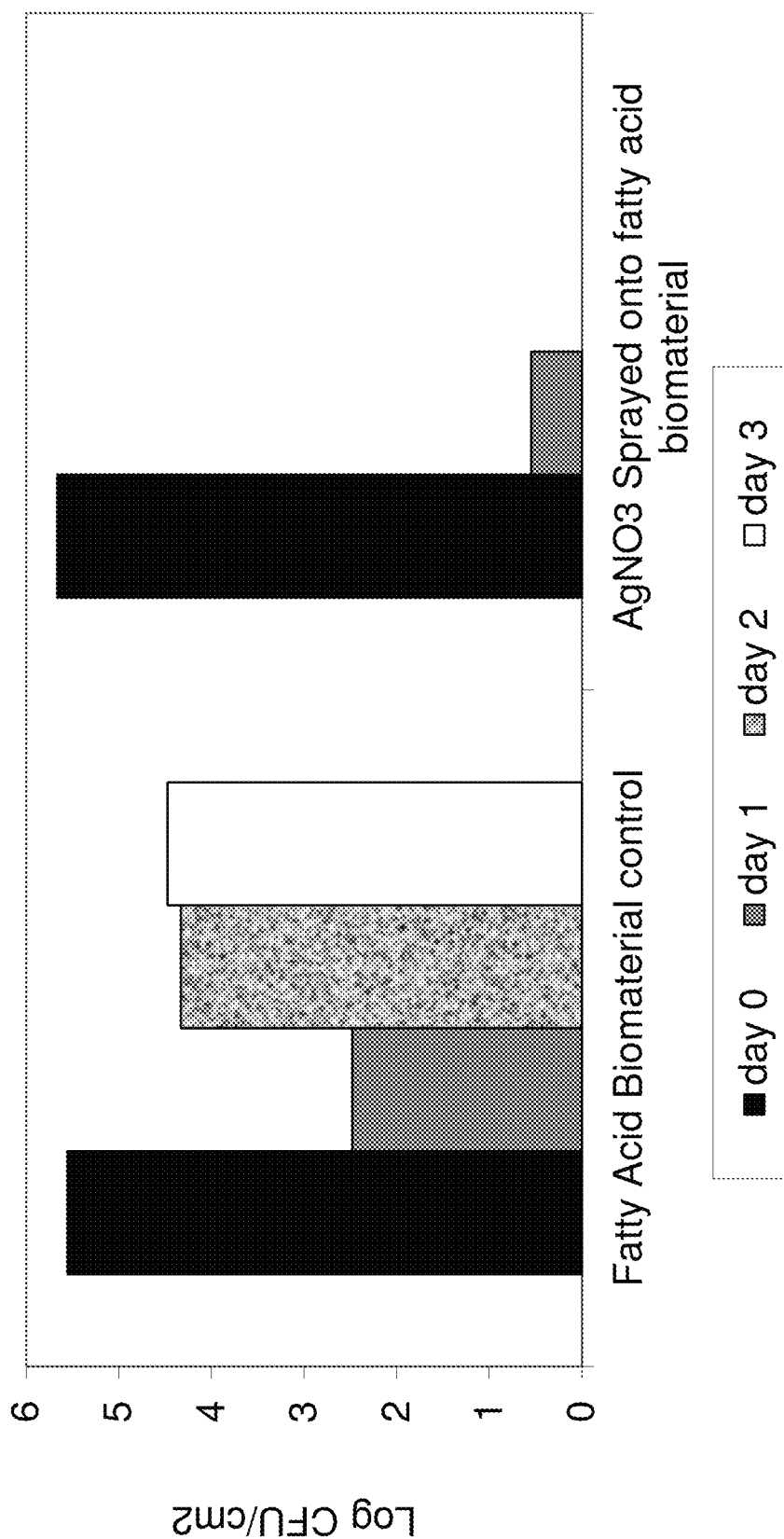
FIG. 9 depicts a bar graph of the log reduction of colony forming units per $cm^2$ of a fatty acid-derived biomaterial sample coated with a layer of silver together with a control fatty acid-derived biomaterial sample in a three day in-vitro S. aureus biofilm study.

Results illustrating the efficacy of the fatty acid-derived biomaterial sprayed with a layer of silver in a three day in-vitro *S. aureus* biofilm study are shown in FIG. 9. A 5 log reduction in colony forming units (CFU's) per $cm^2$ was noted after one day and no CFU's were present on days 2 and 3. The fatty acid-derived biomaterial control sample had an approximate 3 log reduction in CFU's after day one but the CFU's per $cm^2$ gradually increased on day 2 and 3 indicating that the addition of the surface silver layer on the fatty acid-derived biomaterial helped reduce the formation of a biofilm in this 3 day in-vitro study.

Example 3

Formation of Reduced Silver within the Fatty Acid-Derived Biomaterial

In this example, a different method of forming a silver coated fatty acid-derived material is described. The method of preparation is as follows:

Three components are used to make up a silver-containing fatty acid emulsion formulation which is then thermally cured onto polypropylene mesh to form a solid reduced silver fatty acid-derived biomaterial coating. The three components that make up the emulsion include an aqueous silver solution, native fish oil and partially cured fish oil that has a viscous consistency. An aqueous silver solution was prepared by massing silver nitrate or silver acetate and dissolving it in water to give final concentrations of 0.07M and 0.06M respectively. Separately, partially cured fish oil was prepared by exposing native fish oil to temperatures of approximately 90° C. in the presence of oxygen for 16 hours which results in a partially cured fish oil component with a viscous consistency. The silver containing emulsion is then prepared by massing out (w/w) 45% of the native fish oil, 45% of the partially cured fish oil and 10% of the aqueous silver solution in one vial and thoroughly mixing these components with intermittent heating. The emulsified silver formulation is then cast onto a medical device and thermally cured at 200° F. for approximately 24 hours to form a solid reduced silver fatty acid-derived biomaterial coating. Thermal curing is hypothesized to convert the aqueous silver present in the coating to an insoluble form of silver within the fatty acid-derived coating. This is accomplished by the interaction of the silver ions in the silver nitrate solution with the lipid hydroperoxides formed during the oxidation of the oil-derived cross-linked gel, which are then reduced to silver metal (A. Kumar et al., "Nature Materials". 2008 Vol 7, pgs 236-241). One possible mechanism for the formation of the biomaterial coating containing reduced silver is as follows: emulsified fish oil, pre-cured fish oil and silver (Ag) absorb oxygen; oxidation of the C=C bonds in the oil occurs; fatty acid and glycerides (mixture of mono, di- and tri) and reduced silver are formed; continued curing results in dehydration of neighboring carboxyl and hydroxyl functional groups; lactone/ester cross-links are formed between fatty acids and glycerides; and the material solidifies into a bioabsorbable gel containing cross-linked fatty acids, glycerides and reduced Ag.

Figure 10:
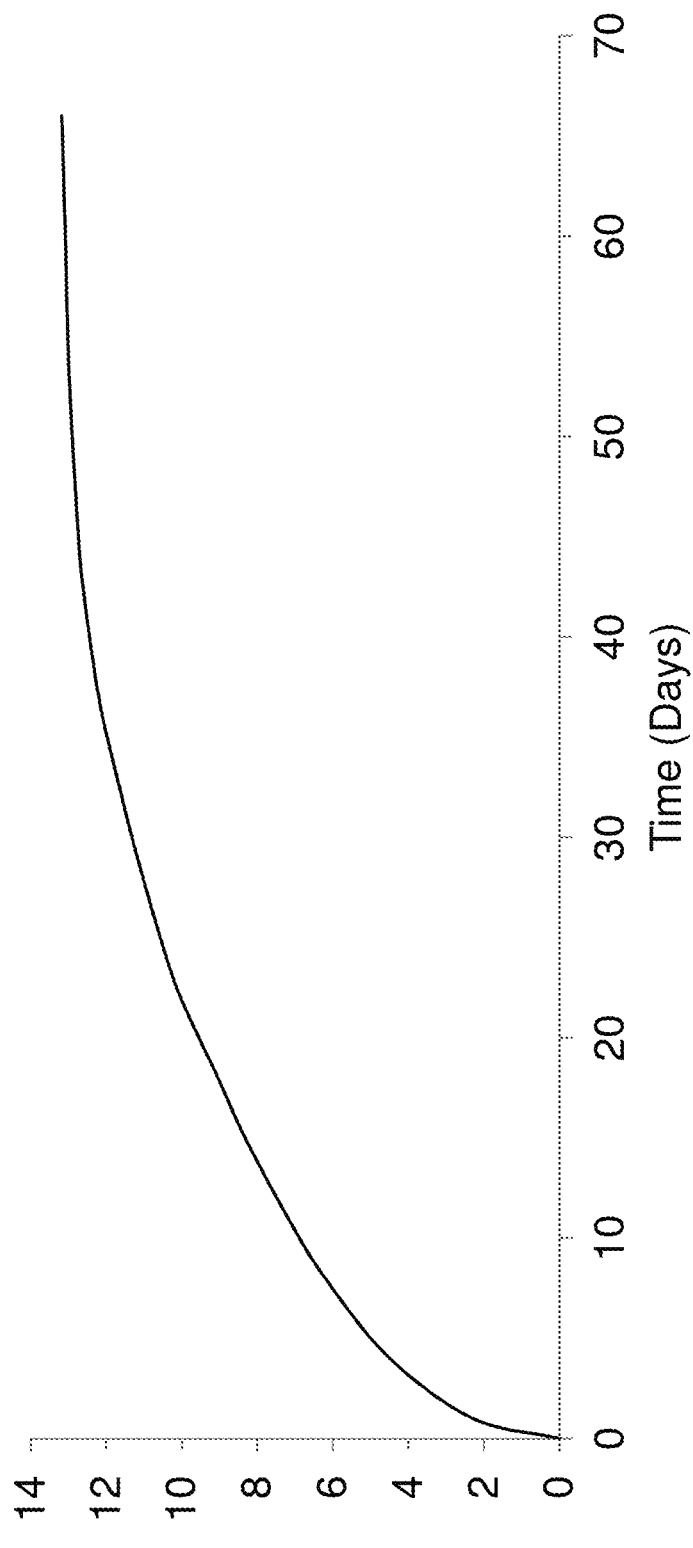
FIG. 10 illustrates the silver release profile in $\mu g/cm^2$ of a fatty acid-derived biomaterial sample incorporated with reduced silver.

The silver release profile of a reduced silver fatty acid-derived coating was evaluated in water as the dissolution media. ICP was used to analyze the free silver content in the dissolution media for a period of approximately two months. Silver released in $\mu g/cm^2$ over time is depicted in FIG. 10. Silver is released in steady gradual manner over an extended amount of time in water indicating that the aqueous silver that was cured with the fatty acid-derived biomaterial is converted to an insoluble form. In an aqueous environment, a reduced silver fatty acid-derived biomaterial sample would release low levels of silver unlike Examples 1 and 2 where a rapid burst of silver is released in an aqueous environment.

Figure 11:
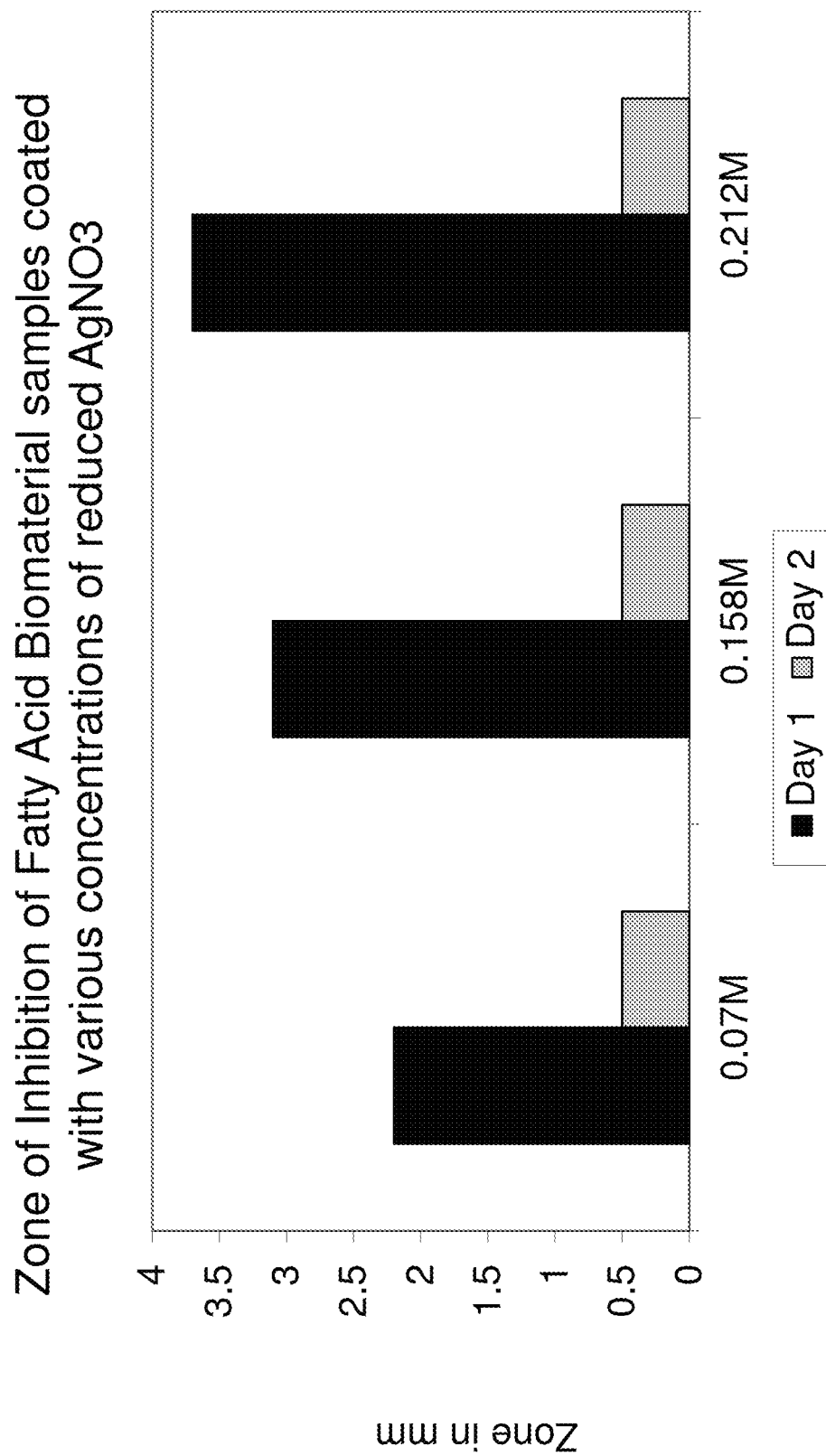
FIG. 11 graphically depicts different zone sizes in mm in a zone of inhibition in-vitro study achieved from fatty acid-derived biomaterial samples prepared with different concentrations of reduced silver.
Figure 12:
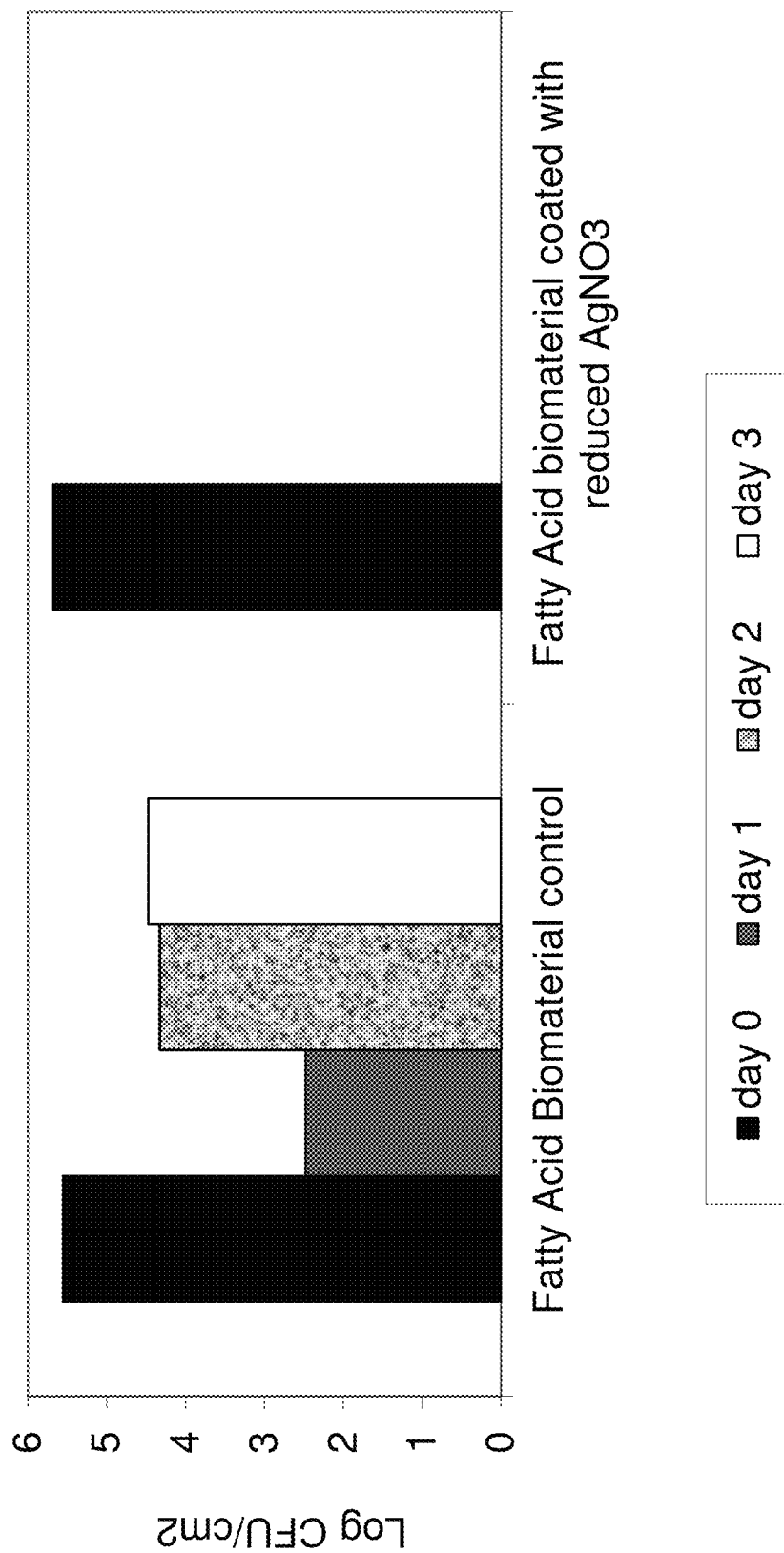
FIG. 12 depicts a bar graph of the log reduction of colony forming units per $cm^2$ of a fatty acid-derived biomaterial sample incorporated with reduced silver together with a control fatty acid-derived biomaterial sample in a three day in-vitro S. aureus biofilm study.

The reduced silver fatty acid-derived biomaterial was tested for its bactericidal properties in a 2 day *S. aureus* zone of inhibition assay using samples prepared using increasing concentrations of aqueous silver nitrate. FIG. 11 shows the graphical results of the zone of inhibition assay. Zones measured on day 1 were found to be larger in samples prepared from a higher concentration of silver. This demonstrates that the silver added to the fatty acid-derived biomaterial is responsible for the growth inhibiting effects observed. Day 2 of the zone assay had a comparable size in all three samples tested. Similarly, a biofilm assay was performed on a reduced silver fatty acid-derived biomaterial sample and found to have no bacteria on the surface of the device after three days as shown in FIG. 12. The overall reduction in CFU's was approximately 5 log.

Figure 13:
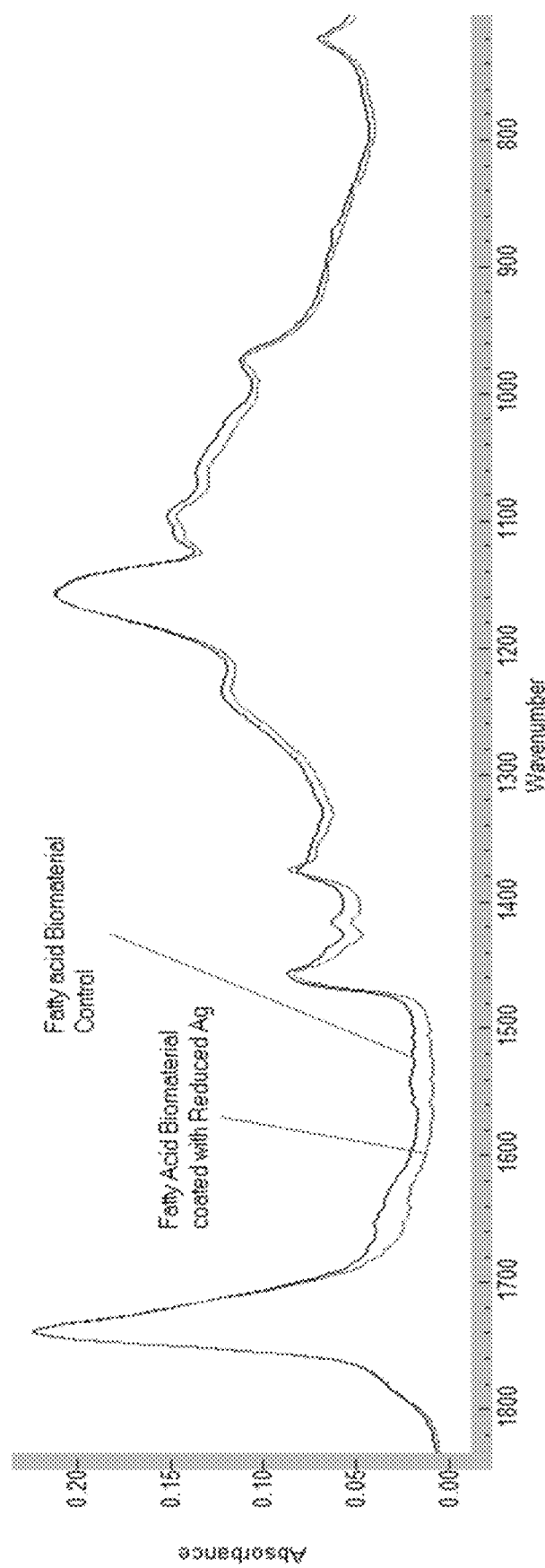
FIG. 13 represents FTIR analysis of fatty acid-derived biomaterial with reduced silver and a fatty acid-derived biomaterial control between the regions of 800-1800 $cm^{-1}$ without the presence of the silver fatty acid peak at approximately 1512 $cm^{-1}$, showing a variation of the samples analyzed in FIGS. 9A and 9B.

FTIR analysis of the reduced silver coating is shown in FIG. 13. The spectra of the fatty acid biomaterial control and the reduced silver fatty acid sample have similar spectral profiles and do not show the presence of fatty acid salts as seen in FIGS. 6A-6B indicating that the aqueous silver in these samples interacts differently after the thermal curing process.

Example 4

Formation of Silver Nanoparticle Fatty Acid-Derived Biomaterial

Figure 14:
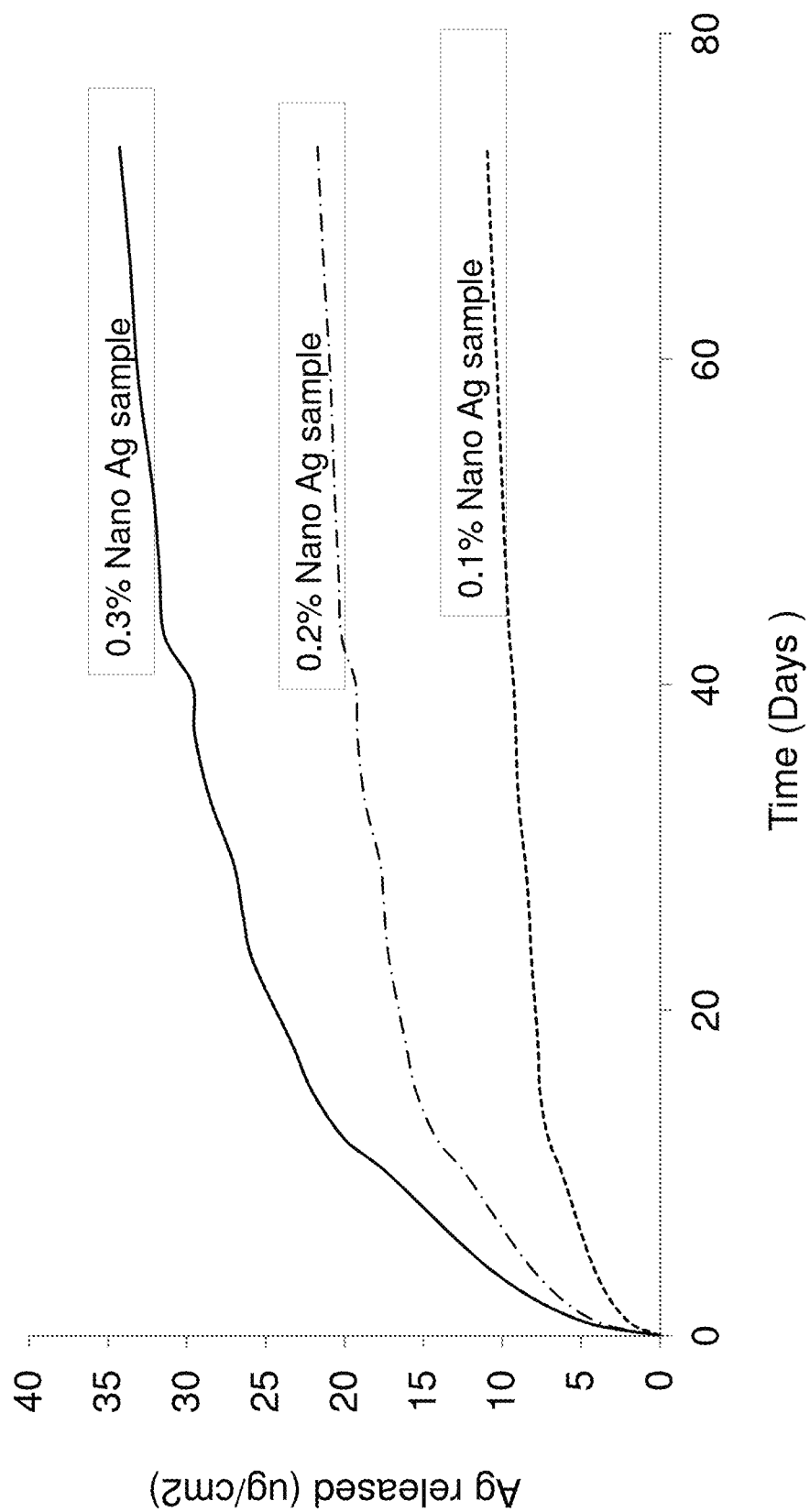
FIG. 14 depicts silver release data of the silver nanoparticle coated fatty acid-derived biomaterial in aqueous media as described in Example 3.
Figure 20:
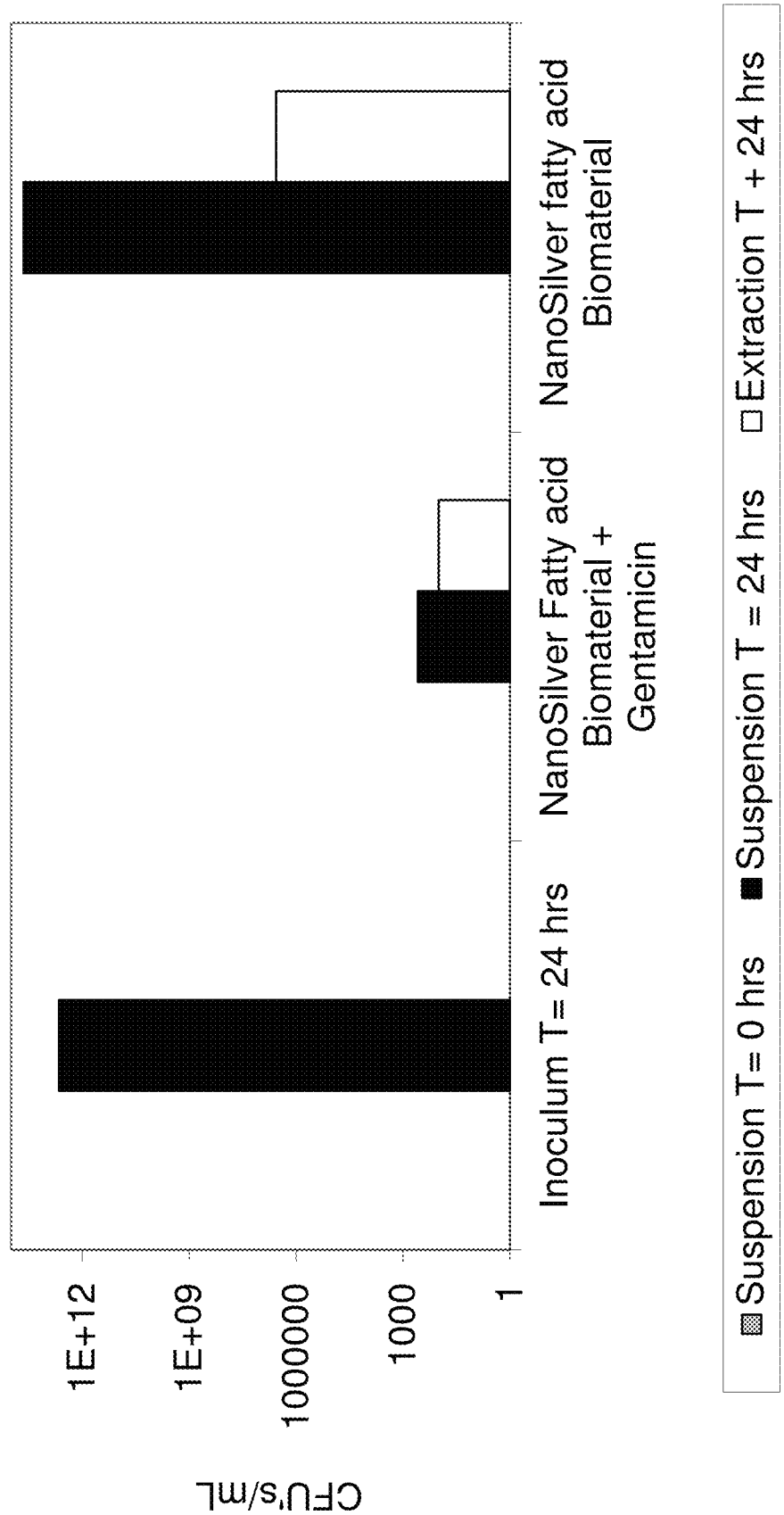
FIG. 20 illustrates a bar graph of the colony forming units per mL enumerated by extracting samples of a Silver nanoparticle fatty acid-derived biomaterial surface coated with gentamicin, a Silver nanoparticle fatty acid-derived biomaterial and a fatty acid-derived biomaterial control in a bacterial adherence study as described in Example 5.

In a different embodiment of this invention, elemental silver is used in the form of silver nanoparticles and added to a fatty acid biomaterial to in order to enhance antibacterial properties of the fatty acid biomaterial coating. The sample preparation was done as follows:

Silver nanopowder surface coated with oleic acid was purchased from American Elements, 99.9% silver metal. A fish oil and silver nanopowder formulation was then prepared by mixing 1% silver nano powder in 99% fish oil (w/w). The fish oil and silver nanopowder was thoroughly mixed in a sonication bath for an hour then cast onto a medical device and thermally cured at 200° F. for 24 hours to form a solid coating. One possible mechanism for the formation of the nano-silver coated biomaterial coating is as follows: fish oil and silver nanoparticles absorb oxygen; oxidation of the C=C bonds in the oil occurs; fatty acid and glycerides (mixture of mono, di- and tri) are formed; continued curing results in dehydration of neighboring carboxyl and hydroxyl functional groups; lactone/ester cross-links are formed between fatty acids and glycerides; and the material solidifies into a bioabsorbable gel containing cross-linked fatty acids, glycerides and Ag nano particles The silver release properties of the silver nanoparticle fatty acid biomaterial samples in water are shown in FIG. 14. The release profiles indicate that more silver is released as a function of the concentration of silver nanoparticles added to the fatty acid biomaterial coating. The silver nanoparticles in the fatty acid biomaterial coating also produces a steady controlled release of silver in aqueous media over a period of approximately 75 days. The release profiles in FIG. 20 are an improvement to the quick burst of silver released when silver is sprayed onto the fatty acid-derived biomaterial or hydration method is used to incorporate silver fatty acid salts into the coating as described in Example 1 and 2.

Figure 15:
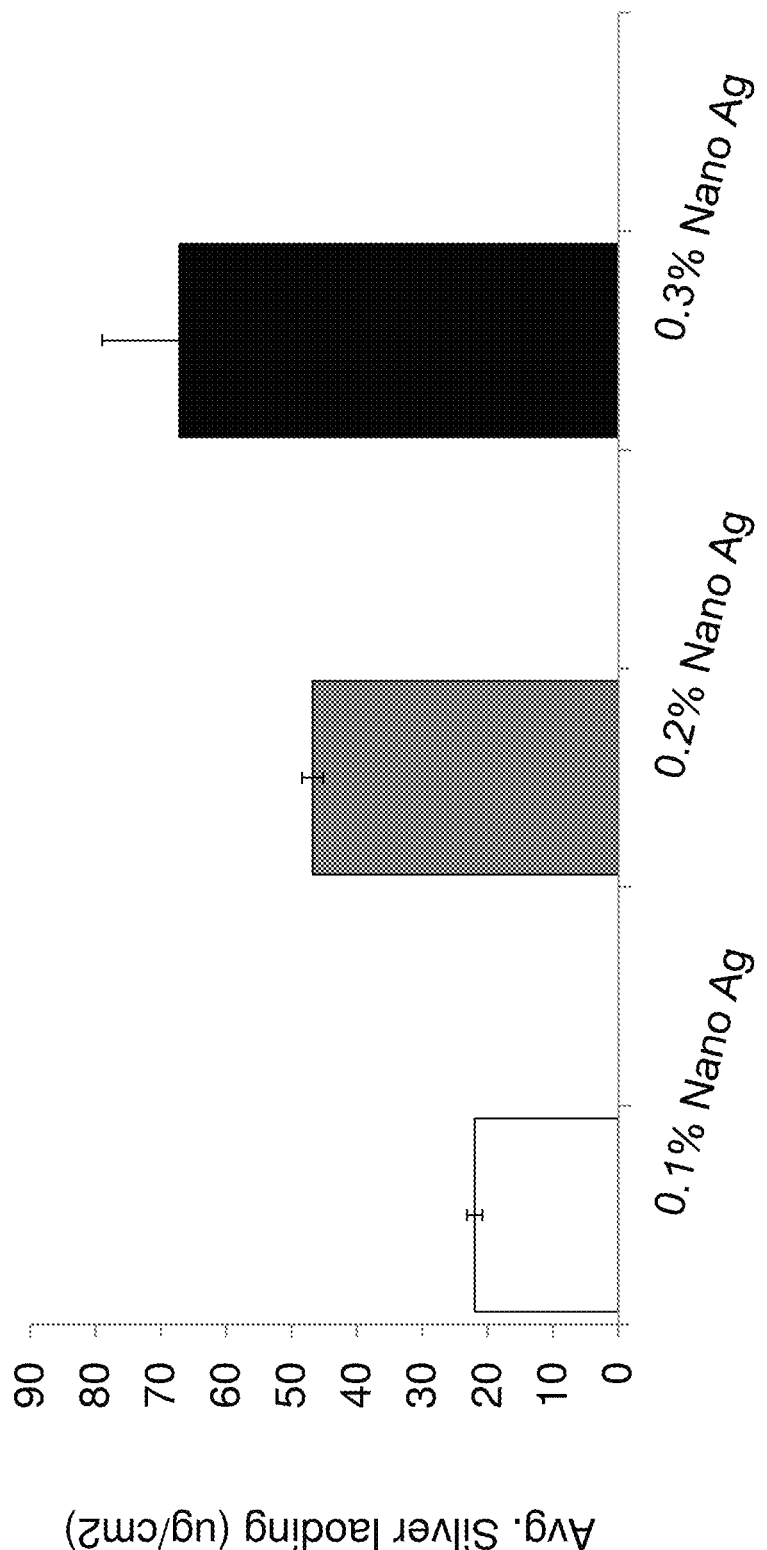
FIG. 15 illustrates the silver assay loading of different samples with different concentrations of silver nanoparticles in the fatty acid-derived biomaterial coating as discussed in Example 4.

The amount of silver loaded into the fatty acid-derived biomaterial was determined by ICP. The amounts of silver loaded within the fatty acid biomaterial can be controlled by altering the concentration of the silver nanoparticles in the coating as shown in FIG. 15.

In a related method of this embodiment, a silver nanoparticle fatty acid-derived film can be prepared separately and cast onto a medical device to produce a variation of the mechanism described in FIG. 13. One possible mechanism for the formation of the silver nanoparticle-containing biomaterial coating is as follows: fatty acid film particles and silver nanoparticles are thoroughly mixed together; the blended particles and Ag nanoparticles are pressed into a thin film under heat and pressure; and the fatty acid silver nanoparticle film is cast onto a polymeric device.

Figure 16:
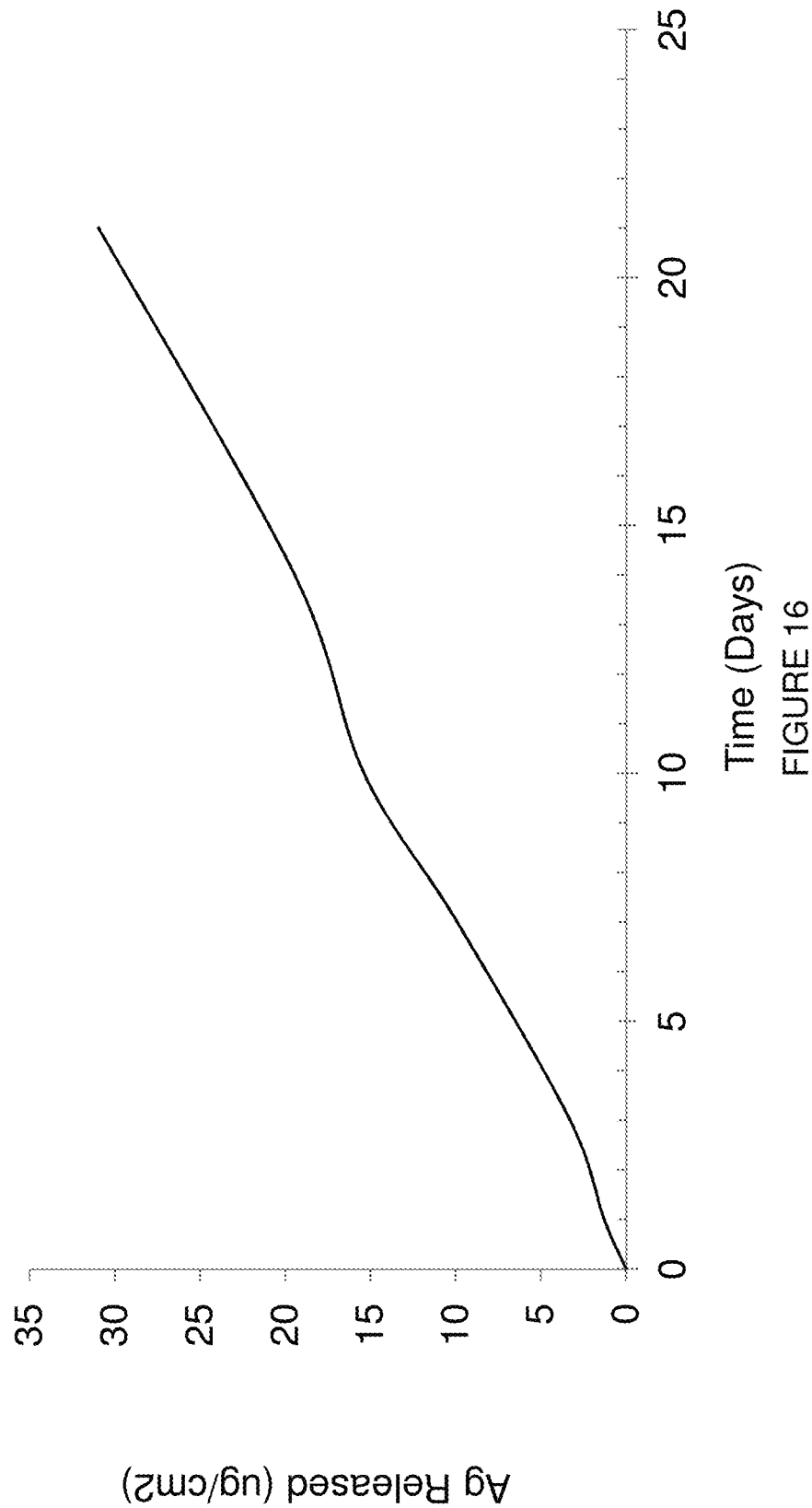
FIG. 16 depicts silver release data of the silver nanoparticle fatty acid film-derived biomaterial as described in Example 3.

The silver release profile of this embodiment is shown in FIG. 16, which also shows a sustained release profile in an aqueous environment.

Example 5

Formation of Silver Nano-Particle Fatty Acid-Derived Biomaterial in Combination with Gentamicin Sulfate In this embodiment, the silver nanoparticle fatty acid-derived biomaterial coating is combined with a pharmaceutical agent such as gentamicin to enhance microbial stasis.

Silver nanopowder surface coated with oleic acid was purchased from American Elements (Product Number AG-M-03M-NPC), 99.9% silver metal. gentamicin sulfate was purchased from Spectrum Chemicals and Laboratory Products, part number G1174. The fish oil and silver nanopowder formulation was then prepared by mixing 0.16% silver nano powder and 2.57% gentamicin sulfate powder in 97% fish oil (w/w). The gentamicin sulfate, silver nanopowder and fish oil was then thoroughly mixed using a cryo-grinding apparatus under cryogenic temperatures forming a cryoground formulation containing fish oil gentamicin and silver. Cryogenic grinding (cryogrinding) is a process carried out at extremely low temperatures enabled by using liquid nitrogen (−196° C.), to finely pulverize and mix sample components by means of a magnetic grinding mechanism, making the sample brittle under these low temperatures, thereby yielding a thoroughly mixed homogenous formulation. A Cryogenic impact grinder (6750 Freezer Mill) was used for homogenizing a fish oil, gentamicin and silver formulation. The cryogenic grinding apparatus' tub was filled with 4-5 L of liquid nitrogen and set to grind for eight cycles. Each cycle consists of 2 minutes of grinding with a 2 minute cooling period at a rate of 15 impacts per second during the grinding cycle.

Figure 17:
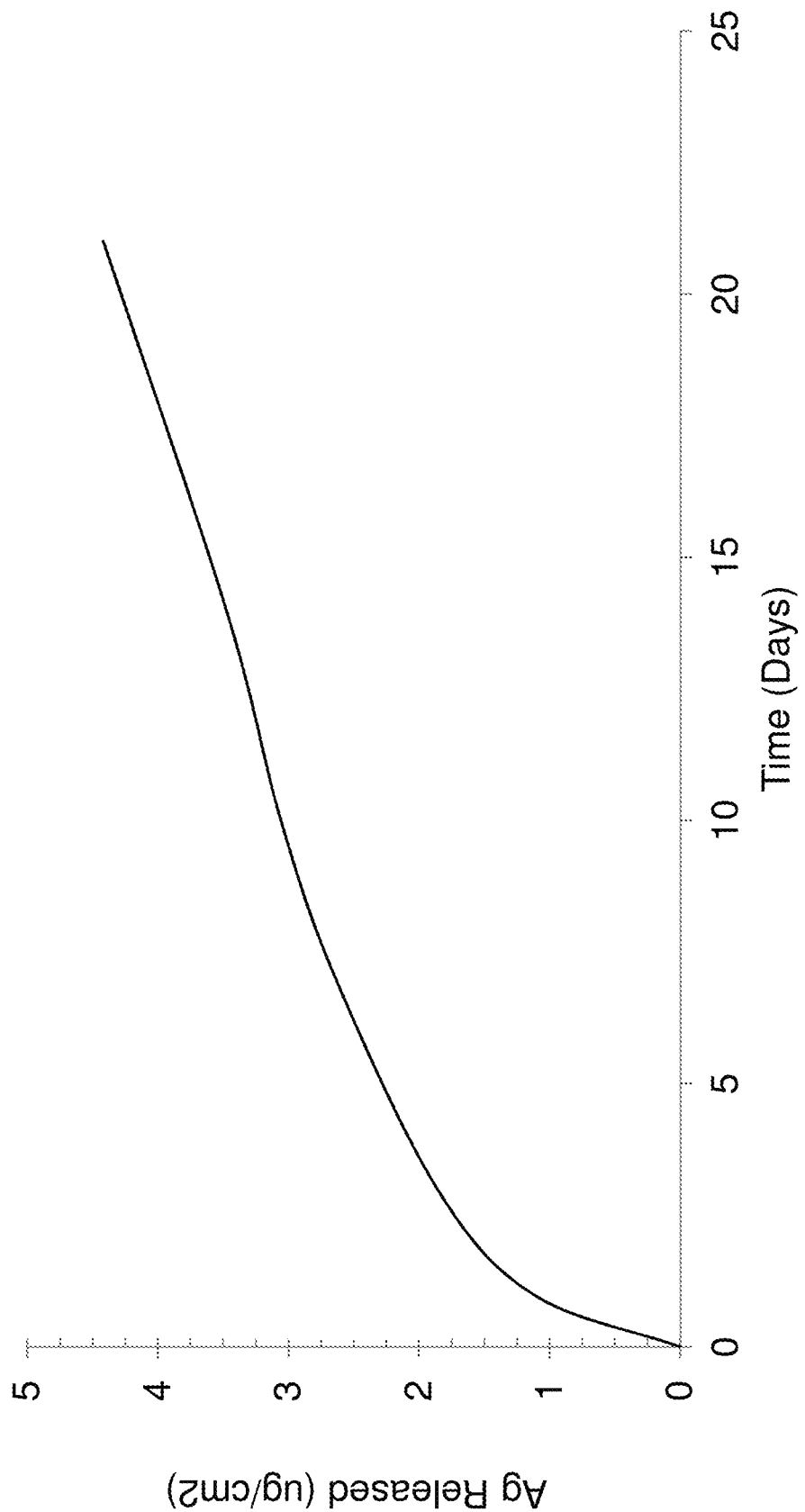
FIG. 17 depicts silver release data of the silver nanoparticle coated fatty acid-derived biomaterial with gentamicin added in-situ as described in Example 3.
Figure 18:
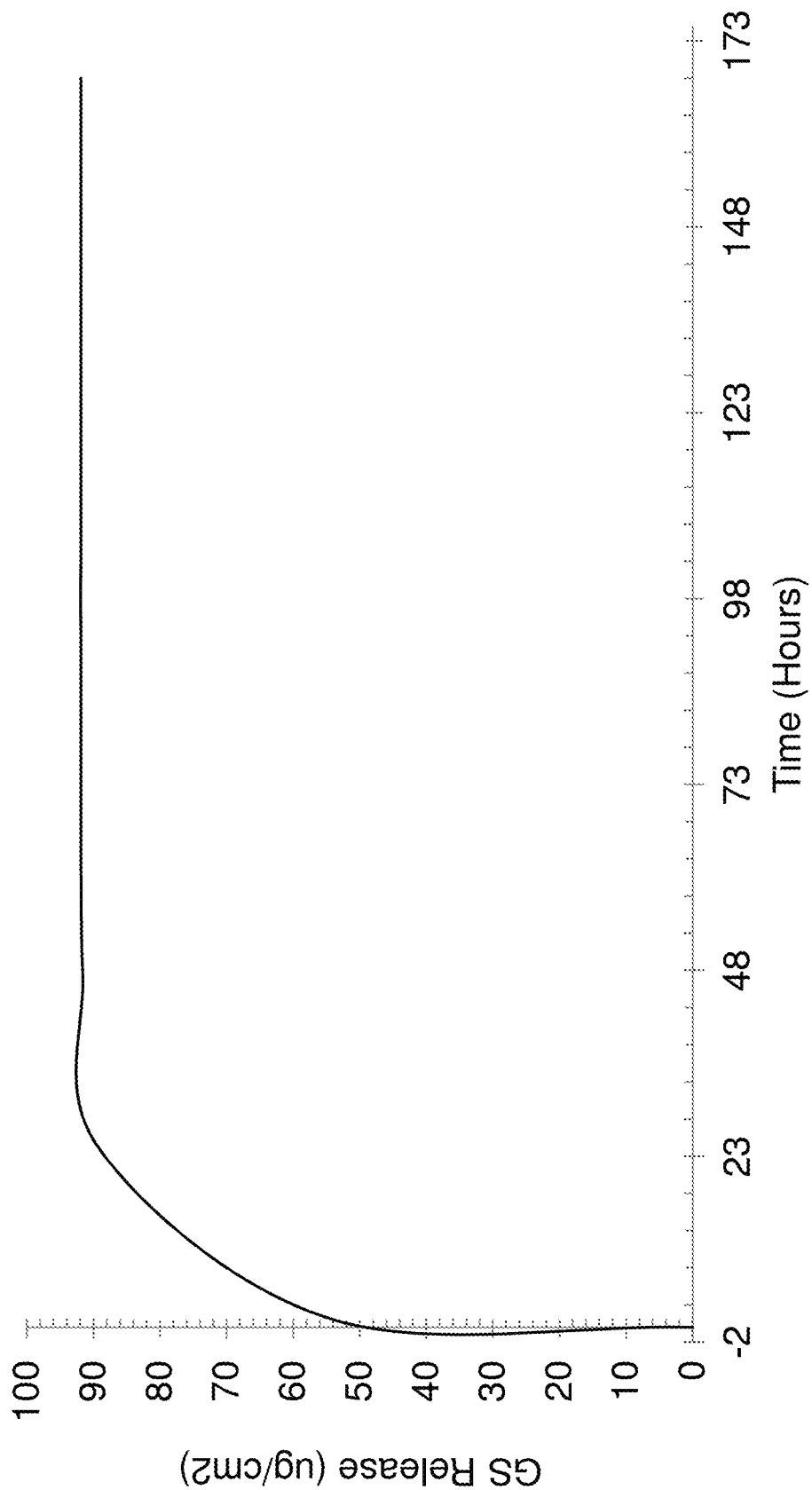
FIG. 18 depicts gentamicin release data of the silver nanoparticle coated fatty acid-derived biomaterial with gentamicin added in-situ as described in Example 3.

Fish oil, gentamicin powder and silver nanoparticles were appropriately massed into a cryogenic grinding polycarbonate center cylinder vial capped on one end with a stainless steel end plug. A stainless steel magnetic bar was added into the polycarbonate vial containing the formulation components and the open end was capped with a stainless steel end plug. The vial was then placed into the cryogenic grinding apparatus programmed to produce an alternating magnetic field that causes the stainless steel bar to impact the stainless steel end plugs of the polycarbonate vial containing the formulation components, resulting in a finely ground and homogenized formulation. The cryoground formulation was allowed to thaw, cast onto a medical device and thermally cured at 200° F. for 24 hours to form a solid coating. One possible mechanism for the formation of the gentamicin and nano-silver oil-derived biomaterial coating is as follows: fish oil, gentamicin and silver nanoparticles absorb oxygen; oxidation of the C=C bonds in the oil occurs; fatty acid and glycerides (mixture of mono, di- and tri) are formed; continued curing results in dehydration of neighboring carboxyl and hydroxyl functional groups; lactone/ester cross-links are formed between fatty acids and glycerides; and the coating solidifies into a bioabsorbable gel containing cross-linked fatty acids, glycerides, gentamicin and Ag nano particles The release of gentamicin and silver ions in $\mu g/cm^2$ was tested in aqueous conditions. FIG. 17 illustrates a plot of the silver ions released over approximately three weeks whereas FIG. 18 shows the release profile of gentamicin in water. The silver release profile was gradual but the gentamicin produced a burst of the drug dose in less than 48 hours. This indicates that in this particular embodiment, silver would be slow releasing over extended time periods but the gentamicin would be fast releasing within a relatively short amount of time in an aqueous environment.

Another method of incorporating gentamicin into the silver nanoparticle fatty acid biomaterial coating is accomplished by spraying a solution of gentamicin sulfate on a cured silver nanoparticle fatty acid-derived biomaterial sample. The antibiotic solution is prepared by dissolving gentamicin in water; the concentration of the gentamicin can range between 1 and 50 mg/ml depending on how much is drug to be loaded onto the surface of the coating and how many sprayed layers are to be applied. The material can be prepared as follows: fish oil and silver nanoparticles absorb oxygen; oxidation of the C=C bonds in the oil occurs; fatty acid and glycerides (mixture of mono, di- and tri) are formed; continued curing results in dehydration of neighboring carboxyl and hydroxyl functional groups; lactone/ester cross-links are formed between fatty acids and glycerides; the material solidifies into a bioabsorbable gel containing cross-linked fatty acids, glycerides, and Ag nano particles; and gentamicin is sprayed onto the surface of the cross-linked silver nanoparticle biomaterial and allowed to dry.

Figure 19:
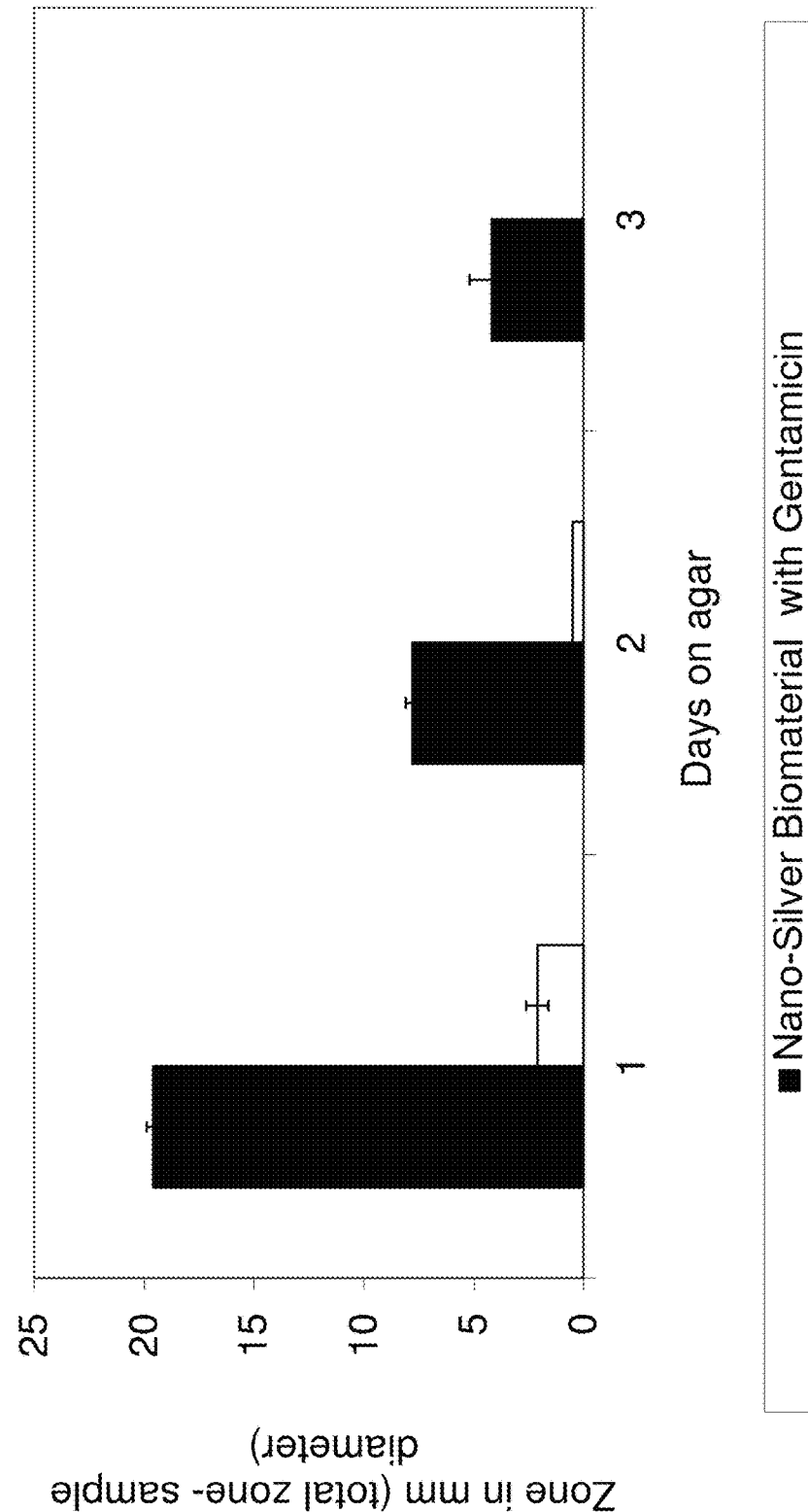
FIG. 19 provides a bar graph of zones measured in mm of Silver nanoparticle fatty acid-derived biomaterial surface coated with gentamicin, a Silver nanoparticle fatty acid-derived biomaterial and a fatty acid-derived biomaterial control in a three day zone of inhibition study as described in Example 5.

The efficacy of the gentamicin sprayed silver nanoparticle fatty acid-derived biomaterial coating was evaluated by zone of inhibition (ZOI) and bacterial adherence tests shown in FIGS. 19 and 20. In the ZOI test, silver nanoparticle fatty acid biomaterial coating and gentamicin sprayed silver nanoparticle fatty acid biomaterial coating sample discs with a 0.5 inch diameter were placed on a bed of *S. aureus* bacteria in an agar plate and incubated for 24 hours before transferring the disc to a fresh bacterial agar plate. In this particular test, the ZOI was done for 3 days comparing the silver nanoparticle fatty acid biomaterial coating with and without the gentamicin sprayed layer. The plot in FIG. 19 shows that both silver nanoparticle fatty acid biomaterial coating with and without the gentamicin sprayed layer were efficacious in reducing the number of bacteria growing around the surface of the device but the sample with the added gentamicin layer was more efficacious in this regard when compared to the sample without a gentamicin layer. The bacterial adherence results in FIG. 20 similarly show that significantly fewer bacteria adhered to the surface of the gentamicin sprayed silver nanoparticle fatty acid-derived biomaterial. Addition of gentamicin to the silver nanoparticle fatty acid-derived biomaterial therefore improved the antibacterial properties of the biomaterial coating.

Figure 21:
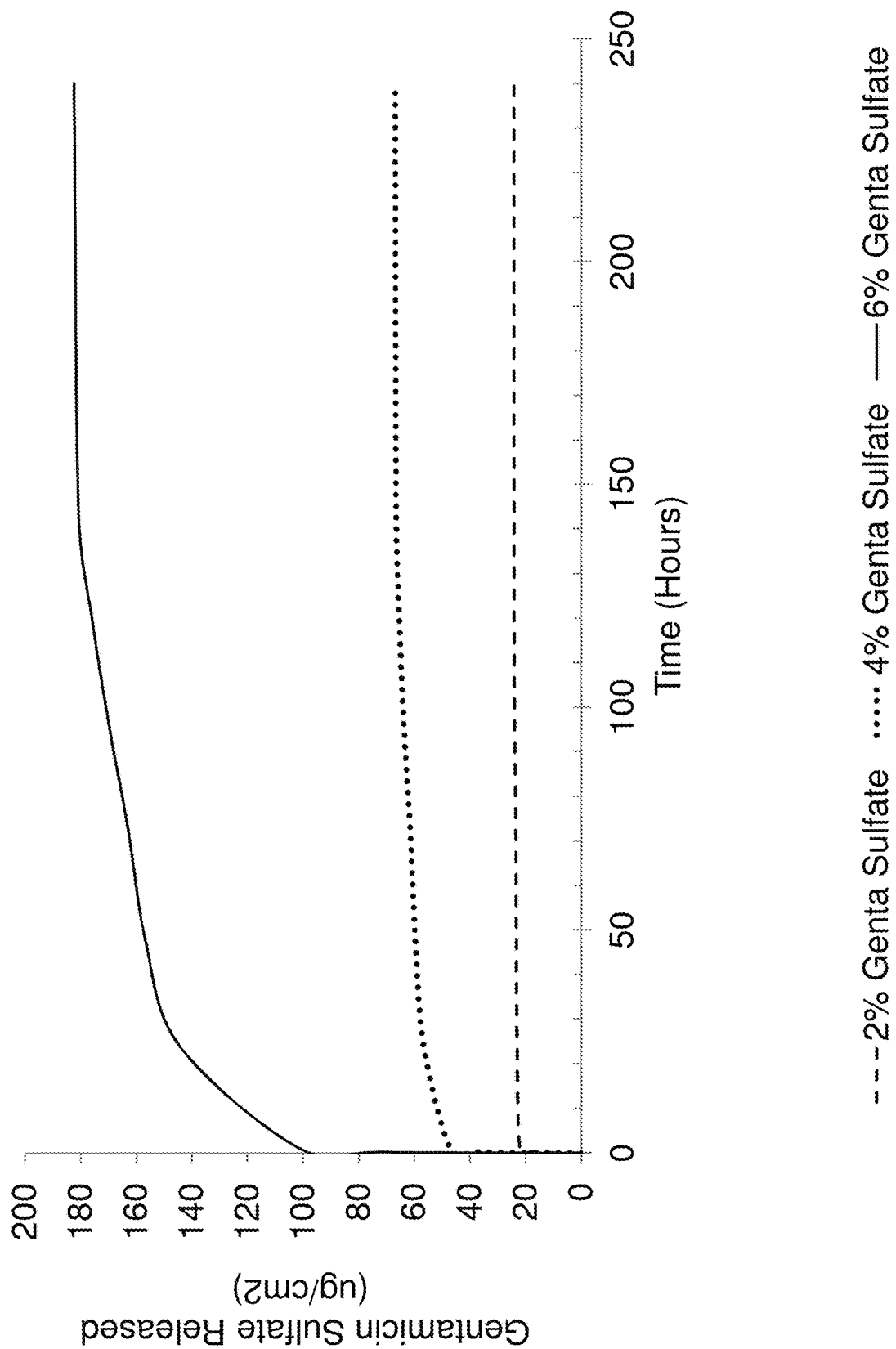
FIG. 21 depicts the drug release data of gentamicin in an aqueous media from gentamicin Silver nanoparticle fatty acid film-derived biomaterial samples with different gentamicin concentrations loaded onto the samples as described in Example 5.
Figure 22:
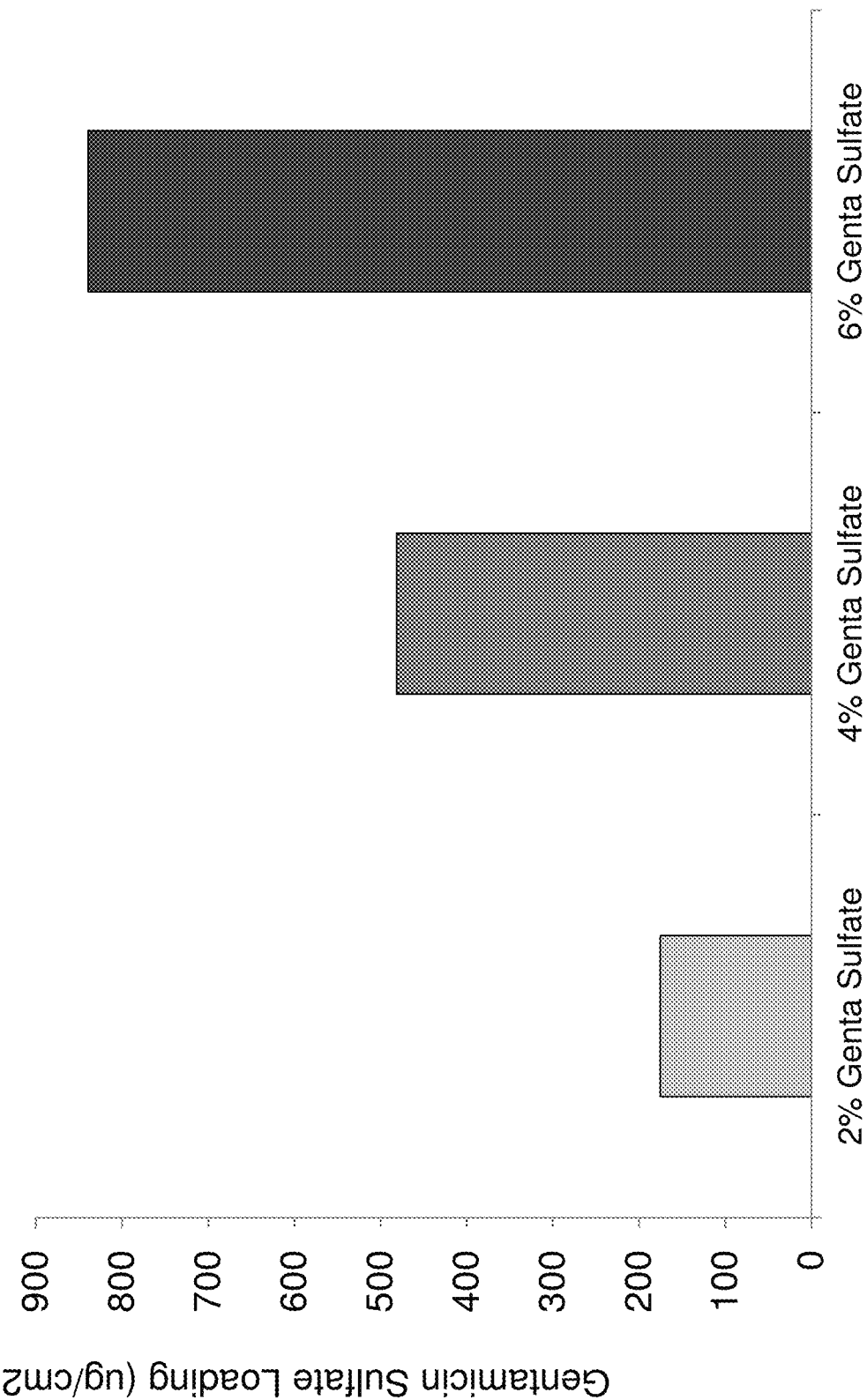
FIG. 22 depicts the gentamicin assay loading data in $\mu g/cm^2$ in gentamicin Silver nanoparticle fatty acid film-derived biomaterial samples containing different gentamicin concentrations as described in Example 5.

In another embodiment of this invention, a fatty acid-derived film containing silver nanoparticles and gentamicin is prepared and cast onto a polymeric medical device. The mechanism used to form the gentamicin and silver nanoparticle fatty acid-derived biomaterial coating is as follows: fatty acid film particles, genatmicin and silver nanoparticles thoroughly mixed together; the blended particles, gentamicin and Ag nanoparticles are pressed into a thin film under heat and pressure; and the gentamicin fatty acid silver nanoparticle film is cast onto a polymeric device.

gentamicin release in aqueous media occurred as a burst over 250 hours but the total amount released was able to be modified by varying the total amount of gentamicin loaded onto the sample as shown in FIG. 21. The total amount of gentamicin loaded per sample can also be controlled by altering the amount of gentamicin added to the initial formulation. Assay values of gentamicin in this example were determined to be between 180 and 900 $\mu g/cm^2$ for concentrations of gentamicin ranging between 2 and 6% (FIG. 22).

Example 6

Formation of Silver Nano-Particle Fatty Acid-Derived Biomaterial in Combination with Chlorhexidine Diacetate In this example, chlorhexidine diacetate is used as an additional antimicrobial agent to augment the silver nanoparticle fatty acid-derived biomaterial. One possible mechanism for the formation of the silver nanoparticle fatty acid biomaterial surface coated with chlorhexidine diacetate is as follows: fish oil and silver nanoparticles absorb oxygen: oxidation of the C=C bonds in the oil occurs; fatty acid and glycerides (mixture of mono, di- and tri) are formed; continued curing results in dehydration of neighboring carboxyl and hydroxyl functional groups; lactone/ester cross-links are formed between fatty acids and glycerides; the coating solidifies into a bioabsorbable gel containing cross-linked fatty acids, glycerides, and Ag nano particles; and chlorhexidine is sprayed onto the surface of the cross-linked silver nanoparticle biomaterial and allowed to dry.

The antimicrobial solution was prepared by dissolving chlorhexidine diacetate in water to a final concentration of 10 mg/ml and was evenly sprayed onto the surface of the silver nanoparticle fatty acid-derived biomaterial created using the methodology described in Example 4.

Figure 23:
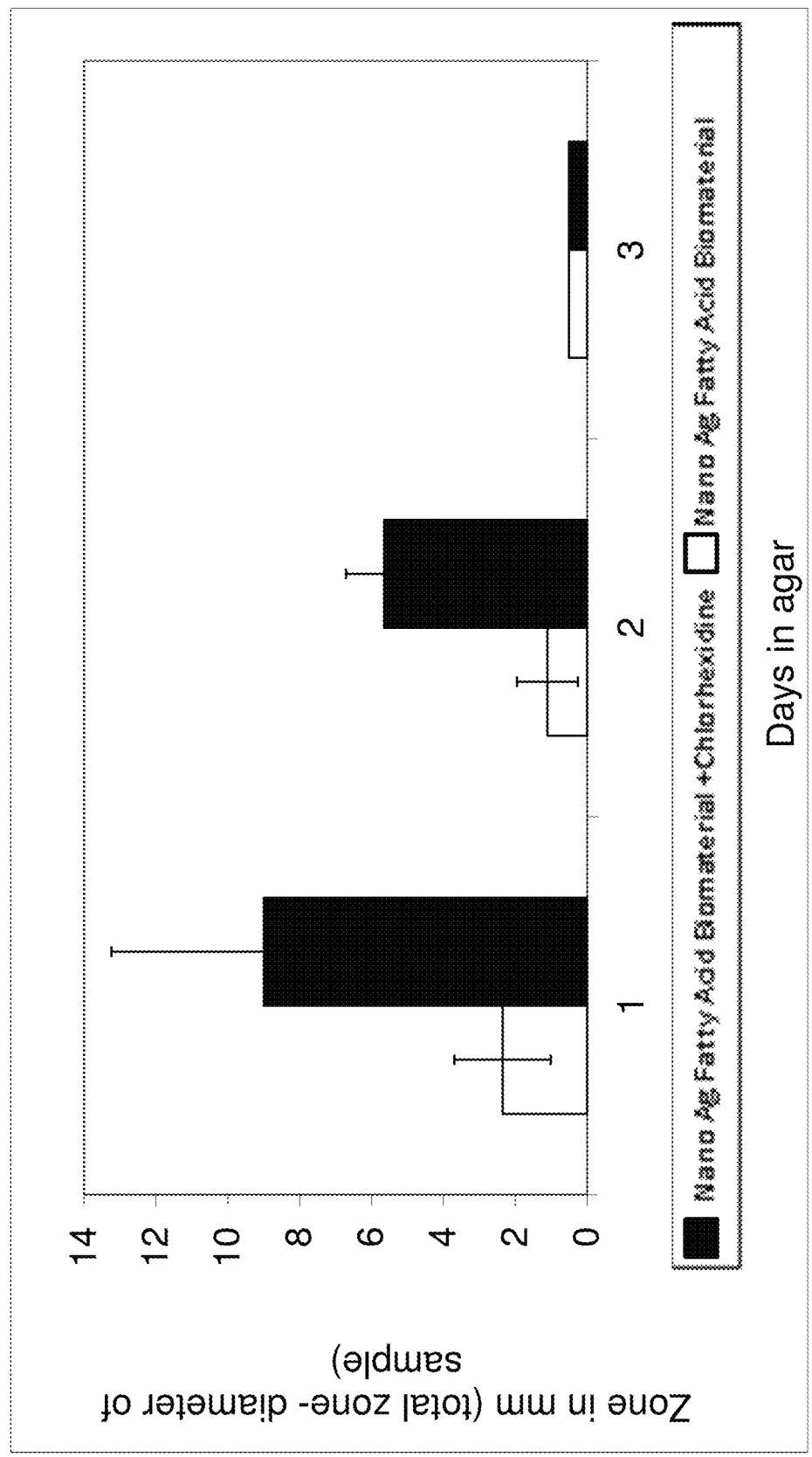
FIG. 23 shows a bar graph of zones measured in mm from a three day bacterial zone of inhibition study of Silver nanoparticle fatty acid-derived biomaterial surface coated with chlorhexidine diacetate and a Silver nanoparticle fatty acid-derived biomaterial control.
Figure 24:
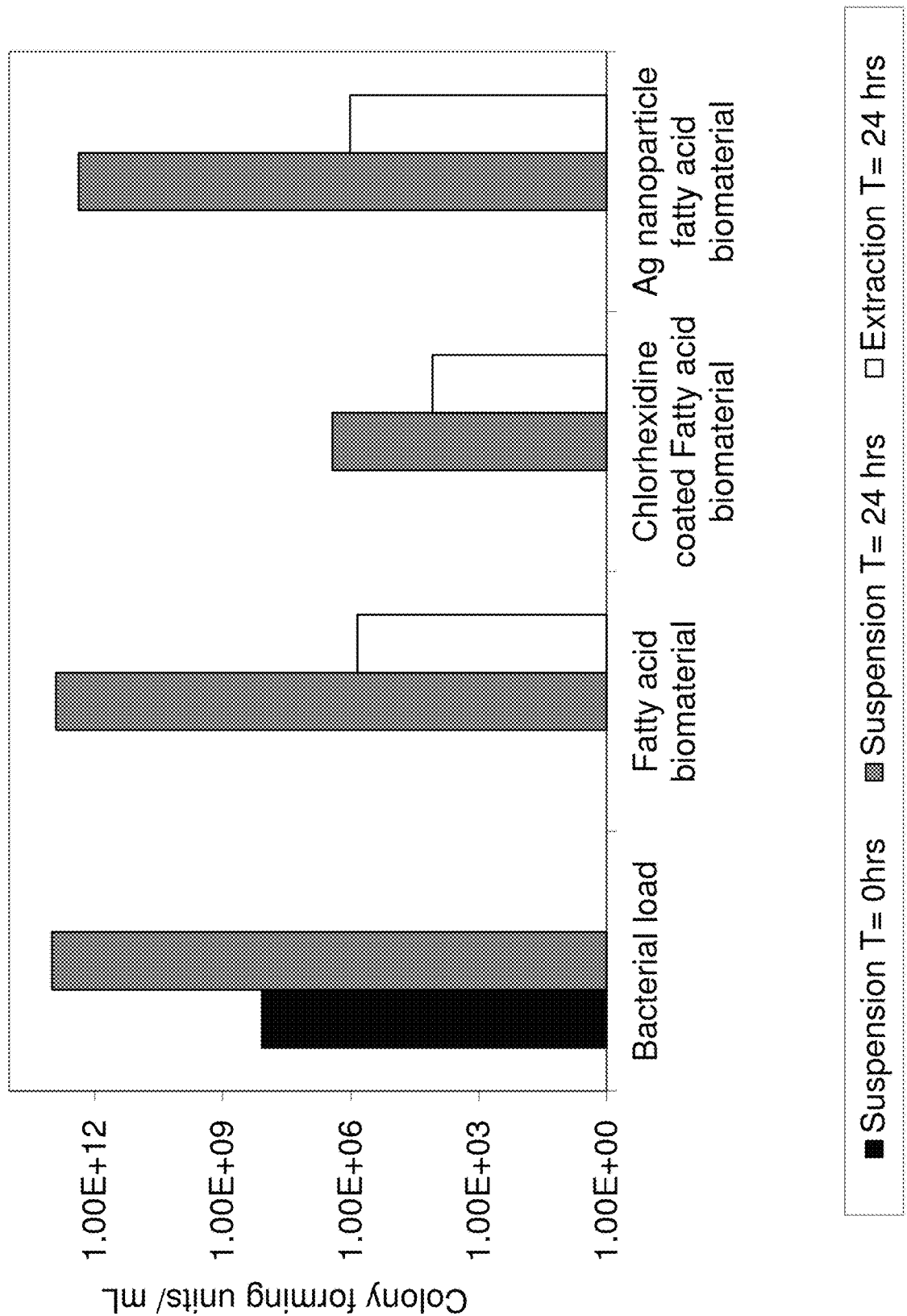
FIG. 24 is a bar graph of a bacterial adherence assay of silver nanoparticle fatty acid biomaterial surface coated with chlorhexidine diacetate, chlorhexidine-silver fatty acid biomaterial surface coated with chlorhexidine diacetate together with fatty acid biomaterial and silver nanoparticle fatty acid biomaterial controls.

Bacterial adherence and ZOI tests were performed on the chlorhexidine sprayed silver nanoparticle fatty acid-derived biomaterial samples. The ZOI test samples had measurable zones for three days with the chlorhexidine sprayed silver nanoparticle fatty acid-derived biomaterial samples having larger zones compared to the control silver nanoparticle fatty acid biomaterial samples without chlorhexidine as show in FIG. 23. Bacterial adherence test results of the chlorhexidine sprayed silver nanoparticle fatty acid-derived biomaterial samples showed that adding a chlorhexidine layer significantly reduced the number of bacteria adhered to the surface of the when compared to a silver nanoparticle fatty acid-derived biomaterial control sample without chlorhexidine as shown in FIG. 24.

Example 7

Figure 25:
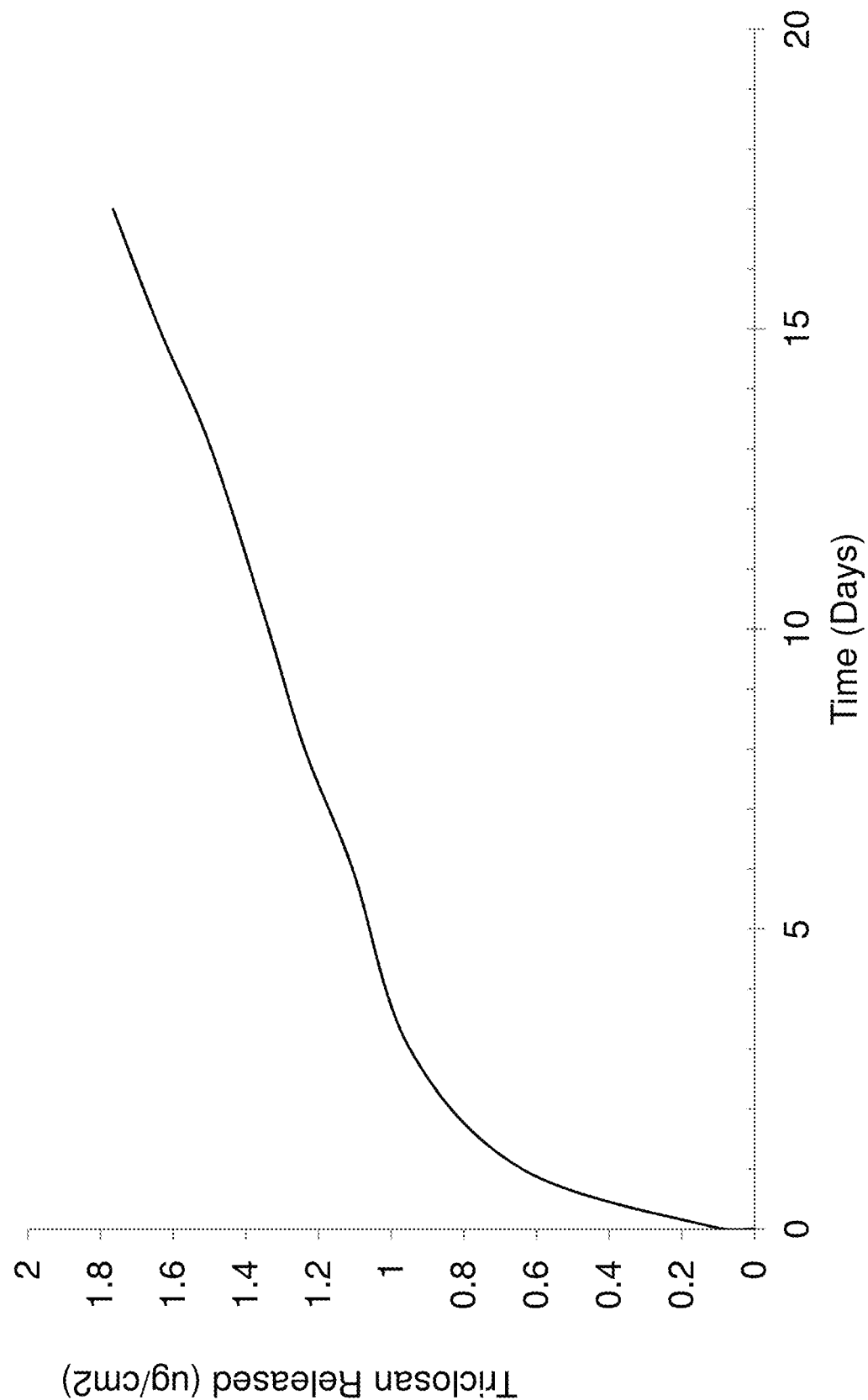
FIG. 25 shows triclosan release data from a Silver nanoparticle fatty acid-derived biomaterial sample surface coated with Triclosan.
Figure 26:
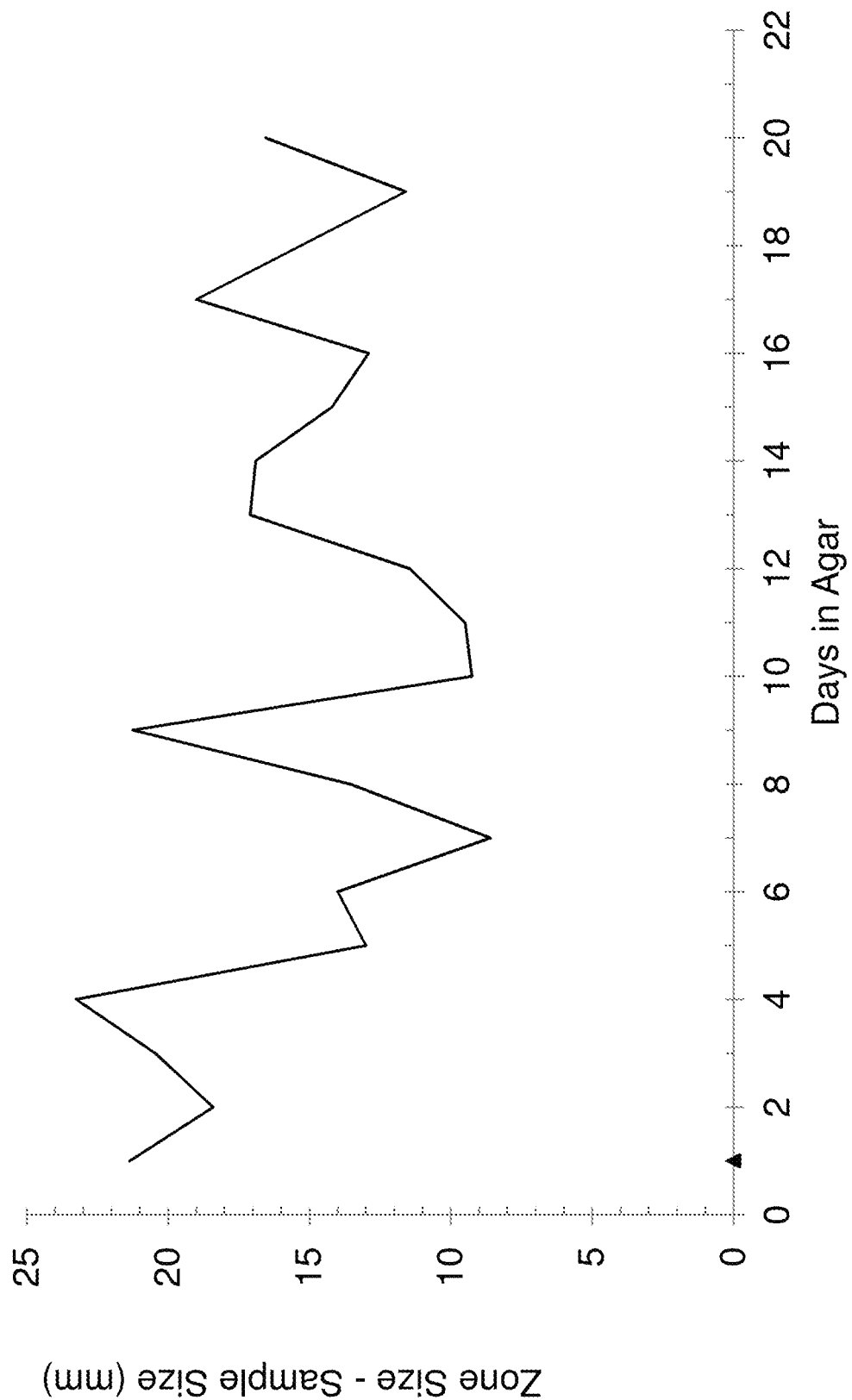
FIG. 26 illustrates the zones measured from a Silver nanoparticle fatty acid-derived biomaterial sample surface coated with triclosan over approximately three weeks.
Figure 27:
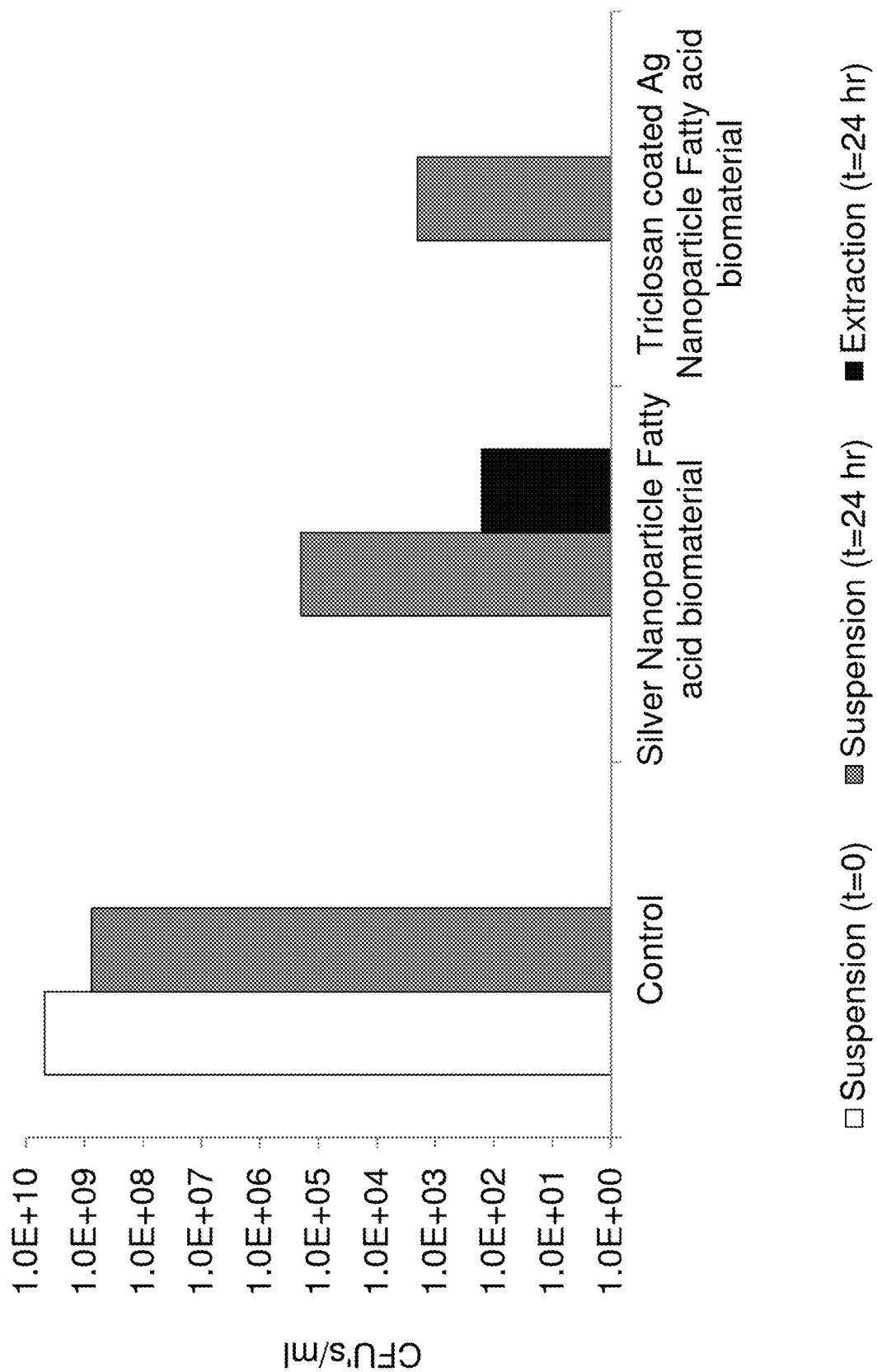
FIG. 27 is a S. aureus bacterial suspension assay plot of Silver nanoparticle fatty acid-derived biomaterial sample surface coated with Triclosan.

Formation of Silver Nano-Particle Fatty Acid-Derived Biomaterial in Combination with Triclosan This example describes the use of triclosan to augment the antimicrobial properties of the silver nanoparticle fatty acid-derived biomaterial coating. One possible mechanism for the formation of the silver nanoparticle fatty acid-derived biomaterial surface coated with triclosan is as follows: fish oil and silver nanoparticles absorb oxygen; oxidation of the C═C bonds in the oil occurs; fatty acid and glycerides (mixture of mono, di- and tri) are formed; continued curing results in dehydration of neighboring carboxyl and hydroxyl functional groups; lactone/ester cross-links are formed between fatty acids and glycerides; the coating solidifies into a bioabsorbable gel containing cross-linked fatty acids, glycerides, and Ag nano particles; and triclosan is applied to the surface of the solidified coating containing cross-linked fatty acids, glycerides, and Ag nano particles A triclosan solution was prepared by dissolving triclosan in ethanol to a concentration ranging between 1 and 20 mg/ml and the solution was then sprayed onto the silver fatty acid coating surface created using the process described in Example 4. Multiple Layers were Sprayed on the Surface if Lower Triclosan Solutions were used and fewer triclosan layers were sprayed on the coating surface if higher triclosan solutions were used. An illustration of triclosan dissolution in a buffer solution is shown in FIG. 25 showing low level amounts of triclosan are gradually released in this medium. The efficacy of the triclosan sprayed silver nanoparticle fatty acid-derived biomaterial coating was evaluated by zone of inhibition (ZOI) and bacterial adherence tests shown in FIGS. 26 and 27. The plot in FIG. 26 showed improved zones measured that were relatively consistent over a period of approximately 3 weeks. Previous ZOI tests of the silver nanoparticle fatty acid biomaterial coating without surface sprayed Triclosan, exhibited zones for approximately 3 days. Addition of triclosan to the coating surface therefore significantly improved the bacteriostatic capabilities of the silver nanoparticle fatty acid biomaterial coating. FIG. 27 further depicts the number of colony forming units enumerated per ml of media after performing a *S. aureus* bacterial suspension assay using various fatty acid biomaterial samples without silver, with silver and with both silver and triclosan present. This assay monitors the ability of the antimicrobial to elute from the device to the surrounding media or environment. FIG. 27 showed that the lowest number of colony forming units within the suspension media was obtained from the fatty acid biomaterial coated with both triclosan and silver. The results of the performed tests also showed reduced bacterial colony forming units extracted from the surface of the silver nanoparticle fatty acid biomaterial silver compared to the control but the most significant reduction was noted in the silver nanoparticle fatty acid biomaterial with triclosan which had no bacteria adhered to the surface.

In a related embodiment, triclosan can be incorporated into the silver nanoparticle fatty acid-derived coating and additional sprayed with a layer of triclosan to further improve upon antibacterial properties. The mechanism used to form this triclosan silver nanoparticle fatty acid-derived biomaterial coating surface coated with triclosan is as follows: fish oil, triclosan and silver nanoparticles absorb oxygen; oxidation of the C═C bonds in the oil occurs; fatty acid and glycerides (mixture of mono, di- and tri) are formed; continued curing results in dehydration of neighboring carboxyl and hydroxyl functional groups; lactone/ester cross-links are formed between fatty acids and glycerides; the coating solidifies into a bioabsorbable gel containing cross-linked fatty acids, glycerides, gentamicin and Ag nano particles; solidified coating containing fatty acids, triclosan, and Ag nanoparticles is surface coated with an additional layer of triclosan.

Figure 28:
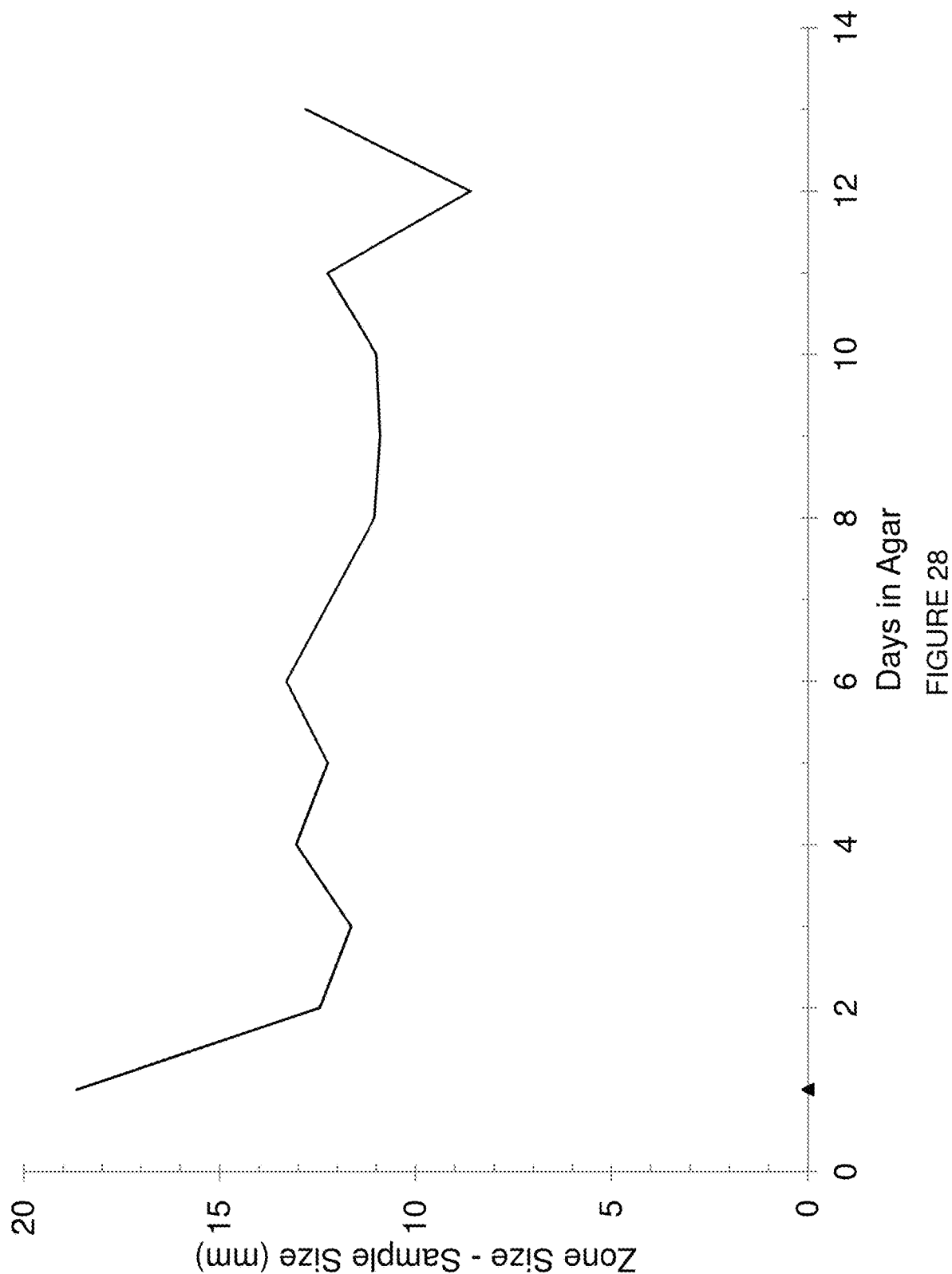
FIG. 28 portrays a S. aureus zone of inhibition plot showing the zone sizes measured from a Triclosan-Silver nanoparticle fatty acid-derived biomaterial triclosan surface coated sample over two weeks.
Figure 29:
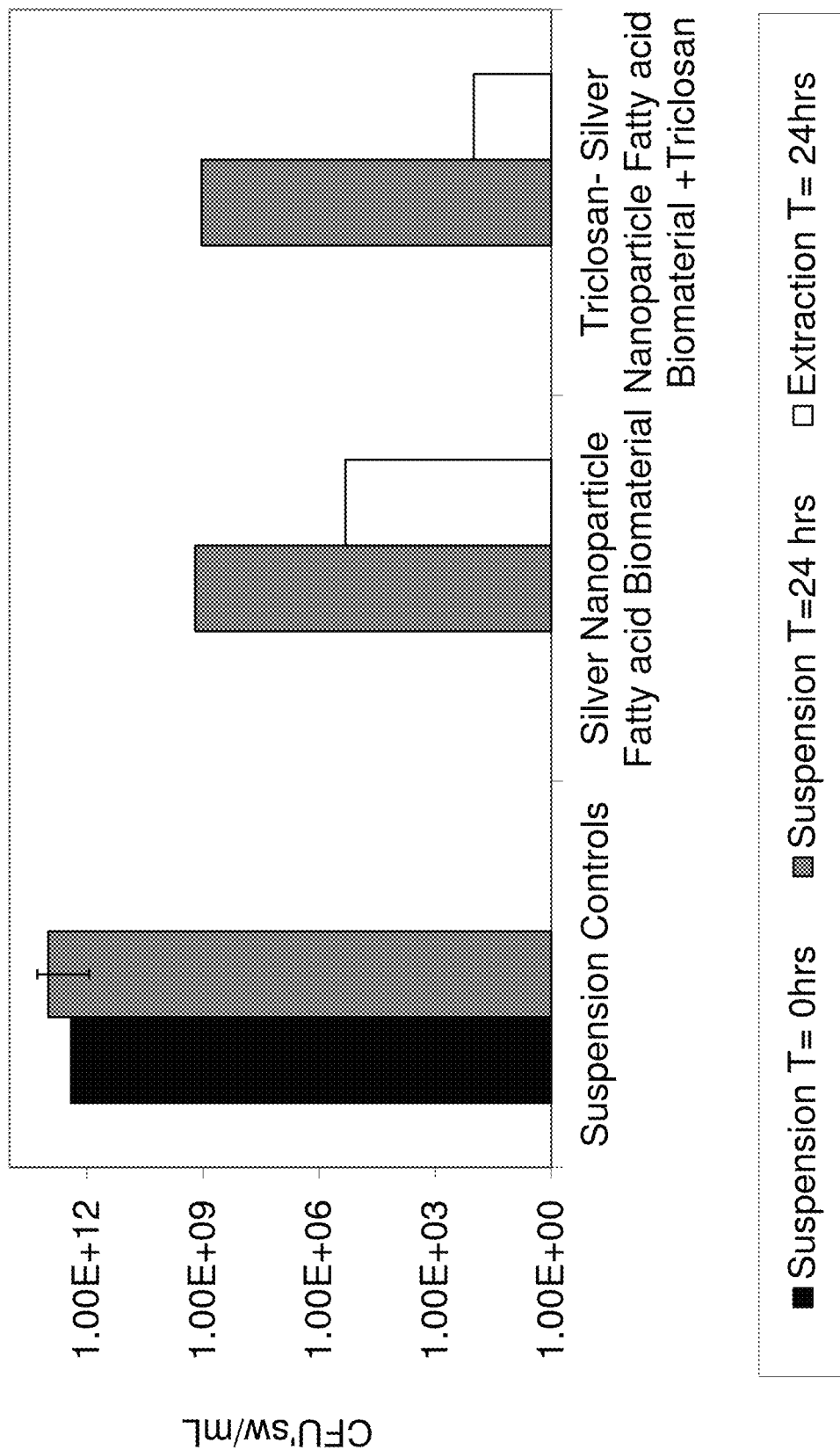
FIG. 29 is a S. aureus bacterial adherence plot of Silver nanoparticle fatty acid-derived biomaterial sample surface coated with Triclosan.

Sample preparation involves combining 1% triclosan powder, 1% silver nanoparticles and fish oil, thoroughly mixing the formulation which is then cast onto a medical device and thermally cured to solidify the coating. The surface of the solid coating containing triclosan, silver nanoparticles and fatty acids is then sprayed with a 1-20 mg/ml triclosan solution. FIG. 28 depicts a plot of ZOI results obtained from triclosan silver nanoparticle fatty acid-derived samples surface coated with triclosan. Significant zones were measured through day 13 demonstrating a high antimicrobial efficacy of these samples. The results of the bacterial adherence test illustrated in FIG. 29 were acquired using bacterial adherence counts extracted from the surface of the device after 24 hours. The extraction bacterial counts obtained after 24 hours showed that the silver fatty acid biomaterial with triclosan had the lowest number of colony forming units extracted from the sample's surface.

In another related embodiment, triclosan is incorporated into the silver nanoparticle fatty acid-derived biomaterial before the coating formulation is thermally cured (i.e., triclosan not sprayed on the surface of the finished device). One possible mechanism for the formation of the triclosan and nano-silver hydrophobic oil-derived cross-linked biomaterial coating is as follows: fish oil, triclosan and silver nanoparticles absorb oxygen; oxidation of the C═C bonds in the oil occurs; fatty acid and glycerides (mixture of mono, di- and tri) are formed; continued curing results in dehydration of neighboring carboxyl and hydroxyl functional groups; lactone/ester cross-links are formed between fatty acids and glycerides; the coating solidifies into a bioabsorbable gel containing cross-linked fatty acids, glycerides, triclosan and Ag nano particles.

Figure 30:
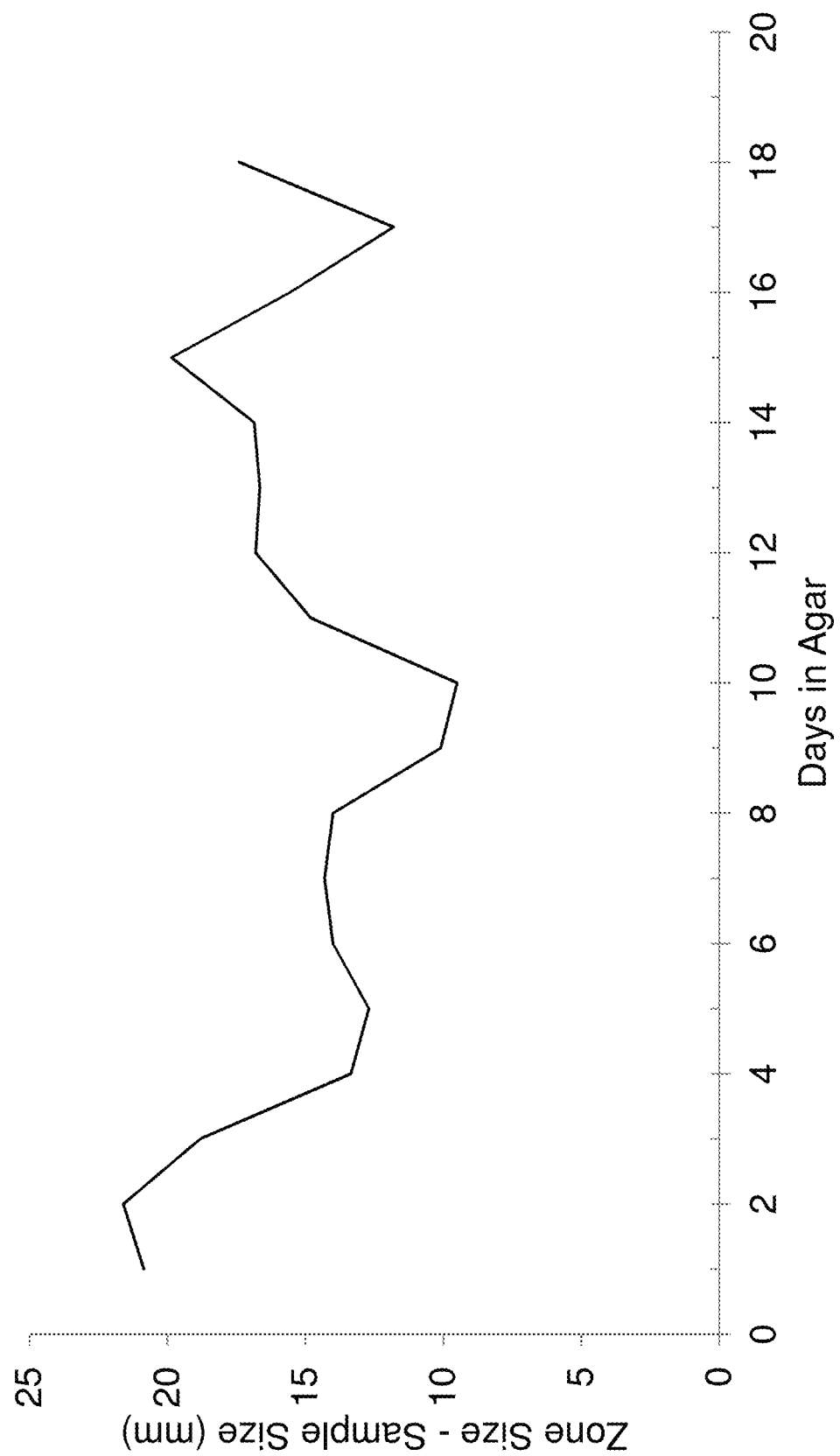
FIG. 30 portrays a S. aureus zone of inhibition plot showing the zone sizes measured from a Triclosan-Silver nanoparticle fatty acid-derived biomaterial sample over two and a half weeks.

ZOI test results showing antimicrobial properties of this coating are displayed in FIG. 30 which illustrates zones measured through day 19. This demonstrates that the coating has sufficient antimicrobial efficacy to prevent bacterial growth on the device in a *S. aureus* bacterial environment.

Example 8

Figure 31:
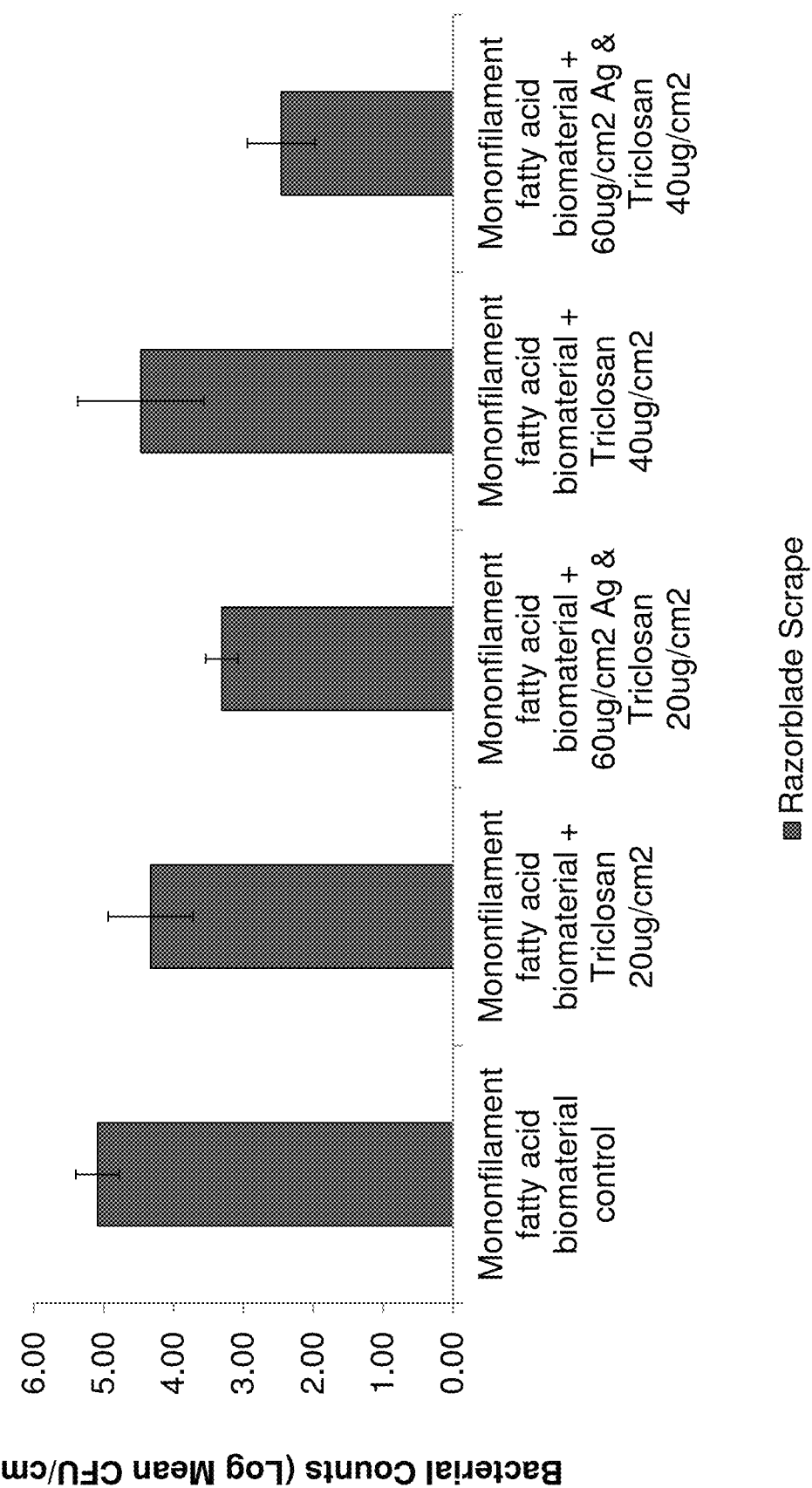
FIG. 31 illustrates the efficacy of different antimicrobial formulations of fatty acid-based biomaterials containing different doses of triclosan with and without silver nanoparticles as evaluated in an in-vivo infectability model with a clinical strain of MRSA.

Formation of Fatty Acid-Derived Biomaterial and Silver Nano-Particle Fatty Acid-Derived Biomaterial in Combination with Triclosan The efficacy of triclosan fatty acid-derived biomaterials were evaluated in an in-vivo infectability model using a clinical strain of MRSA. An additional embodiment of this invention uses triclosan coated onto the surface of a fatty acid-derived biomaterial sample without silver present within the coating matrix. Further yet, silver nanoparticles may be encapsulated within the lipid coating matrix as described in Example 4 and then surface coated with triclosan. The combination of triclosan and silver in the fatty acid-derived biomaterial coating may be serve to enhance the antimicrobial properties of the fatty acid-derived biomaterial coating as seen in FIG. 31. The plot displays bacterial counts scrapped from the samples' surface that represent 7 day explant samples obtained from an in vivo infectability study. The sample sets evaluated include fatty acid-derived biomaterial samples surface coated with 20 ug/cm$^2$ of triclosan and 60 ug/cm$^2$ silver nanoparticles in the fatty acid-derived biomaterial samples surface coated with 20 ug/cm$^2$ and 40 ug/cm$^2$ triclosan. While some efficacy was evident in all sample sets tested in this study, FIG. 31 demonstrates that the lowest bacterial counts were recorded in the sample sets which had both silver nanoparticles and triclosan. Adding triclosan to the surface of a fatty acid-derived biomaterial confers a benefit in reducing bacterial adherence onto the surface of the device but having both silver nanoparticles and triclosan present in the coating results in a more significant reduction of bacterial adherence as shown in FIG. 31. A possible synergistic effect between the silver encapsulated in the lipid coating and the surface coated triclosan may be attributed to the lower bacterial counts in samples with both triclosan and silver nanoparticles.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the invention, and exclusive use of all modifications that come within the scope of the appended claims is reserved. It is intended that the present invention be limited only to the extent required by the appended claims and the applicable rules of law.

All literature and similar material cited in this application, including, patents, patent applications, articles, books, treatises, dissertations and web pages, regardless of the format of such literature and similar materials, are expressly incorporated by reference in their entirety. In the event that one or more of the incorporated literature and similar materials differs from or contradicts this application, including defined terms, term usage, described techniques, or the like, this application controls.

The section headings used herein are for organizational purposes only and are not to be construed as limiting the subject matter described in any way.

While the present invention has been described in conjunction with various embodiments and examples, it is not intended that the present teachings be limited to such embodiments or examples. On the contrary, the present invention encompasses various alternatives, modifications, and equivalents, as will be appreciated by those of skill in the art.

The claims should not be read as limited to the described order or elements unless stated to that effect. It should be understood that various changes in form and detail may be made without departing from the scope of the appended claims. Therefore, all embodiments that come within the scope and spirit of the following claims and equivalents thereto are claimed.

The invention claimed is:

1. A material comprising:
  a plurality of fatty acid chains at least partially cross-linked together to form a bioabsorbable gel; and
  a silver fatty acid salt formed in an aqueous environment with at least some of the at least partially cross-linked fatty acid chains within the material, wherein the silver fatty acid salt comprises silver ions and is characterized by an FTIR peak at about 1512 cm$^{-1}$.

2. The material of claim 1, wherein the silver fatty acid salt is formed from an interaction between the at least partially cross-linked fatty acid chains and an aqueous silver solution.

3. The material of claim 2, wherein the silver solution includes silver nitrate or silver acetate.

4. The material of claim 1, wherein the at least partially cross-linked fatty acid chains are cross-linked together by at least partially curing an oil.

5. The material of claim 4, wherein the fatty acid chains are omega-3 fatty acids and the oil is a fish oil.

6. A coating or film comprising the material of claim 1.

7. The coating or film of claim 6 having an additional antimicrobial compound applied to an outer surface of the coating or film.

8. The material of claim 1, wherein the silver fatty acid salt is dispersed in a soaked pattern in the material.

9. The material of claim 1, wherein the silver fatty acid salt is suspended uniformly in the material.

10. The material of claim 1, wherein the at least partially cross-linked plurality of fatty acid chains include one or more cross-links selected from the group consisting of ester cross-links, peroxide bridges, ether bridges and hydrocarbon bridges.

11. The material of claim 1, wherein the silver fatty acid salt load in the material is sufficient to inhibit bacterial growth during implantation.

12. The material of claim 1, wherein when the material becomes hydrated in an aqueous environment the material releases silver ions.

13. The coating or film of claim 7, wherein the additional antimicrobial compound is triclosan.

14. A method for forming a material, comprising the steps of:
  at least partially curing an oil comprising fatty acids in order to at least partially cross-link chains of the fatty acids together to form the bioabsorbable gel;
  soaking the bioabsorbable gel in an aqueous silver solution; and
  evaporating a solvent from the aqueous silver solution to form silver fatty acid salts within the bioabsorbable gel so as to form the material according to claim 1.

15. The method of claim 14, wherein the aqueous silver solution includes silver acetate or silver nitrate.

16. The method of claim 14, wherein the at least partially curing includes at least partially curing the fatty acids to form a biomaterial on a medical device.

17. The method of claim 16, wherein the medical device is a bandage, a stent, a graft, a shunt, a catheter, a balloon, or a surgical mesh.

18. A method for forming a material according to claim 1, comprising the step of:
  at least partially curing an oil to at least partially oxidize fatty acids within the oil to form a pre-cured oil;
  combining the pre-cured oil with a substantially uncured oil to form an oil formulation;
  combining an aqueous silver solution with the oil formulation; and
  curing the oil formulation and the aqueous silver solution combination to react silver ions of the aqueous silver solution with the pre-cured oil of the oil formulation to convert the aqueous silver solution at least partially into elemental silver within the material.

19. The method of claim 18, wherein the pre-cured oil and the substantially uncured oil both include fish oil.

20. The method of claim 18, wherein curing also includes cross-linking fatty acids within the oil formulation to each other.

21. The method of claim 18, wherein the pre-cured oil and the substantially uncured oil are combined in an approximately equal ratio.

22. The method of claim 18, wherein at least partially curing the oil includes forming hydroperoxides in the oil, and wherein the silver ions react with the hydroperoxides to form the elemental silver from the aqueous silver solution.

* * * * *